(12) United States Patent
Kim et al.

(10) Patent No.: US 11,332,742 B1
(45) Date of Patent: May 17, 2022

(54) MAD NUCLEASES

(71) Applicant: Inscripta, Inc., Boulder, CO (US)

(72) Inventors: Juhan Kim, Boulder, CO (US);
Benjamin Mijts, Boulder, CO (US);
Aamir Mir, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/567,800

(22) Filed: Jan. 3, 2022

Related U.S. Application Data

(60) Provisional application No. 63/134,938, filed on Jan. 7, 2021.

(51) Int. Cl.
*C12N 9/22* (2006.01)
*C12N 15/11* (2006.01)
*C12N 15/113* (2010.01)

(52) U.S. Cl.
CPC .............. *C12N 15/111* (2013.01); *C12N 9/22* (2013.01); *C12N 15/113* (2013.01); *C12N 2310/20* (2017.05); *C12N 2800/80* (2013.01)

(58) Field of Classification Search
CPC ....... C12N 15/111; C12N 15/113; C12N 9/22; C12N 2310/20
See application file for complete search history.

(56) References Cited

U.S. PATENT DOCUMENTS

| | | |
|---|---|---|
| 6,391,582 B2 | 5/2002 | Ying et al. |
| 6,837,995 B1 | 1/2005 | Vassarotti et al. |
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,227,576 B1 | 3/2019 | Cameron et al. |
| 10,266,851 B2 | 4/2019 | Chen |
| 10,704,033 B1 | 7/2020 | Kim et al. |
| 10,724,021 B1 | 7/2020 | Kim et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,927,385 B2 | 2/2021 | Kannan et al. |
| 2002/0139741 A1 | 10/2002 | Kopf |
| 2004/0110253 A1 | 6/2004 | Kappler et al. |
| 2006/0014137 A1 | 1/2006 | Ghosh et al. |
| 2007/0020761 A1 | 1/2007 | Yu et al. |
| 2010/0076057 A1 | 3/2010 | Sontheimer et al. |
| 2011/0294217 A1 | 12/2011 | Mcconnell-Smith et al. |
| 2013/0236970 A1 | 9/2013 | Anneren et al. |
| 2014/0068797 A1 | 3/2014 | Doudna et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2015/0024464 A1 | 1/2015 | Lippow et al. |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |

(Continued)

FOREIGN PATENT DOCUMENTS

| | | |
|---|---|---|
| EP | 2395087 | 12/2011 |
| EP | 3199632 | 8/2017 |

(Continued)

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids Research, 41(7):4336-43 (2013).

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Verwaal, et al., "CRISPR/Cpfl enables fast and simple genome editing of *Saccharamyces cerevisiae*", Yeast, 35:201-11 (2018).

(Continued)

*Primary Examiner* — Antonio Galisteo Gonzalez
(74) *Attorney, Agent, or Firm* — Sarah Brashears

(57) ABSTRACT

The present disclosure provides new RNA-guided nucleases for making rational, direct edits to nucleic acids in live cells; specifically, the present disclosure provides Type V MAD nucleases (e.g., RNA-guided nucleases or RGNs) with altered PAM preferences and/or altered activity at different temperatures or fidelity, and/or varied nuclease activities; all changes that may increase the versatility of a nucleic acid-guided nuclease for certain editing tasks.

8 Claims, 7 Drawing Sheets

Specification includes a Sequence Listing.

(56) References Cited

U.S. PATENT DOCUMENTS

| | | |
|---|---|---|
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0044525 A1 | 2/2017 | Kaper et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2018/0284125 A1 | 10/2018 | Gordon et al. |
| 2019/0017072 A1 | 1/2019 | Ditommaso et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0071660 A1 | 3/2020 | Spindler et al. |
| 2020/0095533 A1 | 3/2020 | Garst et al. |
| 2020/0216794 A1 | 7/2020 | Belgrader et al. |
| 2020/0263197 A1 | 8/2020 | Cheng et al. |
| 2020/0270632 A1 | 8/2020 | Roy et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO2014/143381 | 9/2014 |
| WO | WO 2014/144495 | 9/2014 |
| WO | WO2016/110453 | 7/2016 |
| WO | WO 2016/110453 | 7/2016 |
| WO | WO 2017/053902 | 3/2017 |
| WO | WO2017/075265 | 5/2017 |
| WO | WO 2017/078631 | 5/2017 |
| WO | WO 2017/083722 | 5/2017 |
| WO | WO 2017/106414 | 6/2017 |
| WO | WO2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO2017/216392 | 12/2017 |
| WO | WO 2017/216392 | 12/2017 |
| WO | WO 2017/223330 | 12/2017 |
| WO | WO2017/223330 | 12/2017 |
| WO | WO 2018/031950 | 2/2018 |
| WO | WO 2018/071672 | 4/2018 |
| WO | WO 2018/083339 | 5/2018 |
| WO | WO2018/152325 | 8/2018 |
| WO | WO2018/172556 | 9/2018 |
| WO | WO 2018/191715 | 10/2018 |
| WO | WO2019/006436 | 1/2019 |
| WO | WO2019/055878 | 3/2019 |
| WO | WO2019/200004 | 10/2019 |
| WO | WO2019/209926 | 10/2019 |
| WO | WO2020/005383 | 1/2020 |
| WO | WO2020/021045 | 1/2020 |
| WO | WO2020/074906 | 4/2020 |
| WO | WO-2021154866 A1 * | 8/2021 |
| WO | WO-2021178933 A2 * | 9/2021 |

OTHER PUBLICATIONS

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt. 4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962, Jun. 1, 2003.
Farasat et al., "A Biophysical Model of CRISPR/Cas9 Activity for Rational Design of Genome Editing and Gene Regulation," PLoS Comput Biol., 29:12(1):el004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologics", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20(1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.

(56) References Cited

OTHER PUBLICATIONS

International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.
Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 Rna polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.
Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols for their delivery into mammalian cells and mouse zygotes", Methods 121-122, p. 16-28, Mar. 23, 2017.
Jaitin, et al., "Dissecting Immune Circuits by Linking CRISPR-Pooled Screens with Single-Cell RNA-Seq", Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864.ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR guides enables scalable, multiplexed, and multi-omic Perturb-Seq", bioRxiv; doi:http://dx.doi.org/10.1101/503367, p. 1-26, Dec. 21, 2018.
Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.
International Search Report and Written Opinion for International Application No. PCT/US21/35807, dated Nov. 24, 2021, p. 1-21.
International Search Report and Written Opinion for International Application No. PCT/US21/50338, dated Dec. 10, 2021, p. 1-17.
International Search Report and Written Opinion for International Application No. PCT/US21/43097, dated Nov. 19, 2021, p. 1-12.
International Search Report and Written Opinion for International Application No. PCT/US21/39872, dated Oct. 27, 2021, p. 1-14.
International Search Report and Written Opinion for International Application No. PCT/US21/48566, dated Dec. 10, 2021, p. 1-10.
Filsinger, et al., "Characterizing the portability of RecT-mediated oligonucleotide recombination", bioRxiv, Apr. 15, 2020, doi:org/10.1101/2020.04.14.041095, p. 1-25.
Nelson, et al., "Engineered pegRNAs improve prime editing efficiency", Nature Biotechnology, Jul. 25, 2021, doi.org/10.1038/s41587-021-01039-7, p. 1-14.
Yu, et al., "Improved delivery of Cas9 protein/gRNA complexes using lipofectamine CRISPRMAX", Biotechnol Ltt, Feb. 18, 2016, doi 10.1007/s10529-016-2064-9, p. 919-929.
Bengali, et al., "Gene Delivery Through Cell Culture Substrate Adsorbed DNA Complexes", Biotechnol Bioeng., May 5, 2005, doi:10.1002/bit.20393, p. 1-23.
Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.
Takahashi, et al., "Integration of CpG-free DNA induces de novo methylation of CpG islands in pluripotent stem cells," Science, May 5, 2017, vol. 356, No. 6337, pp. 1-7.
Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.
Fayazpour, F., "Exploring New Applications for Photophysically Encoded Mircrocarriers", Ghent University Faculty of Pharmaceutical Sciences, Thesis Submission, Sep. 2008, 169 pages.

(56) References Cited

OTHER PUBLICATIONS

Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.

Elvin, et al., "Modified bacteriophage lambda promoter vectors for overproduction of proteins in *Escherichia coli*", Gene, 87, Sep. 15, 1989, p. 123-126.

Segall-Shapiro, et al., "Engineered promoters enable constant gene expression at any copy number in bacteria", Nature Biotechology, vol. 36, No. 4, Mar. 19, 2018, p. 352-363.

Xing, et al., "A CRISPR/Cas9 toolkit for multiplex genome editing in plants", BMC Plant Biology, 2014, p. 1-12.

Sun, et al., "A Single Multiplex crRNA Array for FnCpf1-Mediated Human Genome Editing," Molecular Therapy, Aug. 1, 2018, vol. 26, No. 8, pp. 2070-2076.

Kurata, et al., "Highly multiplexed genome engineering using CRISPR/Cas9 gRNA arrays," PLoS ONE, Sep. 17, 2018, vol. 13, No. 9, pp. 1-17.

Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42, (2014).

Unciti-Broceta, et al., "Combining Nebulization-Mediated Transfection and Polymer Microarrays for the Rapid Determination of Optimal Transfection Substrates", Journal of Combinatorial Chemistry, vol. 10, No. 2, Feb. 5, 2008, p. 179-184.

Fayazpour, et al., "Evaluation of Digitally Encoded Layer-by-layer Coated Microparticles as Cell Carriers", Advanced Functional Materials, Sep. 1, 2008, p. 2716-2723.

UniProtKB/TrEMBL, "A0A1G4WF58_9FIRM", Nov. 22, 2017, rerieved from Internet: https://www.uniprot.org/uniprot/A0A_1G4WF58.txt, pp. 1-3.

Natsume, et al., "Conditional Degrons for Controlling Protein Expression at the Protein Level", Annual Review of Genetics, vol. 51, 2017, doi.org/10.1146/annurev-genet-120116-024656, p. 83-104.

Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.

Price, et al., "Expanding and understanding the CRISPR toolbox for Bacillus subtilis with MAD7 and dMAD7", Biotechnology and Bioengineering, Feb. 19, 2020, doi:10.1002/bit.27312 p. 1805-1816.

International Search Report and Written Opinion for International Application No. PCT/US21/43534, dated Nov. 10, 2021, p. 1-16.

International Search Report and Written Opinion for International Application No. PCT/US20/26095, dated Jul. 17, 2020, p. 1-10.

\* cited by examiner

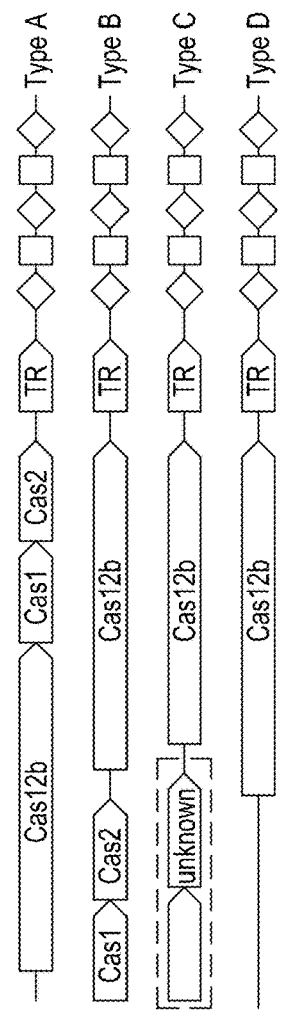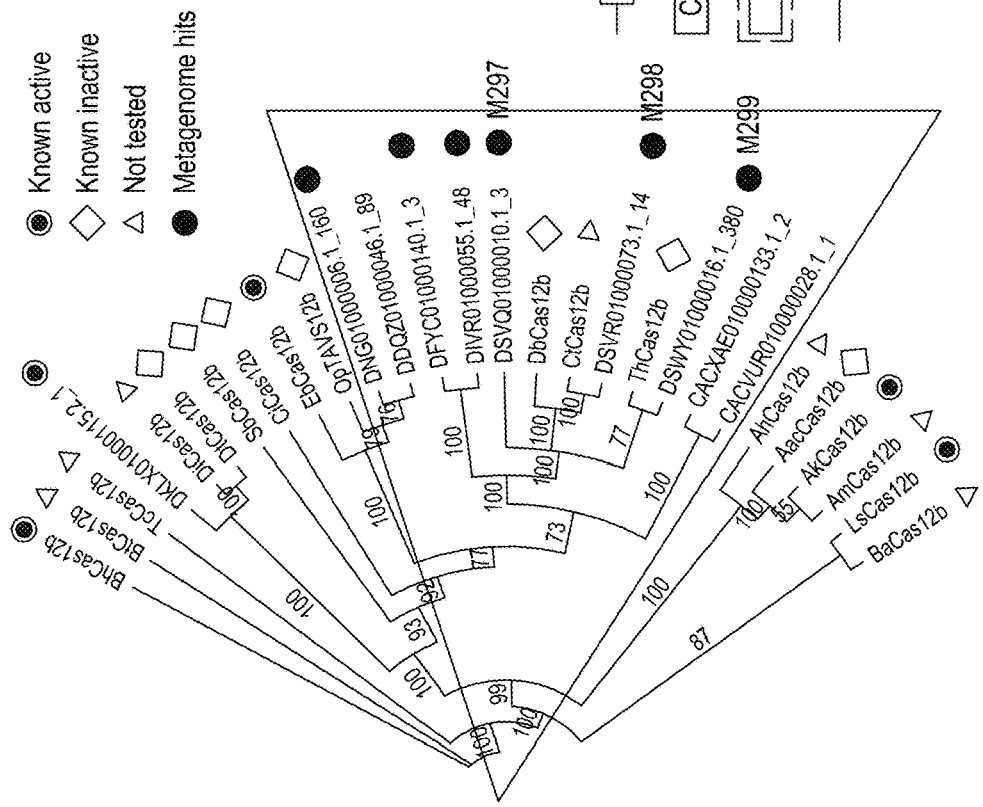
FIG. 4

| enzyme | sgRNA | length | spacer to sgRNA | PAM to spacer | Test PAM | Cut to PAM (expected) | Nickase | In vitro activity | Size (AA) |
|---|---|---|---|---|---|---|---|---|---|
| MAD297 | v3 | 82 | 3'-end | 5'-end | TTN | Distal | Natural, kinetic | Low | 1500 |
| MAD298 | v3 | 93 | 3'-end | 5'-end | TTN | Distal | Natural, kinetic | Medium | 1478 |
| MAD299 | v3 | 108 | 3'-end | 5'-end | TTN | Distal | Natural, kinetic | High | 1481 |

MAD NUCLEASES

RELATED CASES

This application claims priority to U.S. Ser. No. 63/134,938, filed 7 Jan. 2021, entitled "MAD NUCLEASES", which is incorporated by reference in its entirety.

FIELD OF THE INVENTION

This invention relates to new Type V nucleic acid-guided nucleases for making rational, directed edits to live cells.

INCORPORATION BY REFERENCE

Submitted with the present application is an electronically filed sequence listing via EFS-Web as an ASCII formatted sequence listing, entitled "INSC084US_seq_list_20211229", created Dec. 29, 2021, and 99,000 bytes in size. The sequence listing is part of the specification filed herewith and is incorporated by reference in its entirety.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow manipulation of gene sequence; hence, gene function. These nucleases include nucleic acid-guided nucleases. The range of target sequences that nucleic acid-guided nucleases can recognize, however, is constrained by the need for a specific PAM to be located near the desired target sequence. PAMs are short nucleotide sequences recognized by a gRNA/nuclease complex where this complex directs editing of the target sequence. The precise PAM sequence and PAM length requirements for different nucleic acid-guided nucleases vary; however, PAMs typically are 2-7 base-pair sequences adjacent or in proximity to the target sequence and, depending on the nuclease, can be 5' or 3' to the target sequence. Engineering nucleic acid-guided nucleases or mining for new nucleic acid-guided nucleases may provide nucleases with altered PAM preferences and/or altered activity at different temperatures or fidelity, and/or varied nuclease activities; all changes that may increase the versatility of a nucleic acid-guided nuclease for certain editing tasks.

There is thus a need in the art of nucleic acid-guided nuclease gene editing for novel nucleases with varied properties. The novel MAD nucleases described herein satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides Type V MAD nucleases (e.g., RNA-guided nucleases or RGNs) with varied PAM preferences, and/or varied activity in mammalian cells.

Thus, in one embodiment there are provided Type V MAD nuclease systems that perform nucleic acid-guided nuclease editing including a MAD293 system comprising SEQ ID NOs: 1 (MAD293 nuclease), 2 (CRISPR RNA) and 3 (trans-activating crispr RNA); a MAD294 system comprising SEQ ID NOs: 4 (MAD294 nuclease), 5 (CRISPR RNA) and 6 (trans-activating crispr RNA); a MAD295 system comprising SEQ ID NOs: 7 (MAD295 nuclease), 8 (CRISPR RNA) and 9 (trans-activating crispr RNA); a MAD296 system comprising SEQ ID NOs: 10 (MAD296 nuclease), 11 (CRISPR RNA) and 12 (trans-activating crispr RNA); a MAD297 system comprising SEQ ID NOs: 13 (MAD297 nuclease), 14 (CRISPR RNA) and 15 (trans-activating crispr RNA); a MAD298 system comprising SEQ ID NOs: 16 (MAD298 nuclease), 17 (CRISPR RNA) and 18 (trans-activating crispr RNA); and a MAD299 system comprising SEQ ID NOs: 19 (MAD299 nuclease), 20 (CRISPR RNA) and 21 (trans-activating crispr RNA). In some aspects, the MAD system components are delivered as sequences to be transcribed (in the case of the gRNA components) and transcribed and translated (in the case of the MAD nuclease), and in some aspects, the coding sequence for the MAD nuclease and the gRNA component sequences are on the same vector. In other aspects, the coding sequence for the MAD nuclease and the gRNA component sequences are on a different vector and in some aspects, the gRNA component sequences are located in an editing cassette which also comprises a donor DNA (e.g., homology arm). In other aspects, the MAD nuclease is delivered to the cells as a peptide or the MAD nuclease and gRNA components are delivered to the cells as a ribonuclease complex.

These aspects and other features and advantages of the invention are described below in more detail.

BRIEF DESCRIPTION OF THE FIGURES

FIG. 4 is a cluster map of Type V MADzymes and the structures of various types of Cas12a nucleases.

FIG. 6 is a table summarizing parameters of the three active Type V MADzymes identified herein.

Figure 1:
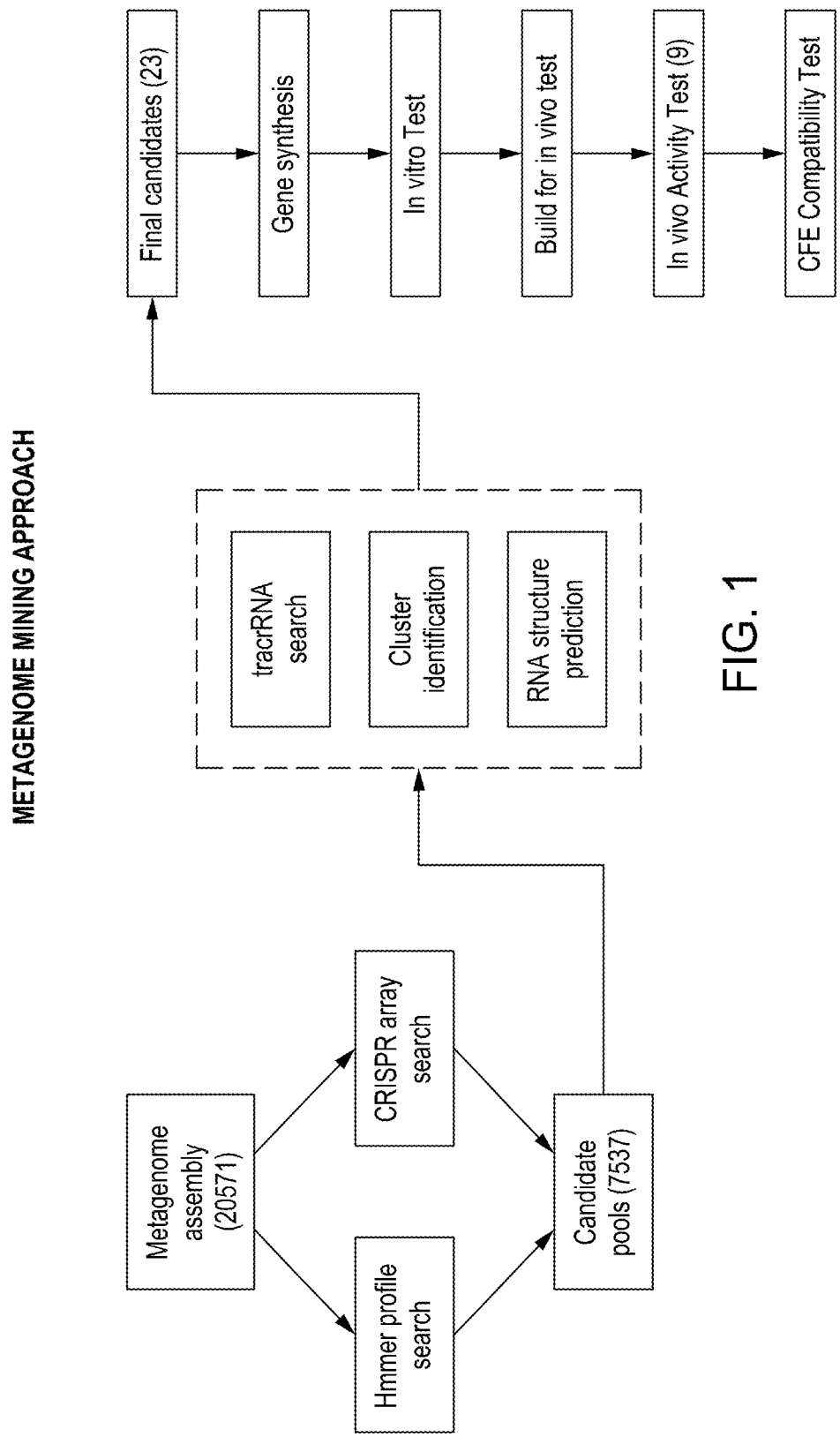
FIG. 1 is an exemplary workflow for creating and screening mined MAD nucleases or RGNs.

It should be understood that the drawings are not necessarily to scale.

DETAILED DESCRIPTION

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, biological emulsion generation, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), Lehninger, *Principles of Biochemistry* 3$^{rd}$ Ed., W. H. Freeman Pub., New York, N.Y.; Berg et al. (2002) *Biochemistry*, 5$^{th}$ Ed., W.H. Freeman Pub., New York, N.Y.; *Cell and Tissue Culture: Laboratory Procedures in Biotechnology* (Doyle & Griffiths, eds., John Wiley & Sons 1998), all of which are herein incorporated in their entirety by reference for all purposes. Nuclease-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes. Basic methods for enzyme engineering may be found in, *Enzyme Engineering Methods and Protocols*, Samuelson, ed., 2013; *Protein Engineering*, Kaumaya, ed., (2012); and Kaur and Sharma, "*Directed Evolution: An Approach to Engineer Enzymes*", Crit. Rev. Biotechnology, 26:165-69 (2006).

Note that as used herein and in the appended claims, the singular forms "a," "an," and "the" include plural referents unless the context clearly dictates otherwise. Thus, for example, reference to "an oligonucleotide" refers to one or more oligonucleotides. Terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible and, in some embodiments—particularly many embodiments in which selection is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, the contents of the engine vector may be found on the editing vector. Further, the engine and editing vectors comprise control sequences operably linked to, e.g., the nuclease coding sequence, recombineering system coding sequences (if present), donor nucleic acid, guide nucleic acid, and selectable marker(s).

Editing in Nucleic Acid-Guided Nuclease Genome Systems

RNA-guided nucleases (RGNs) have rapidly become the foundational tools for genome engineering of prokaryotes and eukaryotes. Clustered Rapidly Interspaced Short Palindromic Repeats (CRISPR) systems are an adaptive immunity system which protect prokaryotes against mobile genetic elements (MGEs). RGNs are a major part of this defense system because they identify and destroy MGEs. RGNs can be repurposed for genome editing in various organisms by reprogramming the CRISPR RNA (crRNA) that guides the RGN to a specific target DNA. A number of different RGNs have been identified to date for various applications; however, there are various properties that make some RGNs more desirable than others for specific applications. RGNs can be used for creating specific double strand breaks (DSBs), specific nicks of one strand of DNA, or guide another moiety to a specific DNA sequence.

The ability of an RGN to specifically target any genomic sequence is perhaps the most desirable feature of RGNs; however, RGNs can only access their desired target if the target DNA also contains a short motif called PAM (protospacer adjacent motif) that is specific for every RGN. Type V RGNs such as MAD7, AsCas12a and LbCas12a tend to access DNA targets that contain YTTN/TTTN on the 5' end whereas type II RGNs—such as the MADzymes disclosed herein—target DNA sequences containing a specific short motif on the 3' end. An example well known in the art for a type II RGN is SpCas9 which requires an NGG on the 3' end of the target DNA. Type II RGNs, unlike type V RGNS, require a transactivating RNA (tracrRNA) in addition to a crRNA for optimal function. Compared to type V RGNs, the type II RGNs create a double-strand break closer to the PAM sequence, which is highly desirable for precise genome editing applications.

A number of type II RGNs have been discovered so far; however, their use in widespread applications is limited by restrictive PAMs. For example, the PAM of SpCas9 occurs less frequently in AT-rich regions of the genome. New type II RGNs with new and less restrictive PAMs are beneficial for the field. Further, not all type II nucleases are active in multiple organisms. For example, a number of RGNs have been discussed in the scientific literature but only a few have been demonstrated to be active in vitro and fewer still are active in cells, particularly in mammalian cells. The present disclosure identifies multiple type II RGNs that have novel PAMs and are active in mammalian cells.

In performing nucleic acid-guided nuclease editing, the type II RGNs or MADzymes may be delivered to cells to be edited as a polypeptide; alternatively, a polynucleotide sequence encoding the MADzyme are transformed or transfected into the cells to be edited. The polynucleotide sequence encoding the MADzyme may be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of the MADzyme to be employed depends on many factors, such as what type of edit is to be made in the target sequence and whether an appropriate PAM is located close to the desired target sequence. The MADzyme may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as an inducible promoter controlling transcription of the guide nucleic acid; that is, a separate inducible promoter may drive the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

In general, a guide nucleic acid (e.g., gRNA) complexes with a compatible nucleic acid-guided nuclease and can then hybridize with a target sequence, thereby directing the nuclease to the target sequence. With the type II MADzymes described herein, the nucleic acid-guided nuclease editing system uses two separate guide nucleic acid components that combine and function as a guide nucleic acid; that is, a CRISPR RNA (crRNA) and a transactivating CRISPR RNA (tracrRNA). The gRNA may be encoded by a DNA sequence on a polynucleotide molecule such as a plasmid, linear construct, or the coding sequence may reside within an editing cassette and is under the control of a constitutive promoter, or, in some embodiments, an inducible promoter as described below.

A guide nucleic acid comprises a guide polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the components of the guide nucleic acid is provided as a sequence to be expressed from a plasmid or vector and comprises both the guide sequence and the scaffold sequence as a single transcript under the control of a promoter, and in some embodiments, an inducible promoter. In general, to generate an edit in a target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve fidelity, or decrease fidelity. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

As mentioned previously, the range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because the mined MAD nucleases disclosed herein may recognize different PAMs, the mined MAD nucleases increase the number of target sequences that can be targeted for editing; that is, mined MAD nucleases decrease the regions of "PAM deserts" in the genome. Thus, the mined MAD nucleases expand the scope of target sequences that may be edited by increasing the number (variety) of PAM sequences recognized. Moreover, cocktails of mined MAD nucleases may be delivered to cells such that target sequences adjacent to several different PAMs may be edited in a single editing run.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). For cassettes of this type, see U.S. Pat. Nos. 10,240,167; 10,266,849; 9,982,278; 10,351,877; 10,364,442; 10,435,715; and 10,465,207. The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments the promoter driving transcription of the gRNA and the donor nucleic acid (or driving more than one gRNA/donor nucleic acid pair) is an inducible promoter. Inducible editing is advantageous in that isolated cells can be grown for several to many cell doublings to establish colonies before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells. See, e.g., U.S. Pat. Nos. 10,533,152; 10,550,363; 10,532,324; 10,550,363; 10,633,626; 10,633,627; 10,647,958; 10,760,043; 10,723,995; 10,801,008; and 10,851,339. Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes one or more nuclear localization sequences (NLSs), such as about or more than about 1, 2, 3, 4, 5, 6, 7, 8, 9, 10, or more NLSs. In some embodiments, the nuclease comprises NLSs at or near the amino-terminus of the MADzyme, NLSs at or near the carboxy-terminus of the MADzyme, or a combination.

The engine and editing vectors comprise control sequences operably linked to the component sequences to be transcribed. As stated above, the promoters driving transcription of one or more components of the mined MAD nuclease editing system may be inducible, and an inducible system is likely employed if selection is to be performed. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8): 3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

Typically, performing genome editing in live cells entails transforming cells with the components necessary to perform nucleic acid-guided nuclease editing. For example, the cells may be transformed simultaneously with separate engine and editing vectors; the cells may already be expressing the mined MAD nuclease (e.g., the cells may have already been transformed with an engine vector or the coding sequence for the mined MAD nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a host cell. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Pat. Nos. 10,435,713; 10,443,074; 10,323,258; and 10,415,058.

After the cells are transformed with the components necessary to perform nucleic acid-guided nuclease editing, the cells are cultured under conditions that promote editing. For example, if constitutive promoters are used to drive transcription of the mined MAD nucleases and/or gRNA, the transformed cells need only be cultured in a typical culture medium under typical conditions (e.g., temperature, $CO_2$ atmosphere, etc.) Alternatively, if editing is inducible—by, e.g., activating inducible promoters that control transcription of one or more of the components needed for nucleic acid-guided nuclease editing, such as, e.g., transcription of the gRNA, donor DNA, nuclease, or, in the case of bacteria, a recombineering system—the cells are subjected to inducing conditions.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Exemplary Workflow Overview

Figure 2:
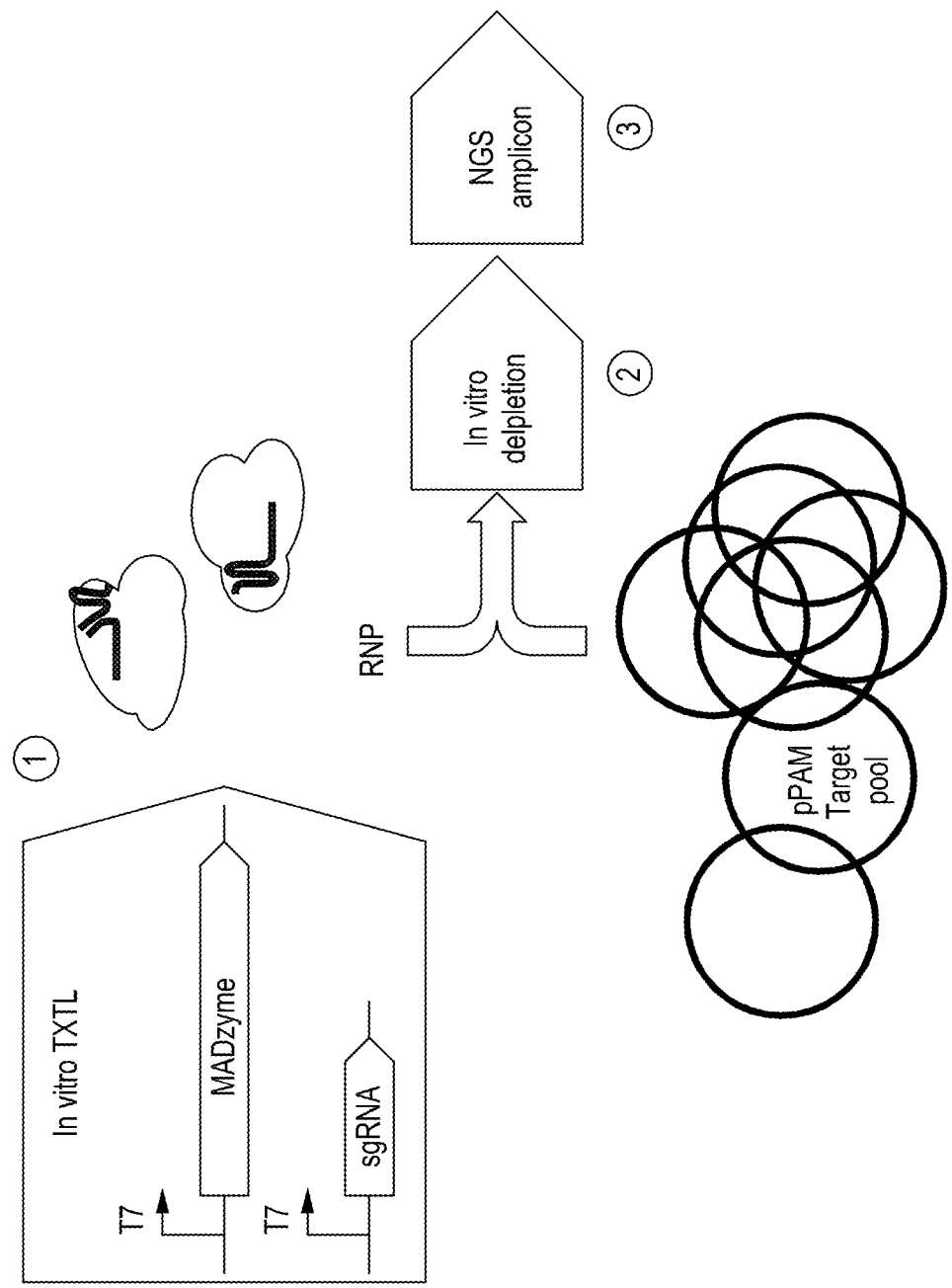
FIG. 2 is a simplified depiction of an in vitro test conducted on candidate enzymes.
Figure 3:
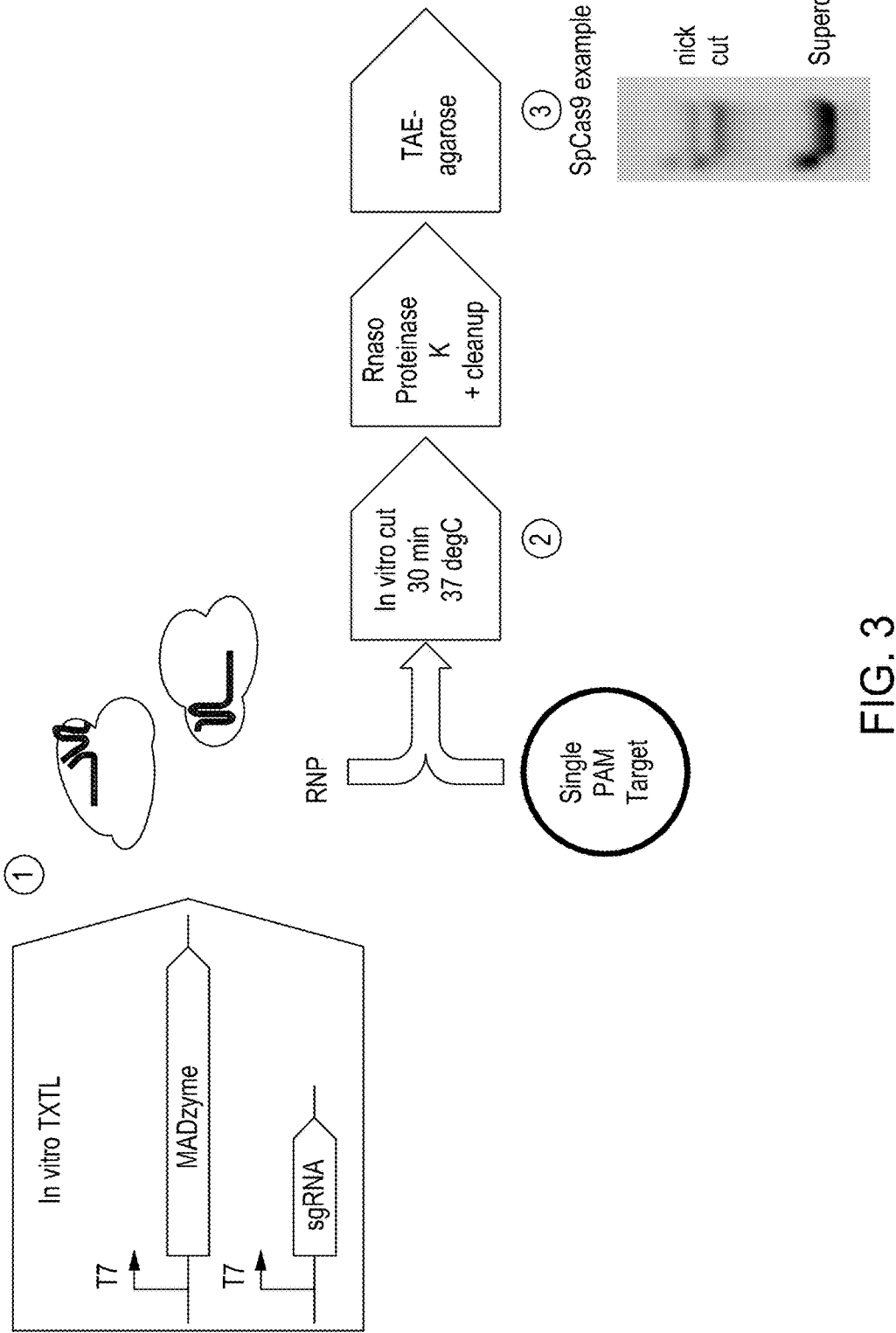
FIG. 3 is a simplified depiction of an in vitro nick assay.

The disclosed MADzyme Type V CRISPR enzymes were identified by the method depicted in FIG. 1. FIG. 1 shows an exemplary workflow for creating and for in vitro screening of MADzymes, including those in untapped clusters. In a first step, metagenome mining was performed to identify putative RGNs of interest based on, e.g., sequence (HMMER profile) and a search for CRISPR arrays. Once putative RGNs of interest were identified in silico, candidate pools were created and each MADzyme was identified by cluster, the tracrRNA was identified, and the sgRNA structure was predicted. Final candidates were identified, then the genes were synthesized. An in vitro depletion test was performed (see FIG. 2), where a synthetic target library was constructed in which to test target depletion for each of the candidate MADzymes. After target depletion, amplicons were produced for analysis by next generation sequencing. FIG. 2 depicts the in vitro depletion test in more detail. FIG. 3 depicts the in vitro plasmid nick assay performed.

Example 2: Metagenome Mining

The NCBI Metagenome database was used to search for novel, putative CRISPR nucleases using HMMER hidden Markov model searches. Hundreds of potential nucleases were identified. For each potential nuclease candidate, putative CRISPR arrays were identified and CRISPR repeat and anitirepeats were identified. Seven nucleases were chosen for in vitro validation and three active MADzymes were identified. The Type V cluster is shown in FIG. 4. MAD297, MAD298 and MAD299 were found to be active. The table in FIG. 4 gives some parameters for the seven nucleases chosen, and the structures of the Cas12a types (A, B, C and D) are shown below the table. Table 1 below lists the identified MADzymes, including amino acid sequences and the nucleic acid sequences of the CRISPR RNA and the trans-activating crispr RNA.

TABLE 1

| MAD name | Contig_id | aa_seq | CRISPR repeat | tracrRNA |
|---|---|---|---|---|
| MAD293 | DFYC010 00140.1 | MAAFQRSYTMNLKPATSEQDKFILWNRLFLTHWSVNEGAK IFGELFLNLRGGLSPELDIFDLDKVKDDKKKKAFVMGRRLLA LGWLSVEDNLSAGEHPFRIREIPVGRNMGKSQASTLLTEILK NKGKDEAVIKEWIDDCTPSLIANIREDAVWINRASSFNSITP CPTKDEVWIVLSGLLGLRFLDLSLEEVKGKETEYLYDLGKET QSKSDPSKKARELFGNLFTQNPVLMKNSRDKKDTFAKEFYL AFKEFKDYEKLKEKIESWRKEKEFPLIENPVAEKYPPEVTFTGS PCTVSKRYRKLLVSLELWPSSQDENGNIPKTEKTEDKTHNQV LLDYLLKACNEGNKGTQKIITPVWANNLKAELELKMNE1lRIG ESSSTELQRLMIKMAARRISQTLSWIKINEQTKHDAYQKKNK AFKLLSEIDKNGEACKWLENYELFRTDDSGGEEYHISLRAISC WKQILEEWQKNDSPKALREKVKEVQAEEEKFGDARLFEDLA DDNARSVWLLPDGNKTPDILNWWCEYRTAEIDESRFKIPCY CHPHPFKHPVYVEYGKSNPKVIFAMKNNKVKKGHIEHGWN PONPRSIALSLFNNGNRESSLVPFIWESKRLWKDLGGEATQI GDIPRSDRMGLSGKRESVKPKAPFQKEVWNARLQSDRRTLE KLEMMPESMKWIDDGKFLIQSKWFITFGPDMETAEGPW KLYLKEKYVDNKILGNRSKENQKRGYRAKKLLSGYPAGMRIL SVDLGHRYAASCAVWETITKKQITEELAYQPDNNSLFEHSCK TIDKKIKNTVYRRIGEDSIDAPWAKLEKQFTIKLQGEDKSCYLL RSDEKELFRSILSKLSCLNNDTGHNILEMIENLLRIVKAKIYRQ GILARISYSMTAQYKPGKGGQKSPLSDEDKIHYLSENLAAWS AIMGNQEWNEDVISDWYKTYISHLVSGPKPKEGNRKSDRD KIIEYFLPAARKLYDDNETRIKIHDLFKELWDENNKQLSAVLKE IKKIILPKGIRYFDKNTDNPSKWKNNQSKLKQITHRGGLSMQ RIVAIEEYYKLAKAYKNHPEPDDLTKNIPLPGDNSSAGFNQRI RDTLERMKEQRVKQIASRIVESALGLGIEGYKKRPLTPENKPC QAIVIEDLSHYRPDELQTRRENRRLMQWSSSKVKKYLKEACE MHDVRLVEISPEYTSRQDSRTGAAGLRCIDINIREFLKDSSR WQNKINTIQKKPANKKSNLDQYLIELNESLGNKYKDKVIPSD NFVRIPRKGGDVFVSSSKESPVSKGIQADLNAAANIGLKALL DPDWAGAWWYILIEVKSNHVIPYGEKYKGSECLRAWKFSGL ENQVMKNNMNLWRDLQSQFSGEDKWMSYKEYNELTEKR VINILRERAGLELIKE [SEQ ID NO: 1] | GTTTAAGTAGA TACTACTGAAA AGACCGATGG ACACA [SEQ ID NO: 2] | GGGAAGGGCC TATTTCCCAGC ATGTGTCTTCG CATTTAATTGC TTTAGCACTGG GCATCGTTCTT TTTAGTAGT [SEQ ID NO: 3] |
| MAD294 | DIVG010 00006.1 | MNRIYQGRVSKIE1KDSEGNFRNVPVGSPDTCPLWRHHRIF QDAVNYYLVALGALAGTGSENAFVGLGSKDRVIHDLYSRLF DSWERFPRDMHGASSLRDSLRRTLPGLSERASLQDAFDAILS GNEANARERVLSLLSLIQDLGGDIQKGSKRYFPFFCEPATKAT FPPRARVGLLKVEGKDFVPRLLWSSDLEIAPDQVVEQLKFEYF ANPNESVQPIEGNEARVRLIEALDNPQLGIELPIE1LSDLRKV HLIETDIRIPRYFFGGAGAELRKFRLDLFLIAAYVTPDPSILRAL RNSFKEPSASKSSKKKDETEEVENLLRSLGDDPLILARGERGF VFPSFTSLPTWVGANAQKPIWRDFDIAAFAEALKSLNQFTA KTEEREEKLKKAEETLHYMLGISDAIPRSSDSETEEQAPSRPG KDPRWPLVAQLEKELGENLSEGTWQLSRSAMRGLRDIIGL WRKHPGASVVTLQKDVKTYQADEKHKREIGSVQLFLLLCEE RYHALWQTETDDERGDESEENDDPARILSDAIEVHQIRREVE RFREPIRLTPAEPVFSRRLFMFSDLTDKLAKVKFGETTEENSE VKSQFVEAAIALKEGENLKEARVRITFSAPRLHRDELLGGAES RWLQPITAALGFSNPAPSVKFDSAVALMPDHMDDGRIRHL LNFPVNFDSAWLHQSIGKADLWKSQFNGTKDKNLHLHWA GTARDTTRKNTWWENRTIIENGFTVLSNDLGQRSAGAWAL LKVTCSRPDTKHPVRSIGHDGTREWFATVLATGIHRLPGED QRILKNGKWATEQSGKKGRNATFSEYEAACVLAKNLGCESV ENWLGMSGEKSYPALNDQLVKIANRRITRLGTYHRWSCFSP EKFEDPARRANVIGGQLAELSAYQDENVTVSADILKSGDFEG FRHRAGAAFEALRTELEVHLVNLANLTAPLRQKVWSWQKR PDSSGYGDLLMVDLDDCHPKIRGQRGLSMARLEQLEGLRRL FLRYNRSLDRSPGIPAKFGREDVGRTSGEPCQALLVKIDRMK EQRVNQTAHLILAQALGVRLCPHRIEENERKSRDLHGEYEKI PGREPVDFIVIEDLSRYLSSQGRAPSENSRLMKWAHRAVRD KLKMLAEEPFGIPVVETVPAYSSRFHALNGQAGSRLHELHEL EAYQQQSLINLAAKTDFQNRDRSKAAGELFEFQFQALAKLNE RRRAEGKKVPRTLYYPKSGGPLFLASRDGDTIHADVNAAINL GLRAIAAPACIDIHRRLRATKEKEVYRPVGNAREKSAFSKDD IIQPSGAPSKKFASSSSPNFFYEPEDLKQANGEPLFDRAMFG EYSLVSGVSLWSMVNNAIYIRCVELNRTRLHGKDPDDQIPM [SEQ ID NO: 4] | GCCGCAGCCCC CGCGATGGGA AAGAGATTGT GGCGG [SEQ ID NO: 5] | GCCCCGATTTC CCTTTGAATGA TCTCGGCCTCG TTGCCACTGAC CGAATTCTTCC GCCTTTGGAAT TCCAAGCTCTT TGACATCGCGA GCGCTGAGG [SEQ ID NO: 6] |
| MAD295 | DIVR010 00055.1 | MAAFQRSYTMNLKPATSEQDKFILWNRLFLTHWSVNEGAK IFGELFLNLRGGLSPELGIFDLNKDKDDRKKKALVMGRRLLA LGWLSVEDNLSAGDHPFRIREIPVGRNMEIKQATTLLTEILKN KGVKDEAVIKEWIDDCTPSLIANIREDAVWINRAKSFYSMNP CPTKDEVWKILSYVLNTSFLDLSLNDSSERDNTKNKKGTKEN EKDVSNKSKELYGWLFTKNPNKMREAGENKDKFINNFRENF | GTTTAAGTAGA TACTACTAAAA AGACCGATGG ACAC [SEQ ID NO: 8] | GGGAAGGGCC TATTTCCCAGC ATGTGTCTTCG CATTTAATTGC TTTAGCACTGG GCATCGTTCTT |

TABLE 1-continued

| MAD name | Contig_id | aa_seq | CRISPR repeat | tracrRNA |
|---|---|---|---|---|
| | | NTFTDYANLKVEIELWRKNNISNTLLITQKAKYPPEVKEANH PSKFSVGYRKLLVHLELWPSSKDENGDIPKGIEGKDKSHNQIL LDYLLEVCNEGNKTTKKVIVPAWADGIKTELESKASIKVGDST SSVLQRLMIKMAARRISQTLSWIKINEQVRHDAYQKKNKAF KLLCEIDKNGEACKWLENYELFRRDDSGGEEYHISARAISCW KQILEEWQKNDSSKALREKVKVVQAAEDKFGDARLFEDLAD DNARSVWLLPDGNKTPDILNWWCEYRTADIDESRFKIPCYC HPHPFKHPVYVEYGKSNPQVIFSLKHDKARKNRIDNGWNPK NPRILALLLLDIVRQKSTLAPFVWESKRLWKDLGGDATVTYKI PRSDRMGLSSIGNIDYARPEVPFLKEKWNARLQSDRRTLEKL EK1ANNPESMKWIDDGKFLIQSKWFITFGPDMETAEGPWKL YLKENINDNNYLGNRSKENQKRGYRAKKLLSGYPAGMRILS VDLGHRYAASCAIWETITKKQITEELAYQPDKNSVFEHSCKTI DKKIKNTVYRRIGDDSIDAPWAKLEKQFTIKLQGEDKSCYLLR SDEKELFRSILSKLSCLNNDTGHNILEMIENLLRIVKAKIYRQGI LARISYSMTAQYKPGKGGQKSPLSDEDKIHYLSENLAAWSAL MGNQEWNEDGISDWYKKYISHLVSGPKPKEGNRKSDRDKII EYFLPAARKLYDDNETRINIHDLFKELWDENNKQLSAVLKEIK KIILPKGIRYFDKNNDSSSRWKNNQSKLKQITHRGGLSLRRIV AIEGYYKLAKAYKNHPEPDNLTKNIPLPGDNSSAGFNQRIRD TLERMKEQRVKQIASRIVESALGLGIEGYKKRPLTPESKPCQA IVIEDLSHYRPDELQTRRENRRLMQWSSSKVKKYLSEACEM HDVLLVEISPEYTSRQDSRTGVAGLRCIDINIREFLKDSSSWQ NKIKTIQMKPTNKKSNLDQYLIELNESLGERYKDKVIPSDKFV RIPRKGGDIFVSSSKESPVSKGIQADLNAAANIGLKALLDPD WAGAWWYILIEAKSNHVIPYGKKYKGAECLRDFKFSGLENQ VMKNNMNLWRDLQSQFSSEDKWMSYKEYNELTEKRVINIL RERAGLELIEE [SEQ ID NO: 7] | | TTTAGTAGT [SEQ ID NO: 9] |
| MAD296 | DKLX010 00115.1 | MVTRALNLKLVVPRRPGELTKAEALWSTHDIVNRATSYYES QLLLCRQQDYQTRELTVSAGDQAPDLDALIANARDRNRYRG LEKPQVVREKLRNLYEAIVPPAIGKTGTAQAVGAFVSPLLDA DSRGFTEIFDKIEALPNWVDGVRAEEPDALEAAADWLKSPQ GKERLRPTGAPPTWIKLAKKKDAGWAAAFVADIDKKLKVE GTPTLMQELRALGVMPLFPSFFASRIAGHKGAVSTWDRLAL RLAVAHLLSWESWVELAAKEHAARVAKLEKFRDDNILGEIA DAVEALRLYEKERTEELQQKAQLDAEEVRTTSRTIRGWVDLR EKWLKTDASPDALISLVAAEQKRKSGKFGDPQLFRWLAKPE NHFVWNKPDFDPPSLFASLRMIEGLVERSKETAWMTLPDA RLHPRSSQWEPHGGGNLKTFRLEQGEGGSLSVTLPLLRKSG DDSYVEEEHAFSLAGSKQIPNASLDVRRNKYCLSYRTPTGEE AEAVVGSADLLLLDWYFLQQRSEHRPEEGDIGPAFLKLALDIT PIDPVWGEREKTPAIHHFKTASGKNTRHADGVAPGFRMLA VDLGIRTLATCSVFELKATAPAGRLSFPIAHLDLHAVHERSFTL TLDGEPDRDAERWRENKSAELRRLRMGLTRYRNIRNMRE DAPDEREVLLEDLQEKVQEHGWAFEEPLLRELAKHKDTPEPI WEAELTKALAQFRSDFGVIVGEWRRSNRARSTDSHAGKSM WAIDHLTNSRRFLMSWSLLSKPGQIRRLDRDKQGVFAKHLL DHLEGLKADRLKTGSDLIVQAARGFRRDKRGNWHKAYKPC HGILFEDLSRYRMRTDRPRRENSQLMKWAHRAVPKEVGM QAEVYGIRVEDTGAAFSSRFHAASHTPGIRMHPICQKDLEN EWLLDEIEKQNSGVKRRELKLGQLVQLNGGELFACVTASGV KTLHADINAAQNLQRRFFTRHGDAFRIVARKVLVDEEEVWV PRSLGKRLLGALGSHGKLVPTGHESGSCRFEEITTRAWSKLS GEKLSDDRVGNEEDQIIASIEEEALERTGEVVVFFRDPSGQVL PRDLWYPSKTFWSIVKSTTLSKLKAAP [SEQ ID NO: 10] | GGTGAAGTCA CCCCCGTTTTG TAGGGCCTACTG GCAC [SEQ ID NO: 11] | ATGTAACCCTA TAGGGGTTGC GTGAGTCGGC CATAGTGCCTC GGCAACAGCG TAAAAAACTGC TGCCAGTGGTC GAAGTAAGTC AACAAAACGG AGGT [SEQ ID NO: 12] |
| MAD297 | DSVQ010 00010.1 | MATAINYPTTQRAYTLRLRGIDPQDQSWRDALWATHEAVN RGAKVFGEWLLTLRGGLDHQLADAPVKVRGGTTRLPSDEER RDRRVLLALSWLSVEDAHGAPPDASLIVAKGTDSADCRAKR LADALIAILQARSVAAESEIGDPSKPPEDQPGTWLGDCMGSLS AAIRDDAVWVNRSKAFDAATQSCPSLTRDEIWDFLEPFFAS PDAYLKPERAESDEGDSTSAATEDKAKDLVQKAGGWLSKR MGAGGGANFQDLARAYQAIAQWASSAQPGQSAQQAVGS LAGYLSQHGFSPTANDATGVLAVISGPGYKSATRNHITAIATS PEITPQDLSKLQELATKDKAGCSSKIGGKGPRPYATMILQQV EAACGFTYLQSDGPARHREFSVMLDHAARRVNVAHSWIKN AEAERRQFESDARRIKKVPQDALNWLRGYCEERGGASGSLE GYRIRRRAIDGWDQVIRWSRSDCQSADDRIAAARQLQDD PEIDKFGDIQLFEALAAEEALCVWKPDGNPTAQPLRHPVFT DFGNSRWGIEYSAHR APAKCDELGQQVDRLTQVAEAQRNLDGATAAQRASRESK LAEAQSKLVAAQTEFAAINDPHRVELKLWNGQAVAAIPMR WSSKRLIADLSLRRATQPSSDQRIGVTRADRLGRAAGNADD GRPVTIGLFQQDHWNGRLQAPRAQLDAIAKHVDKHGWD | GGCGGCGAAT TCGCCGGCATC TCGATCGACCG ACAC [SEQ ID NO: 14] | CGGAGGGAAC TCCGTGAACGT GTCTTCCCCTT CGATGGGCTT GGCACACGGG GTCAATCGAGT TGCCGTTGAA [SEQ ID NO: 15] |

TABLE 1-continued

| MAD name | Contig_id | aa_seq | CRISPR repeat | tracrRNA |
|---|---|---|---|---|
| | | AKARRQIARIRWVVSFSAELSQQGPWFEFCHRFGEDAPARP FVSRHGEYAVKHRDNDQRKGHAKLILSRLPGLRVLAVDLGH RYAAACAVWEAISSDQMRQACAAANAPAPHPLAMYIHLKS TTAKGKPTTTIYRRIGPDKLPDGTPHPAPWARLDRQFLIKLP GEDRPARAASPDEIKAVEDFEDSVGRVRTAVDPPRKRGVDL LMHDAVRTARLALARHGRRARIAFQLISQVRILPGGRPQTLD DAGRRDLLNDTLADWYALATDSRWTDAAARQLWNERLAA LNGGFTIDPPADASQPEAERTRAQRRQAEQELRHRLASLVE ALFCNPTLCQQLHQAWTDRWNADDQQWRSRLKWLSRW LLPRGGSRRDGSRRHVGGLSLTRISTLIDFRRKVQVGYFTRLR PDGSRAEIGPQFGQSTLDAIQRLKDQRIKQLTSRIVEAALGIG VEQDRIWDAAKRKWRTVKRPREPRYHVDDQGVQQRDPRF QACHAVVIEDLSHYRPEETRTRRENRATMDWKSAETRKRLA DHCQLYGLHLRDVNPQYTSRQDSRTGAPGCRCVDVSVADF LTKPAWRKQVAQARGKVASNRGDARDRLLVELDHQLTTAN SLRGEMDSLRIPVNGGEVFVSADPRSPLAAGIQADLNAAAN IGLRALMDPDFLGTWWYVPCDPSTKKPHIEKVKGSILATVG ALQATSEEAAPPRRGRGGTRSAAPREVINLWRDPSAVRIQ DATAGEVWDVTPVYWSIVKDRVVDVLRQRNTKSGD [SEQ ID NO: 13] | | |
| MAD298 | DSVR010 00073.1 | MSQQVKPPVTQRAYTLRLRGIDPSDTSWRKALWQTHEGV NKGAKAFGDWLLTLRGGLDHTLADTKVKGGKGKPDRDPTD EERKARRILLALSWLSVESKLGAPVGFIIASGTEAAEDRNRKV VAALEE1LKSRNVATNE1DQWKNDCSASLSAAIRDDAVWVN RSKAFDEAVKSIGSSLTREEAWDMLERFFGSRDAYLAPAKGS EDESSETEQEDKAKDLVQKAGQWLSSRFGTGKGADFCRMA NVYGKIAAWADNAQADTTGNDAINNLAAALNEYSPEPNDL KGVLGLISGPGYKSATRNLLNQLAAKATVTQQDFVSLKDKAS NDAQKCKQNTGSKGPRPYSDAILKNVESVCGFTYLQDGGPA RHSEFAVILDHAARRVSLAHTWIKRAEAERRKFEEDAKKIDQ VPKAAKDWLDSFCLERSGASGALEPYRIRRRAVDGWKEVVA AWSKADCKTAEDRIAAARALQDDPEIDKFGDIQLFEALAED DAVCVWHKDGDAAKPPDPQPLIDYALAAEAEFKKRHFKVP AYRHPDALLHPVFCDFGNSRWDICFDVHKNVQTPFPRALSL TLWTGSGMVSVPLCWQSKRLARDLALGQNAQNDGSSEVT RADRLGRAASNVTKSDEVKISGLFEQEDWNGRLQAPRQQL EAIAAVRDNLSLSDQERERRMSGMIDRIRWLVTFSAKLQPQ GPWCEFAEKIQIGINPQYWPHADTNKDRKGHARLILSRLPG LRVLSVDLGHRYAAACAVWEAVNAEQINVACRAAGHREPK ASDLYLHLRKTTKQKKGDQVEFKETTIYRRIGADTLPDGTPH PAPWARLDRQFLIKLQGEEEGVRAASNEEIWAVHRLEVELG RTAPLIDRLVKAGWGQSGKQKTRLDALRNLGWAPANEVQ GSDEMDEGEVHKPSLSVDELMSSAVRTMRLALKRHGDRAR IAFAMTAAYKPMPGDRKYYFTEAKDASANEDATARNGKHIE FIQDALLLWYGLTSSRGWRDDAARQLWDDHIAKLSVYKAPE EIGEDASGVERKTKQENREKLHDVAKALAQDVNLRKVLHN AWKKRWEKDDERWKKQLRWFKDWVFPRGKHASDPAIRK VGGLSLPRLATLIEFRRKVQVGFFTRLQPDGTRAETKEQFGQ SALDTLEHLREQRVKQLASRIVEAALGIGRVRRPLGGKDPKR PDVRVDEPCHAIVIEDLTHYRPEETRTRRENRQLMTWSSSK VKDYLSEACQLHGLHLREVSASYTSRQDSRTGSPGIRCQDVP VKEFMRSPFWRKQVAQAEKKGDAHERFLCELNAMWKDKT VADWEKAGAVRVPLKGGEVFVSADRISPSAKGLQADLNAA ANIGLRALTDPDWPGKWWYVPCEPASFRPAKDKVDGSAV VNPGQPLRQSAQAQSGDAAKDKKKRGNKGAGQSKEVVNL WRDISSSPLECIECGEWKEYAAYQNEVQYRVIRILEEQIKGRD RQPHEGSREDDIPF [SEQ ID NO: 16] | GTTGCCGACGT CAGCACCAACC TGATCGACGG ACAC [SEQ ID NO: 17] | TTGCCTCTACA GGAGGCGAGA ATGCCACGGCA CGTGTCTTCCC CTTCAATGGGC TTGGCACCGTG GAGTCGATCA GTTTTGTGCCG GCGAAGG [SEQ ID NO: 18] |
| MAD299 | DSWY010 00016.1 | MARRSASTSKPPGPVAPTTQRAYTLRLRRAPGKCPHCEQDA CDCWREALWATHAAFNRGAKAFGDWLLTRGGLSHELAE QPSPPKNKEPTCEEESDAIRKNRRILLALSWLSVEDDCSAPTGT FRVASGKDSEAERKNKVLTAFRSILTARRMRSQDVESWIAD CAASLSAKIREDAVWINRSACFDQRALDLKVLSREYAKAAV MSFFGPLDEYFKLPDEADDTKPAVGGDGPDFRTLARQWVS TNFGTGKKSDSEAIAQNLRKLADANLAPFSGKPKAALIAHLS VELDGSTADIDGLCRAIGWNTGRPSKGRVAIERLPDPPTETSI QTMQQKFREEAEAKASSKGLRQVPEWMPAFQKSIERDCG MPFKLGEGRDHIGEFSVMLDHAARRVSIGHSWIKRAEAERR RFEADAQRLNHIPAAAKDWLDQFVQFRSGSSGAAAAGGEY RIRRRAIEGWDEIIKRWKRAACKSPEDRVAAAREVQADPEIE KFGDIQLFEALAADDAECVWRGDGNGTPDPLKDYVAATDA LDKMRRFKVPAYRHPDPLAHPVFGDFGNSRGDIRFAVHEA AKATRGTKRIAKDQKEWIRERHGLRMGLWDGQSVRTADLR WSSKRLVDDLALRNHVTTRRTGPVSRADRLGRAAAGLGAD EAACVAGLFELPDWNGRLQAPRAQLDAIAACVAANGGKW | GCCGCGTCGG CCGACGCGGC CTTGATCGATG GACAC [SEQ ID NO: 20] | GTCGCCTATAG GGCGATACAA CTCCGAGCATG TGTCTTCCCCTT CAATGGGCTTG GCACTCGGCAT CGATCAAGCTC GCGTCGGCTGT CGGGCC [SEQ ID NO: 21] |

TABLE 1-continued

| MAD name | Contig_id | aa_seq | CRISPR repeat | tracrRNA |
|---|---|---|---|---|
| | | DDKARKLRDRIEWLVSFSAKLECCGPFMEYASQNGIQPNGK GEYYPHAERNKGRTGHAKLILSRLPGLRVLAVDLGHRFAAAC AVWEALSKIAFDAETKGREVVSGGRAADDLYCHTRHLDCAG KARTTIYRRIGPDKLPDGSDHPAPWARLDRQFLIKLQGEERP ARAAGPAETAAVQQIETDLGRARGQEDLPPRPVDSLMREA VRTIRIALRRHGDAARIAYAFKPGAKRLKPGGGAQDHTPETH ADAILEALLRWHELATGARWRDPWAETQWKDWVQPHISA TLPELANDADRWERKRHRAALEQVLRPVAQMLIQRPTDAL HQVWSKHWADEDLKWPSRLRWLRNWLLPRGPRARSGAA RNVGGLSLLRIATLRELYQTQKAYAMRPEPDDPRKRIAGRN DDRYDELGRSVLQVIERLREQRVKQLASRIVEAALGVGRAKP TRGRQRPQSRVDVPCHAVIIESLRNYRPDELQTRRENRAIM NWSAGKVRKYLEEACQLHGLHLREVMPNYTSREDSRTGLP GVRCVDVPVDPKLGKPKAYWWNSVLSTARKKSIGDAASHD KQGDATSRFIVELAGCLDRLKADGKPLPKTVRVPRIGGDLFV AAPPTSCTAPAHQPHPACDGARALQADLNAAANIGLRALL DPDFPAKWWYVPCIDDQRGLALPRADKVLGSACFPGDPAT FGSLLKTRTAAGPAVDGQAAPDRKPRTGTHRPGSAKSRSLG DGKATTNYWSDRSARDLRPADEGGHWQPTNVYWNWVR KRALLGLYSFNGLSPPSDDRP [SEQ ID NO: 19] | | |

Example 3: Vector Cloning of MADZYME and PCR for In Vitro Test

The MADzyme coding sequences were cloned into a pUC57 vector with T7-promoter sequence attached to the 5'-end of the coding sequence and a T7-terminator sequence attached to the 3'-end of the coding sequence.

First, Q5 Hot Start 2× master mix reagent (NEB, Ipswich, Mass.) was used to amplify the MADzyme sequences cloned in the pUC57 vector. The forward primer 5'-TTGGGTAACGCCAGGGTTTT [SEQ ID NO: 55] and reverse primer 5'-TGTGTGGAATTGTGAGCGGA [SEQ ID NO: 56] amplified the sequences flanking the MADzyme in the pUC57 vector including the T7-promoter and T7-terminator components at the 5'- and 3'-end of the MADzymes, respectively. 1 µM primers were used in a 10 µL PCR reaction using 3.3 µL boiled cell samples as templates in 96 well PCR plates. The PCR conditions shown in Table 2 were used:

TABLE 2

| STEP | TEMPERATURE | TIME |
|---|---|---|
| DENATURATION | 98° C. | 30 SEC |
| 30 CYCLES | 98° C. | 10 SEC |
| | 66° C. | 30 SEC |
| | 72° C. | 3 MIN |
| FINAL EXTENSION | 72° C. | 2 MIN |
| HOLD | 12° C. | |

Example 4: gRNA Construction and PCR for In Vitro Test

Several functional gRNAs associated with each MADzyme was designed by truncating the 5' region, the 3' region and the repeat/anti-repeat duplex (see Table 3).

TABLE 3

| gRNA name | sgRNAv1 | sgRNAv2 | sgRNAv3 | sgRNAv4 | sgRNAv5 |
|---|---|---|---|---|---|
| sgM293 | GGGAAGGGCCTA TTTCCCAGCATGT GTCTTCGCATTTA ATTGCTTTAGCAC TGGGCATCGTTCT TTTTAGTAGTGTTT AAGTAGATACTAC TGAAAAGACCGAT GGACACA [SEQ ID NO: 22] | GGGAAGGGCCT ATTTCCCAGCAT GTGTCTTCGCATT TAATTGCTTTAGC ACTGGGCATCGT TCTTTTTAGAAAA CTACTGAAAAGA CCGATGGACACA [SEQ ID NO: 23] | GGGAAGGGCCTA TTTCCCAGCATGT GTCTTCGCATTTA ATTGCTTTAGCAC TGGGCATCGTTCT AAAAAGACCGAT GGACACA [SEQ ID NO: 24] | GGAAGGGCCTAT TTCCCAGCATGT TTCTTCGCATTTA ATTGCTTTAGCA CTGGGCATCGTT CTTTTTAGAAAA CTACTGAAAAGA CCGATGGACACA [SEQ ID NO: 25] | GGTCCAAGGGA AGGGCCTATTTC CCAGCATGTGTC TTCGCATTTAATT GCTTTAGCACTG GGCATCGTTCTTT TAGAAAACTAC TGAAAAGACCGA TGGACACA [SEQ ID NO: 26] |
| sg M294 | GCCCCGATTTCCC TTTGAATGATCTC GGCCTCGTTGCCA CTGACCGAATTCT TCCGCCTTTGGAA TTCCAAGCTCTTT GACATCGCGAGCC CGCGATGGGAAA GAGATTGTGGCG G [SEQ ID NO:27] | GCCCCGATTTCC CTTTGAATGATCT CGGCCTCGTTGC CACTGACCGAAT TCTTCCGCCTTTG GAATTCCAAGCT CTTTGACATCGC GAGCCCGCGATG GGAAAGAGATT GTGGC [SEQ ID NO: 28] | GATTTCCCTTTGA ATGATCTCGGCCT CGTTGCCACTGAC CGAATTCTTCCGC CTTTGGAATTCCA AGCTCTTTGACAT CGCGAGCCCGCG ATGGGAAAGAGA TTGTGGCGG [SEQ ID NO: 29] | GGATTTCCCTTTG AATGATCTCGGC CTCGTTGCCACT GACCGAATTCTT CCGCCTTTGGAA TTCCAAGCTCTTT GACATCGCGAGC CCGCGATGGGAA AGAGATTGTGGC GG [SEQ ID NO: 30] | NONE |

TABLE 3-continued

| gRNA name | sgRNAv1 | sgRNAv2 | sgRNAv3 | sgRNAv4 | sgRNAv5 |
|---|---|---|---|---|---|
| sg M295 | GGGAAGGGCCTA TTTCCCAGCATGT GTCTTCGCATTTA ATTGCTTTAGCAC TGGGCATCGTTCT TTTTAGTAGTGTTT AAGTAGATACTAC TAAAAAGACCGAT GGACAC [SEQ ID NO: 31] | GGGAAGGGCCT ATTTCCCAGCAT GTGTCTTCGCATT TAATTGCTTTAGC ACTGGGCATCGT TCTTTTTAGTAAA AACTAAAAAGAC CGATGGACAC [SEQ ID NO: 32] | GGGAAGGGCCTA TTTCCCAGCATGT GTCTTCGCATTTA ATTGCTTTAGCAC TGGGCATCGTTCT TAAAAAGACCGA TGGACAC [SEQ ID NO: 33] | GGGCCAAGGGA AGGGCCTATTTC CCAGCATGTGTC TTCGCATTTAATT GCTTTAGCACTG GGCATCGTTCTTT TTAGTAAAAACT AAAAAGACCGAT GGACAC [SEQ ID NO: 34] | GGGCCAAGGGA AGGGCCTATTTC CCAGCATGTGTC TTCGCATTTAATT GCTTTAGCACTG GGCATCGTTCTT AAAAAAGACCGA TGGACAC [SEQ ID NO: 35] |
| sg M296 | ATGTAACCCTATA GGGGTTGCGTGA GTCGGCCATAGTG CCTCGGCAACAGC GTAAAAAACTGCT GCCAGTGGTCGAA GTAAGTCAACAAA ACGGAGGTGGTG AAGTCACCCCCGT TTTGTAGGCCTAC TGGCAC [SEQ ID NO: 36] | GGATGTAACCCT ATAGGGGTTGCG TGAGTCGGCCAT AGTGCCTCGGCA ACAGCGTAAAAA ACTGCTGCCAGT GGTCGAAGTAAG TCAACAAAAATG TAGGCCTACTGG CAC [SEQ ID NO: 37] | GGTAACCCTATAG GGGTTGCGTGAG TCGGCCATAGTGC CTCGGCAACAGCG TAAAAAACTGCTG CCAGTGGTCGAAG TAAGTCAACAAAA ATGTAGGCCTACT GGCAC [SEQ ID NO: 38] | GGGATGTAACCC TATAGGGGTTGC GTGAGTCGGCCA TAGTGCCTCGGC AACAGCGTAAAA AACTGCTGCCAG TGGTCGAAGTAA GTCAACAAAAAT GTAGGCCTACTG GCAC [SEQ ID NO: 39] | GGGTAACCCTAT AGGGGTTGCGTG AGTCGGCCATAG TGCCTCGGCAAC AGCGTAAAAAAC TGCTGCCAGTGG TCGAAGTAAGTC AACAAAATGTA GGCCTACTGGCA C [SEQ ID NO: 40] |
| sg M297 | CGGAGGGAACTC CGTGAACGTGTCT TCCCCTTCGATGG GCTTGGCACACGG GGTCAATCGAGTT GCCGTTGAAGGC GGCGAATTCGCCG GCATCTCGATCGA CCGACAC [SEQ ID NO: 41] | GGAGGGAACTCC GTGAACGTGTCT TCCCCTTCGATG GCTTGGCACACG GGGTCAATCGA GTTGCCAAAAGG CATCTCGATCGA CCGACAC [SEQ ID NO: 42] | GGAGGGAACTCC GTGAACGTGTCTT CCCCTTCGATGGG CTTGGCACACGGG GTCAATCGAGTTA TCTCGATCGACCG ACAC [SEQ ID NO: 43] | GGCAGGCGGAG GGAACTCCGTGA ACGTGTCTTCCCC TTCGATGGGCTT GGCACACGGGG TCAATCGAGTTG GCACACGGGGTC AATCGAGTTATC TCGATCGACCGA CAC [SEQ ID NO: 44] | GGCAGGCGGAG GGAACTCCGTGA ACGTGTCTTCCCC TTCGATGGGCTT GGCACACGGGG TCAATCGAGTTA TCTCGATCGACC GACAC [SEQ ID NO: 45] |
| sg M298 | TTGCCTCTACAGG AGGCGAGAATGC CACGGCACGTGTC TTCCCCTTCAATG GCTTGGCACCGT GGAGTCGATCAGT TTTGTGCCGGCGA AGGGTTGCCGAC GTCAGCACCAACC TGATCGACGGACA C [SEQ ID NO: 46] | GCCTCTACAGGA GGCGAGAATGCC ACGGCACGTGTC TTCCCCTTCAATG GCTTGGCACCG TGGAGTCGATCA GAAAACTGATCG ACGGACAC [SEQ ID NO: 47] | GGGCCTCTACAGG AGGCGAGAATGC CACGGCACGTGTC TTCCCCTTCAATG GCTTGGCACCGT GGAGTCGATCAG AAAACTGATCGAC GGACAC [SEQ ID NO: 48] | GGGACATTGGCC TCTACAGGAGGC GAGAATGCCACG GCACGTGTCTTC CCCTTCAATGGG CTTGGCACCGTG GAGTCGATCAGA AAACTGATCGAC GGACAC [SEQ ID NO: 49] | NONE |
| sg M299 | GTCGCCTATAGGG CGATACAACTCCG AGCATGTGTCTTC CCCTTCAATGGGC TTGGCACTCGGCA TCGATCAAGCTCG CGTCGGCTGTCGG GCCAAAGCCGCGT CGGCCGACGCGG CCTTGATCGATGG ACAC [SEQ ID NO: 50] | GTCGCCTATAGG GCGATACAACTC CGAGCATGTGTC TTCCCCTTCAATG GGCTTGGCACTC GGCATCGATCAA GCTCGCGTCGGC TGTCGTCGGCCG ACGCGGCCTTGA TCGATGGACAC [SEQ ID NO: 51] | GTCGCCTATAGGG CGATACAACTCCG AGCATGTGTCTTC CCCTTCAATGGGC TTGGCACTCGGCA TCGATCAAGCTCG CGTAAAAACGCG GCCTTGATCGATG ACAC [SEQ ID NO: 52] | GGTCGCCTATAG GGCGATACAACT CCGAGCATGTGT CTTCCCCTTCAAT GGGCTTGGCACT CGGCATCGATCA AGCTCGCGTCGG CTGTCGTCGGCC GACGCGGCCTTG ATCGATGGACAC [SEQ ID NO: 53] | GGGTCGCCTATA GGGCGATACAAC TCCGAGCATGTG TCTTCCCCTTCAA TGGGCTTGGCAC TCGGCATCGATC AAGCTCGCGTAA AAACGCGGCCTT GATCGATGGACA C [SEQ ID NO: 54] |

To find the optimal gRNA length, different lengths of spacer, repeat:anti-repeat duplex and 3' end of the tracrRNA were included. These gRNAs were then synthesized as a single stranded DNA downstream of the T7 promoter with a proper guide sequence added at the 3'-end of each gRNA. These sgRNAs were amplified using two primers (5'-AAACCCCTCCGTTTAGAGAG [SEQ ID NO: 57] and 5'-AAGCTAATACGACTCACTATAGGCCAGTC [SEQ ID NO: 58]) and 1 uL of 10 uM diluted single stranded DNA as a template in 25 uL PCR reactions for each sgRNA according to the conditions of Table 4.

TABLE 4

| STEP | TEMPERATURE | TIME |
|---|---|---|
| DENATURATION | 98° C. | 30 SEC |
| 12 CYCLES | 98° C. | 10 SEC |
|  | 66° C. | 30 SEC |
|  | 72° C. | 2 MIN |
| FINAL EXTENSION | 72° C. | 2 MIN |
| HOLD | 12° C. |  |

The target library was designed based on an assumption that the eight randomized NNNNNNNN PAMs of these nucleases reside on the 5' end of the target sequence (5'-CCAGTCAGTAATGTTACTGG [SEQ ID NO: 59]).

Example 5: In Vitro Transcription and Translation for Production of MAD Nucleases and gRNAs The MADZYMEs were tested for activity by in vitro transcription and translation (txtl). A PURExpress® In Vitro Protein Synthesis Kit (NEB, Ipswich, Mass.) was used to produce MADzymes from the PCR-amplified MADZYME (Example 3) and also to produce the gRNA (Example 4) in a single reaction. In each well in a 96-well plate, the reagents listed in Table 5 were mixed to start the production of MADzymes and gRNAs:

TABLE 5

| | REAGENTS | VOLUME (µl) |
|---|---|---|
| 1 | SolA (NEB kit) | 10 |
| 2 | SolB (NEB kit) | 7.5 |
| 3 | PCR amplified gRNA | 0.4 |
| 4 | Murine RNase inhibitor (NEB) | 0.5 |
| 5 | Water | 3.0 |
| 6 | PCR amplified T7 MADZYME | 3.6 |

A master mix with all reagents was mixed on ice with the exception of the PCR-amplified T7-MADZYMEs to cover enough 96-well plates for the assay. After 21 µL of the master mix was distributed in each well in 96 well plates, 4 µL of the mixture of PCR amplified MADZYMEs and gRNA under the control of T7 promoter was added. The 96-well plates were sealed and incubated for 4 hrs at 37° C. in a thermal cycler. The plates were kept at room temperature until the target pool was added to perform the target depletion reaction.

After 4 hours incubation to allow production of the MADzymes and gRNAs, 4 µL of the target library pool (10 ng/µL) was added to the 10 µL aliquots of in vitro transcription/translation reaction mixture and allowed to deplete for 30 min, 3 hrs or overnight at 37° C. and 48° C. The target depletion reaction mixtures were diluted into PCR-grade water that contains RNAse A incubated for 5 min at room temperature. Proteinase K was then added and the mixtures were incubated for 5 min at 55° C. RNAseA/Proteinase K treated samples were purified with DNA purification kits and the purified DNA samples were then amplified and sequenced. The PCR conditions are shown in Table 6:

TABLE 6

| STEP | TEMPERATURE | TIME |
|---|---|---|
| DENATURATION | 98° C. | 30 SEC |
| 4 CYCLES | 98° C. | 10 SEC |
| | 66° C. | 30 SEC |
| | 72° C. | 20 SEC |

TABLE 6-continued

| STEP | TEMPERATURE | TIME |
|---|---|---|
| 12 CYCLES | 98° C. | 10 SEC |
| | 72° C. | 20 SEC |
| FINAL EXTENSION | 72° C. | 2 MINUTES |
| HOLD | 12° C. | |

Example 6: PAM Identification

Figure 5:
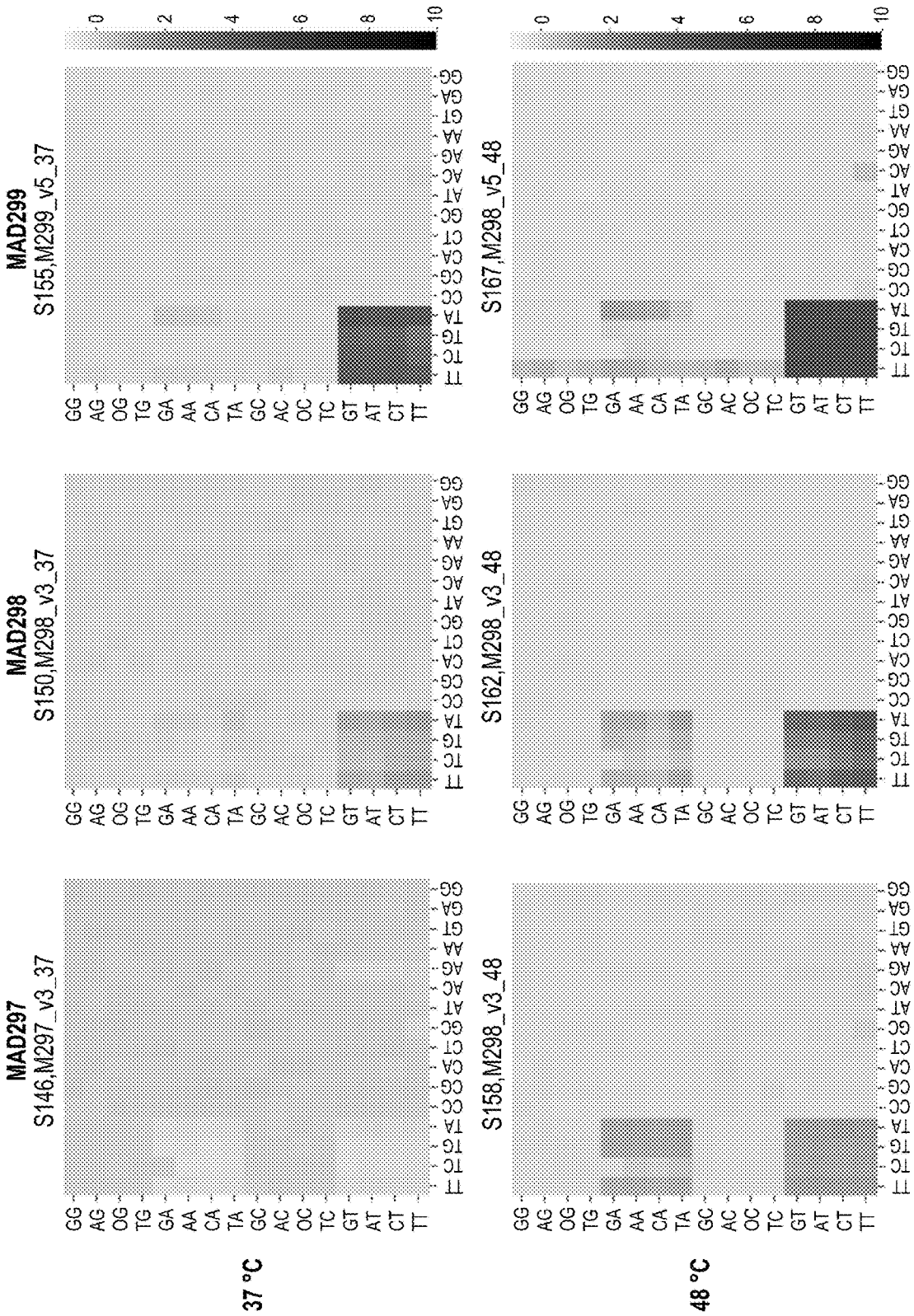
FIG. 5 shows heat maps of the three active Type V MADzymes identified herein.

The MAD297, MAD298 and MAD299 were screened for double-stranded break activity. FIG. 5 shows that the identified active MADzymes, namely MAD297, MAD298 and MAD299, had a wide PAM preference and high activity. FIG. 6 shows various parameters for the MADzymes with activity.

Example 7: In Vitro Plasmid Cut and Nick Assay

In vitro plasmid cut and nick assay with MAD297, MAD298, and MAD299 were performed by producing enzymes and sgRNA (sgM297v3, sgM298v3, and sgM299v5) with a guide sequence [SEQ ID NO: 59] attached to the 3'-end of each sgRNA under the T7 promoter in vitro. After the formation of RNP complex with sgRNA and MADzymes produced, supercoiled target DNA with an embedded target sequence [SEQ ID NO: 59] with the 5'-end addition of acgaTTTG replacing the randomized PAM sequence was added to the RNP complexes, with the knowledge that "TTTG" serves as an active PAM sequence for all three MADzymes. After 30 min incubation at 37° C., reaction mixtures were treated with RNase and Proteinase K then the target plasmid was purified using a PCR cleanup kit. The resulting plasmid targets were run on a TAE-agarose gel where different forms of plasmid architecture were visualized and distinguished between supercoiled, nicked, and linear DNA, where all three MADzymes (MAD297, MAD298, and MAD299) showed the nicked plasmid target product as the major product in vitro (data not shown).

Example 8: In Vivo Activity Assay in Mammalian Cells

Two different codon optimized versions of MADzymes were cloned under the CMV promoter and expressed in mammalian cells. The testing host cell line was the HEK293T cell line with a single copy of synthetic target GFP locus integrated randomly in the genome. Corresponding guides targeting the GFP locus were all cloned under the hU6 promoter with one of the sgRNA scaffolds chosen from the Table 3 for each MADzyme (sgM297v3, sgM298v3, and sgM299v5) with a guide sequence (Table 7) connected to the 3'-end of each sgRNA and an additional hepta-T sequence as a translational stop for guide expression. Table 7 shows the guide sequences with the PAM and the direction related to the direction of target GFP expression.

TABLE 7

| guide | PAM | guide_seq | SEQ ID NO: | direction |
|---|---|---|---|---|
| GFP12bg2 | TTG | CCGGTGGTGCAGATGAACTTCAG | [SEQ ID NO: 60] | Rev |
| GFP12bg3 | TTG | AAGAAGTCGTGCTGCTTCATGTG | [SEQ ID NO: 61] | Rev |
| GFP12bg4 | TTG | CCGTAGGTGGCATCGCCCTCGCC | [SEQ ID NO: 62] | Rev |
| GFP12bg6 | UC | GGGCATGGCGGACTTGAAGAAGT | [SEQ ID NO: 63] | Rev |
| GFP12bg7 | TTG | TGGCCGTTTACGTCGCCGTCCAG | [SEQ ID NO: 64] | Rev |

TABLE 7-continued

| guide | PAM | guide_seq | SEQ ID NO: | direction |
|---|---|---|---|---|
| GFP12bg8 | TTG | AAGAAGATGGTGCGCTCCTGGAC | [SEQ ID NO: 65] | Rev |
| GFP12bg9 | UT | GCCGGTGGTGCAGATGAACTTCA | [SEQ ID NO: 66] | Rev |
| GFP12bg10 | UC | ATCTGCACCACCGGCAAACTGCC | [SEQ ID NO: 67] | For |
| GFP12bg11 | UC | AGCGTGTCCGGCGAGGGCGAGGG | [SEQ ID NO: 68] | For |
| GFP12bg12 | TTG | GTGACCACCCTGACCTACGGCGT | [SEQ ID NO: 69] | For |
| GFP12bg13 | UC | AGCCGCTACCCCGACCACATGAA | [SEQ ID NO: 70] | For |
| GFP12bg14 | UC | TTCAAGTCCGCCATGCCCGAAGG | [SEQ ID NO: 71] | For |
| GFP12bg15 | UC | TTCAAGGACGACGGCAACTACAA | [SEQ ID NO: 72] | For |
| GFP12bg16 | UC | AAGGACGACGGCAACTACAAGAC | [SEQ ID NO: 73] | For |

Figure 7:
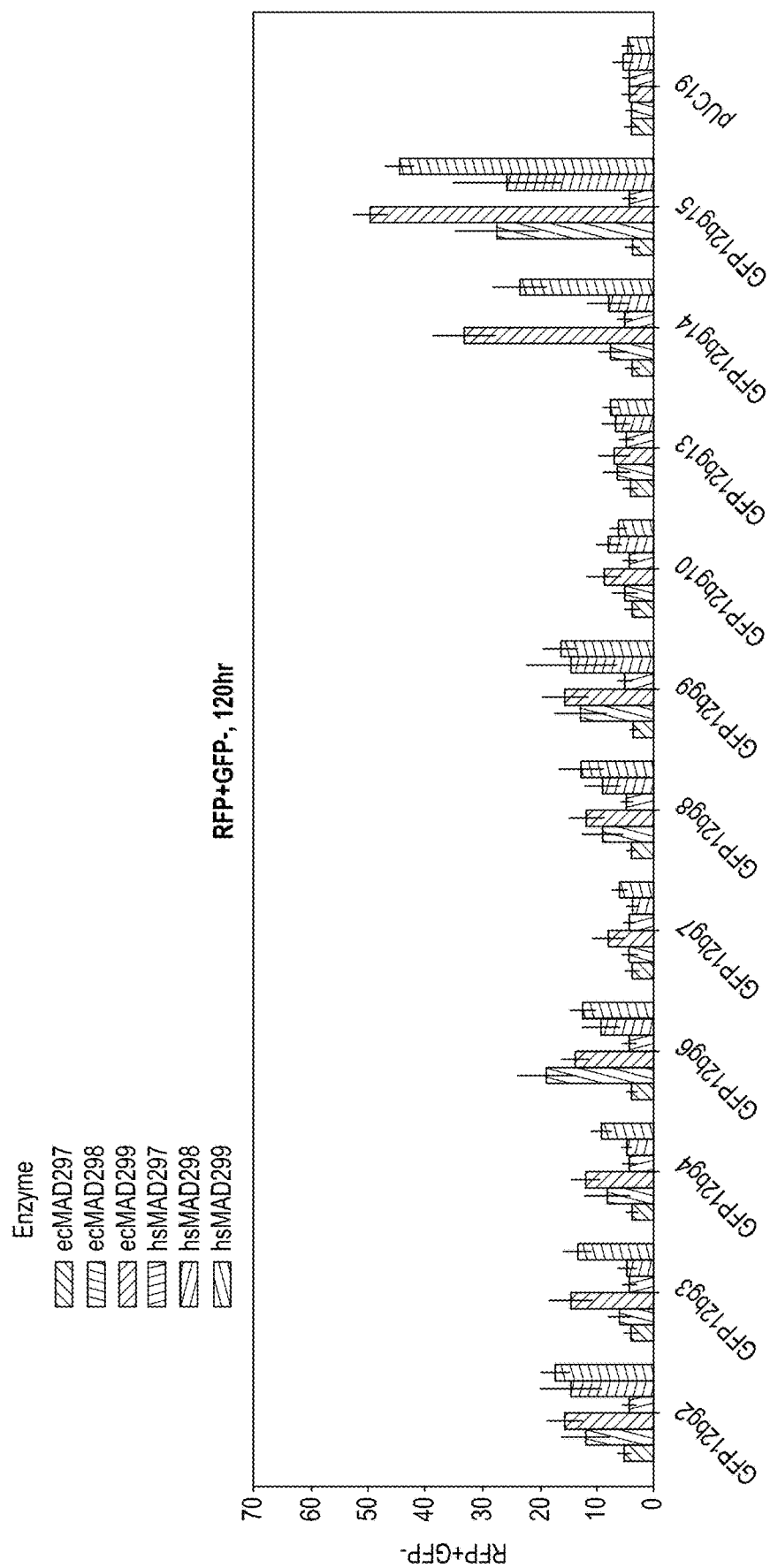
FIG. 7 shows the results from cells that were collected and analyzed using a flow cytometry to detect depletion of a GFP signal as evidence of double-strand breaks that interrupt the expression of the target gene.

A guide expressing plasmid (50 ng, or pUC19 as a negative control) and a MADzyme expressing plasmid (50 ng) was mixed with 1 uL Polyfect and diluted in 35 μL OptiMem, and added to 25K TrypLE singulated HEK293T host cells as described above in 100 μL DMEM for reverse transfection. Five days after transfection, the cells were collected and analyzed using a flow cytometry to detect depletion of a GFP signal as evidence of double-strand breaks that interrupt the expression of the target gene. The results are shown in FIG. 7. As shown in FIG. 7, MAD298 and MAD299 showed evidence of double-strand breaks in vivo, where MAD297 did not.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A nuclease system configured to perform nucleic acid-guided nuclease editing, wherein the nuclease system is selected from the group consisting of: a MAD293 system comprising SEQ ID NO: 1, SEQ ID NO: 2 and SEQ ID NO: 3; a MAD294 system comprising SEQ ID NO: 4, SEQ ID NO: 5 and SEQ ID NO: 6; a MAD295 system comprising SEQ ID NO: 7, SEQ ID NO: 8 and SEQ ID NO: 9; a MAD296 system comprising SEQ ID NO: 10, SEQ ID NO: 11 and SEQ ID NO: 12; a MAD297 system comprising SEQ ID NO: 13, SEQ ID NO: 14 and SEQ ID NO: 15; a MAD298 system comprising SEQ ID NO: 16, SEQ ID NO: 17 and SEQ ID NO: 18; and a MAD299 system comprising SEQ ID NO: 19, SEQ ID NO: 20 and SEQ ID NO: 21.

2. The nuclease system of claim 1, wherein the nuclease system is a MAD293 system comprising SEQ ID NO: 1, SEQ ID NO: 2 and SEQ ID NO: 3.

3. The nuclease system of claim 1, wherein the nuclease system is a MAD294 system comprising SEQ ID NO: 4, SEQ ID NO: 5 and SEQ ID NO: 6.

4. The nuclease system of claim 1, wherein the nuclease system is a MAD295 system comprising SEQ ID NO: 7, SEQ ID NO: 8 and SEQ ID NO: 9.

5. The nuclease system of claim 1, wherein the nuclease system is a MAD296 system comprising SEQ ID NO: 10, SEQ ID NO: 11 and SEQ ID NO: 12.

6. The nuclease system of claim 1, wherein the nuclease system is a MAD297 system comprising SEQ ID NO: 13, SEQ ID NO: 14 and SEQ ID NO: 15.

7. The nuclease system of claim 1, wherein the nuclease system is a MAD298 system comprising SEQ ID NO: 16, SEQ ID NO: 17 and SEQ ID NO: 18.

8. The nuclease system of claim 1, wherein the nuclease system is a MAD299 system comprising SEQ ID NO: 19, SEQ ID NO: 20 and SEQ ID NO: 21.

* * * * *

SEQUENCE LISTING

```
<160> NUMBER OF SEQ ID NOS: 73

<210> SEQ ID NO 1
<211> LENGTH: 1400
<212> TYPE: PRT
<213> ORGANISM: Artificial Sequence
<220> FEATURE:
<223> OTHER INFORMATION: ENGINEERED NUCLEASE

<400> SEQUENCE: 1
```

| Met | Ala | Ala | Phe | Gln | Arg | Ser | Tyr | Thr | Met | Asn | Leu | Lys | Pro | Ala | Thr |
|---|---|---|---|---|---|---|---|---|---|---|---|---|---|---|---|
| 1 | | | | 5 | | | | | 10 | | | | | 15 | |
| Ser | Glu | Gln | Asp | Lys | Phe | Ile | Leu | Trp | Asn | Arg | Leu | Phe | Leu | Thr | His |
| | | | 20 | | | | | 25 | | | | | 30 | | |
| Trp | Ser | Val | Asn | Glu | Gly | Ala | Lys | Ile | Phe | Gly | Glu | Leu | Phe | Leu | Asn |
| | | | 35 | | | | | 40 | | | | | 45 | | |
| Leu | Arg | Gly | Gly | Leu | Ser | Pro | Glu | Leu | Asp | Ile | Phe | Asp | Leu | Asp | Lys |
| | | 50 | | | | | 55 | | | | | 60 | | | |
| Val | Lys | Asp | Asp | Lys | Lys | Lys | Ala | Phe | Val | Met | Gly | Arg | Arg | | |
| 65 | | | | | 70 | | | | | 75 | | | | 80 | |
| Leu | Leu | Ala | Leu | Gly | Trp | Leu | Ser | Val | Glu | Asp | Asn | Leu | Ser | Ala | Gly |
| | | | | 85 | | | | | 90 | | | | | 95 | |
| Glu | His | Pro | Phe | Arg | Ile | Arg | Glu | Ile | Pro | Val | Gly | Arg | Asn | Met | Gly |
| | | | 100 | | | | | 105 | | | | | 110 | | |
| Lys | Ser | Gln | Ala | Ser | Thr | Leu | Leu | Thr | Glu | Ile | Leu | Lys | Asn | Lys | Gly |

-continued

```
            115                 120                 125
Ile Lys Asp Glu Ala Val Ile Lys Glu Trp Ile Asp Asp Cys Thr Pro
            130                 135                 140
Ser Leu Ile Ala Asn Ile Arg Glu Asp Ala Val Trp Ile Asn Arg Ala
145                 150                 155                 160
Ser Ser Phe Asn Ser Ile Thr Pro Cys Pro Thr Lys Asp Glu Val Trp
                    165                 170                 175
Ile Val Leu Ser Gly Leu Leu Gly Leu Arg Phe Leu Asp Leu Ser Leu
                    180                 185                 190
Glu Glu Val Lys Gly Lys Glu Thr Glu Tyr Leu Tyr Asp Leu Gly Glu
                    195                 200                 205
Lys Glu Thr Gln Ser Lys Ser Asp Pro Ser Lys Lys Ala Arg Glu Leu
            210                 215                 220
Phe Gly Asn Leu Phe Thr Gln Asn Pro Val Leu Met Lys Asn Ser Arg
225                 230                 235                 240
Asp Lys Lys Asp Thr Phe Ala Lys Glu Phe Tyr Leu Ala Phe Lys Glu
                    245                 250                 255
Phe Lys Asp Tyr Glu Lys Leu Lys Glu Lys Ile Glu Ser Trp Arg Lys
                    260                 265                 270
Glu Lys Glu Phe Pro Leu Ile Glu Asn Pro Val Ala Glu Lys Tyr Pro
            275                 280                 285
Pro Glu Val Thr Phe Thr Gly Ser Pro Cys Thr Val Ser Lys Arg Tyr
            290                 295                 300
Arg Lys Leu Leu Val Ser Leu Glu Leu Trp Pro Ser Ser Gln Asp Glu
305                 310                 315                 320
Asn Gly Asn Ile Pro Lys Thr Glu Lys Thr Glu Asp Lys Thr His Asn
                    325                 330                 335
Gln Val Leu Leu Asp Tyr Leu Leu Lys Ala Cys Asn Glu Gly Asn Lys
                    340                 345                 350
Gly Thr Gln Lys Ile Ile Thr Pro Val Trp Ala Asn Asn Leu Lys Ala
            355                 360                 365
Glu Leu Glu Leu Lys Met Asn Glu Ile Ile Arg Ile Gly Glu Ser Ser
    370                 375                 380
Ser Thr Glu Leu Gln Arg Leu Met Ile Lys Met Ala Ala Arg Arg Ile
385                 390                 395                 400
Ser Gln Thr Leu Ser Trp Ile Lys Ile Asn Glu Gln Thr Lys His Asp
                    405                 410                 415
Ala Tyr Gln Lys Lys Asn Lys Ala Phe Lys Leu Leu Ser Glu Ile Asp
                    420                 425                 430
Lys Asn Gly Glu Ala Cys Lys Trp Leu Glu Asn Tyr Glu Leu Phe Arg
            435                 440                 445
Thr Asp Asp Ser Gly Gly Glu Tyr His Ile Ser Leu Arg Ala Ile
            450                 455                 460
Ser Cys Trp Lys Gln Ile Leu Glu Glu Trp Gln Lys Asn Asp Ser Pro
465                 470                 475                 480
Lys Ala Leu Arg Glu Lys Val Lys Glu Val Gln Ala Glu Glu Glu Lys
                    485                 490                 495
Phe Gly Asp Ala Arg Leu Phe Glu Asp Leu Ala Asp Asn Ala Arg
                    500                 505                 510
Ser Val Trp Leu Leu Pro Asp Gly Asn Lys Thr Pro Asp Ile Leu Asn
            515                 520                 525
Trp Trp Cys Glu Tyr Arg Thr Ala Glu Ile Asp Glu Ser Arg Phe Lys
            530                 535                 540
```

```
Ile Pro Cys Tyr Cys His Pro His Pro Phe Lys His Pro Val Tyr Val
545                 550                 555                 560

Glu Tyr Gly Lys Ser Asn Pro Lys Val Ile Phe Ala Met Lys Asn Asn
                565                 570                 575

Lys Val Lys Lys Gly His Ile Glu His Gly Trp Asn Pro Gln Asn Pro
            580                 585                 590

Arg Ser Ile Ala Leu Ser Leu Phe Asn Asn Gly Asn Arg Glu Ser Ser
        595                 600                 605

Leu Val Pro Phe Ile Trp Glu Ser Lys Arg Leu Trp Lys Asp Leu Gly
610                 615                 620

Gly Glu Ala Thr Gln Ile Gly Asp Ile Pro Arg Ser Asp Arg Met Gly
625                 630                 635                 640

Leu Ser Gly Lys Arg Glu Ser Val Lys Pro Lys Ala Pro Phe Gln Lys
                645                 650                 655

Glu Val Trp Asn Ala Arg Leu Gln Ser Asp Arg Arg Thr Leu Glu Lys
                660                 665                 670

Leu Glu Lys Tyr Trp Asn Pro Glu Ser Met Lys Trp Ile Asp Asp Gly
            675                 680                 685

Lys Phe Leu Ile Gln Ser Lys Trp Phe Ile Thr Phe Gly Pro Asp Met
690                 695                 700

Glu Thr Ala Glu Gly Pro Trp Lys Leu Tyr Leu Lys Glu Lys Tyr Val
705                 710                 715                 720

Asp Asn Lys Ile Leu Gly Asn Arg Ser Lys Glu Asn Gln Lys Arg Gly
                725                 730                 735

Tyr Arg Ala Lys Lys Leu Leu Ser Gly Tyr Pro Ala Gly Met Arg Ile
                740                 745                 750

Leu Ser Val Asp Leu Gly His Arg Tyr Ala Ala Ser Cys Ala Val Trp
            755                 760                 765

Glu Thr Ile Thr Lys Lys Gln Ile Thr Glu Glu Leu Ala Tyr Gln Pro
770                 775                 780

Asp Asn Asn Ser Leu Phe Glu His Ser Cys Lys Thr Ile Asp Lys Lys
785                 790                 795                 800

Ile Lys Asn Thr Val Tyr Arg Arg Ile Gly Glu Asp Ser Ile Asp Ala
                805                 810                 815

Pro Trp Ala Lys Leu Glu Lys Gln Phe Thr Ile Lys Leu Gln Gly Glu
                820                 825                 830

Asp Lys Ser Cys Tyr Leu Leu Arg Ser Asp Glu Lys Glu Leu Phe Arg
            835                 840                 845

Ser Ile Leu Ser Lys Leu Ser Cys Leu Asn Asn Asp Thr Gly His Asn
850                 855                 860

Ile Leu Glu Met Ile Glu Asn Leu Leu Arg Ile Val Lys Ala Lys Ile
865                 870                 875                 880

Tyr Arg Gln Gly Ile Leu Ala Arg Ile Ser Tyr Ser Met Thr Ala Gln
                885                 890                 895

Tyr Lys Pro Gly Lys Gly Gly Gln Lys Ser Pro Leu Ser Asp Glu Asp
            900                 905                 910

Lys Ile His Tyr Leu Ser Glu Asn Leu Ala Ala Trp Ser Ala Ile Met
        915                 920                 925

Gly Asn Gln Glu Trp Asn Glu Asp Val Ile Ser Asp Trp Tyr Lys Thr
930                 935                 940

Tyr Ile Ser His Leu Val Ser Gly Pro Lys Pro Lys Glu Gly Asn Arg
945                 950                 955                 960
```

```
Lys Ser Asp Arg Asp Lys Ile Ile Glu Tyr Phe Leu Pro Ala Ala Arg
            965                 970                 975

Lys Leu Tyr Asp Asp Asn Glu Thr Arg Ile Lys Ile His Asp Leu Phe
            980                 985                 990

Lys Glu Leu Trp Asp Glu Asn Asn Lys Gln Leu Ser Ala Val Leu Lys
        995                 1000                1005

Glu Ile Lys Lys Ile Ile Leu Pro Lys Gly Ile Arg Tyr Phe Asp
    1010                1015                1020

Lys Asn Thr Asp Asn Pro Ser Lys Trp Lys Asn Asn Gln Ser Lys
    1025                1030                1035

Leu Lys Gln Ile Thr His Arg Gly Gly Leu Ser Met Gln Arg Ile
    1040                1045                1050

Val Ala Ile Glu Glu Tyr Tyr Lys Leu Ala Lys Ala Tyr Lys Asn
    1055                1060                1065

His Pro Glu Pro Asp Asp Leu Thr Lys Asn Ile Pro Leu Pro Gly
    1070                1075                1080

Asp Asn Ser Ser Ala Gly Phe Asn Gln Arg Ile Arg Asp Thr Leu
    1085                1090                1095

Glu Arg Met Lys Glu Gln Arg Val Lys Gln Ile Ala Ser Arg Ile
    1100                1105                1110

Val Glu Ser Ala Leu Gly Leu Gly Ile Glu Gly Tyr Lys Lys Arg
    1115                1120                1125

Pro Leu Thr Pro Glu Asn Lys Pro Cys Gln Ala Ile Val Ile Glu
    1130                1135                1140

Asp Leu Ser His Tyr Arg Pro Asp Glu Leu Gln Thr Arg Arg Glu
    1145                1150                1155

Asn Arg Arg Leu Met Gln Trp Ser Ser Ser Lys Val Lys Lys Tyr
    1160                1165                1170

Leu Lys Glu Ala Cys Glu Met His Asp Val Arg Leu Val Glu Ile
    1175                1180                1185

Ser Pro Glu Tyr Thr Ser Arg Gln Asp Ser Arg Thr Gly Ala Ala
    1190                1195                1200

Gly Leu Arg Cys Ile Asp Ile Asn Ile Arg Glu Phe Leu Lys Asp
    1205                1210                1215

Ser Ser Arg Trp Gln Asn Lys Ile Asn Thr Ile Gln Lys Lys Pro
    1220                1225                1230

Ala Asn Lys Lys Ser Asn Leu Asp Gln Tyr Leu Ile Glu Leu Asn
    1235                1240                1245

Glu Ser Leu Gly Asn Lys Tyr Lys Asp Lys Val Ile Pro Ser Asp
    1250                1255                1260

Asn Phe Val Arg Ile Pro Arg Lys Gly Gly Asp Val Phe Val Ser
    1265                1270                1275

Ser Ser Lys Glu Ser Pro Val Ser Lys Gly Ile Gln Ala Asp Leu
    1280                1285                1290

Asn Ala Ala Ala Asn Ile Gly Leu Lys Ala Leu Leu Asp Pro Asp
    1295                1300                1305

Trp Ala Gly Ala Trp Trp Tyr Ile Leu Ile Glu Val Lys Ser Asn
    1310                1315                1320

His Val Ile Pro Tyr Gly Glu Lys Tyr Lys Gly Ser Glu Cys Leu
    1325                1330                1335

Arg Ala Trp Lys Phe Ser Gly Leu Glu Asn Gln Val Met Lys Asn
    1340                1345                1350

Asn Met Asn Leu Trp Arg Asp Leu Gln Ser Gln Phe Ser Gly Glu
```

```
                1355                1360                1365

Asp Lys Trp Met Ser Tyr Lys Glu Tyr Asn Glu Leu Thr Glu Lys
        1370                1375                1380

Arg Val Ile Asn Ile Leu Arg Glu Arg Ala Gly Leu Glu Leu Ile
    1385                1390                1395

Lys Glu
    1400

<210> SEQ ID NO 2
<211> LENGTH: 37
<212> TYPE: DNA
<213> ORGANISM: Artificial Sequence
<220> FEATURE:
<223> OTHER INFORMATION: CR RNA FOR ENGINEERED NUCLEASE

<400> SEQUENCE: 2
gtttaagtag atactactga aaagaccgat ggacaca                              37

<210> SEQ ID NO 3
<211> LENGTH: 74
<212> TYPE: DNA
<213> ORGANISM: Artificial Sequence
<220> FEATURE:
<223> OTHER INFORMATION: TRACRRNA FOR ENGINEERED NUCLEASE

<400> SEQUENCE: 3
gggaagggcc tatttcccag catgtgtctt cgcatttaat tgctttagca ctgggcatcg     60 ttcttttttag tagt                                                     74

<210> SEQ ID NO 4
<211> LENGTH: 1375
<212> TYPE: PRT
<213> ORGANISM: Artificial Sequence
<220> FEATURE:
<223> OTHER INFORMATION: ENGINEERED NUCLEASE

<400> SEQUENCE: 4

Met Asn Arg Ile Tyr Gln Gly Arg Val Ser Lys Ile Glu Ile Lys Asp
1               5                   10                  15

Ser Glu Gly Asn Phe Arg Asn Val Pro Val Gly Ser Pro Asp Thr Cys
            20                  25                  30

Pro Leu Trp Arg His His Arg Ile Phe Gln Asp Ala Val Asn Tyr Tyr
        35                  40                  45

Leu Val Ala Leu Gly Ala Leu Ala Gly Thr Gly Ser Glu Asn Ala Phe
    50                  55                  60

Val Gly Leu Gly Ser Lys Asp Arg Val Ile His Asp Leu Tyr Ser Arg
65                  70                  75                  80

Leu Phe Asp Ser Trp Glu Arg Phe Pro Arg Asp Met His Gly Ala Ser
                85                  90                  95

Ser Leu Arg Asp Ser Leu Arg Arg Thr Leu Pro Gly Leu Ser Glu Arg
            100                 105                 110

Ala Ser Leu Gln Asp Ala Phe Asp Ala Ile Leu Ser Gly Asn Glu Ala
        115                 120                 125

Asn Ala Arg Glu Arg Val Leu Ser Leu Leu Ser Leu Ile Gln Asp Leu
    130                 135                 140

Gly Gly Asp Ile Gln Lys Gly Ser Lys Arg Tyr Phe Pro Phe Phe Cys
145                 150                 155                 160

Glu Pro Ala Thr Lys Ala Thr Phe Pro Arg Ala Arg Val Gly Leu Leu
                165                 170                 175
```

```
Lys Val Glu Gly Lys Asp Phe Val Pro Arg Leu Leu Trp Ser Ser Asp
            180                 185                 190

Leu Glu Ile Ala Pro Asp Gln Val Val Glu Gln Leu Lys Phe Glu Tyr
        195                 200                 205

Phe Ala Asn Pro Asn Glu Ser Val Gln Pro Ile Glu Gly Asn Glu Ala
    210                 215                 220

Arg Val Arg Leu Ile Glu Ala Leu Asp Asn Pro Gln Leu Gly Ile Glu
225                 230                 235                 240

Leu Pro Ile Glu Ile Leu Ser Asp Leu Arg Lys Arg Val His Leu Ile
                245                 250                 255

Glu Thr Asp Ile Arg Ile Pro Arg Tyr Phe Phe Gly Gly Ala Gly Ala
            260                 265                 270

Glu Leu Arg Lys Phe Arg Leu Asp Leu Phe Leu Ile Ala Ala Tyr Val
        275                 280                 285

Thr Pro Asp Pro Ser Ile Leu Arg Ala Leu Arg Asn Ser Phe Lys Glu
    290                 295                 300

Pro Ser Ala Ser Lys Ser Ser Lys Lys Lys Asp Glu Thr Glu Glu Val
305                 310                 315                 320

Glu Asn Leu Leu Arg Ser Leu Gly Asp Asp Pro Leu Ile Leu Ala Arg
                325                 330                 335

Gly Glu Arg Gly Phe Val Phe Pro Ser Phe Thr Ser Leu Pro Thr Trp
            340                 345                 350

Val Gly Ala Asn Ala Gln Lys Pro Ile Trp Arg Asp Phe Asp Ile Ala
        355                 360                 365

Ala Phe Ala Glu Ala Leu Lys Ser Leu Asn Gln Phe Thr Ala Lys Thr
    370                 375                 380

Glu Glu Arg Glu Glu Lys Leu Lys Lys Ala Glu Glu Thr Leu His Tyr
385                 390                 395                 400

Met Leu Gly Ile Ser Asp Ala Ile Pro Arg Ser Ser Asp Ser Glu Thr
                405                 410                 415

Glu Glu Gln Ala Pro Ser Arg Pro Gly Lys Asp Pro Arg Trp Pro Leu
            420                 425                 430

Val Ala Gln Leu Glu Lys Glu Leu Gly Glu Asn Leu Ser Glu Gly Thr
        435                 440                 445

Trp Gln Leu Ser Arg Ser Ala Met Arg Gly Leu Arg Asp Ile Ile Gly
    450                 455                 460

Leu Trp Arg Lys His Pro Gly Ala Ser Val Val Thr Leu Gln Lys Asp
465                 470                 475                 480

Val Lys Thr Tyr Gln Ala Asp Glu Lys His Lys Arg Glu Ile Gly Ser
                485                 490                 495

Val Gln Leu Phe Leu Leu Leu Cys Glu Glu Arg Tyr His Ala Leu Trp
            500                 505                 510

Gln Thr Glu Thr Asp Asp Glu Arg Gly Asp Glu Ser Glu Glu Asn Asp
        515                 520                 525

Asp Pro Ala Arg Ile Leu Ser Asp Ala Ile Glu Val His Gln Ile Arg
    530                 535                 540

Arg Glu Val Glu Arg Phe Arg Glu Pro Ile Arg Leu Thr Pro Ala Glu
545                 550                 555                 560

Pro Val Phe Ser Arg Arg Leu Phe Met Phe Ser Asp Leu Thr Asp Lys
                565                 570                 575

Leu Ala Lys Val Lys Phe Gly Glu Thr Thr Glu Glu Asn Ser Glu Val
            580                 585                 590
```

```
Lys Ser Gln Phe Val Glu Ala Ile Ala Leu Lys Glu Gly Glu Asn
            595                 600                 605

Leu Lys Glu Ala Arg Val Arg Ile Thr Phe Ser Ala Pro Arg Leu His
        610                 615                 620

Arg Asp Glu Leu Leu Gly Gly Ala Glu Ser Arg Trp Leu Gln Pro Ile
625                 630                 635                 640

Thr Ala Ala Leu Gly Phe Ser Asn Pro Ala Pro Ser Val Lys Phe Asp
                645                 650                 655

Ser Ala Val Ala Leu Met Pro Asp His Met Asp Asp Gly Arg Ile Arg
                660                 665                 670

His Leu Leu Asn Phe Pro Val Asn Phe Asp Ser Ala Trp Leu His Gln
                675                 680                 685

Ser Ile Gly Lys Ala Asp Leu Trp Lys Ser Gln Phe Asn Gly Thr Lys
            690                 695                 700

Asp Lys Asn Leu His Leu His Trp Ala Gly Thr Ala Arg Asp Thr Thr
705                 710                 715                 720

Arg Lys Asn Thr Trp Trp Glu Asn Arg Thr Ile Ile Glu Asn Gly Phe
                725                 730                 735

Thr Val Leu Ser Asn Asp Leu Gly Gln Arg Ser Ala Gly Ala Trp Ala
                740                 745                 750

Leu Leu Lys Val Thr Cys Ser Arg Pro Asp Thr Lys His Pro Val Arg
            755                 760                 765

Ser Ile Gly His Asp Gly Thr Arg Glu Trp Phe Ala Thr Val Leu Ala
            770                 775                 780

Thr Gly Ile His Arg Leu Pro Gly Glu Asp Gln Arg Ile Leu Lys Asn
785                 790                 795                 800

Gly Lys Trp Ala Thr Glu Gln Ser Gly Lys Lys Gly Arg Asn Ala Thr
                805                 810                 815

Phe Ser Glu Tyr Glu Ala Ala Cys Val Leu Ala Lys Asn Leu Gly Cys
                820                 825                 830

Glu Ser Val Glu Asn Trp Leu Gly Met Ser Gly Glu Lys Ser Tyr Pro
            835                 840                 845

Ala Leu Asn Asp Gln Leu Val Lys Ile Ala Asn Arg Arg Ile Thr Arg
850                 855                 860

Leu Gly Thr Tyr His Arg Trp Ser Cys Phe Ser Pro Glu Lys Phe Glu
865                 870                 875                 880

Asp Pro Ala Arg Arg Ala Asn Val Ile Gly Gln Leu Ala Glu Leu
                885                 890                 895

Ser Ala Tyr Gln Asp Glu Asn Val Thr Val Ser Ala Asp Ile Leu Lys
                900                 905                 910

Ser Gly Asp Phe Glu Gly Phe Arg His Arg Ala Gly Ala Ala Phe Glu
            915                 920                 925

Ala Leu Arg Thr Glu Leu Glu Val His Leu Val Asn Leu Ala Asn Leu
930                 935                 940

Thr Ala Pro Leu Arg Gln Lys Val Trp Ser Trp Gln Lys Arg Pro Asp
945                 950                 955                 960

Ser Ser Gly Tyr Gly Asp Leu Leu Met Val Asp Leu Asp Asp Cys His
                965                 970                 975

Pro Lys Ile Arg Gly Gln Arg Gly Leu Ser Met Ala Arg Leu Glu Gln
                980                 985                 990

Leu Glu Gly Leu Arg Arg Leu Phe Leu Arg Tyr Asn Arg Ser Leu Asp
            995                 1000                1005

Arg Ser Pro Gly Ile Pro Ala Lys Phe Gly Arg Glu Asp Val Gly
```

```
              1010                1015                1020

Arg  Thr  Ser  Gly  Glu  Pro  Cys  Gln  Ala  Leu  Leu  Val  Lys  Ile  Asp
         1025                1030                1035

Arg  Met  Lys  Glu  Gln  Arg  Val  Asn  Gln  Thr  Ala  His  Leu  Ile  Leu
         1040                1045                1050

Ala  Gln  Ala  Leu  Gly  Val  Arg  Leu  Cys  Pro  His  Arg  Ile  Glu  Glu
         1055                1060                1065

Asn  Glu  Arg  Lys  Ser  Arg  Asp  Leu  His  Gly  Glu  Tyr  Glu  Lys  Ile
         1070                1075                1080

Pro  Gly  Arg  Glu  Pro  Val  Asp  Phe  Ile  Val  Ile  Glu  Asp  Leu  Ser
         1085                1090                1095

Arg  Tyr  Leu  Ser  Ser  Gln  Gly  Arg  Ala  Pro  Ser  Glu  Asn  Ser  Arg
         1100                1105                1110

Leu  Met  Lys  Trp  Ala  His  Arg  Ala  Val  Arg  Asp  Lys  Leu  Lys  Met
         1115                1120                1125

Leu  Ala  Glu  Glu  Pro  Phe  Gly  Ile  Pro  Val  Val  Glu  Thr  Val  Pro
         1130                1135                1140

Ala  Tyr  Ser  Ser  Arg  Phe  His  Ala  Leu  Asn  Gly  Gln  Ala  Gly  Ser
         1145                1150                1155

Arg  Leu  His  Glu  Leu  His  Glu  Leu  Glu  Ala  Tyr  Gln  Gln  Gln  Ser
         1160                1165                1170

Leu  Ile  Asn  Leu  Ala  Ala  Lys  Thr  Asp  Phe  Gln  Asn  Arg  Asp  Arg
         1175                1180                1185

Ser  Lys  Ala  Ala  Gly  Glu  Leu  Phe  Glu  Gln  Phe  Gln  Ala  Leu  Ala
         1190                1195                1200

Lys  Leu  Asn  Glu  Arg  Arg  Ala  Glu  Gly  Lys  Lys  Val  Pro  Arg
         1205                1210                1215

Thr  Leu  Tyr  Tyr  Pro  Lys  Ser  Gly  Gly  Pro  Leu  Phe  Leu  Ala  Ser
         1220                1225                1230

Arg  Asp  Gly  Asp  Thr  Ile  His  Ala  Asp  Val  Asn  Ala  Ala  Ile  Asn
         1235                1240                1245

Leu  Gly  Leu  Arg  Ala  Ile  Ala  Ala  Pro  Ala  Cys  Ile  Asp  Ile  His
         1250                1255                1260

Arg  Arg  Leu  Arg  Ala  Thr  Lys  Glu  Lys  Glu  Val  Tyr  Arg  Pro  Arg
         1265                1270                1275

Val  Gly  Asn  Ala  Arg  Glu  Lys  Ser  Ala  Phe  Ser  Lys  Asp  Asp  Ile
         1280                1285                1290

Ile  Gln  Pro  Ser  Gly  Ala  Pro  Ser  Lys  Lys  Phe  Ala  Ser  Ser  Ser
         1295                1300                1305

Ser  Pro  Asn  Phe  Phe  Tyr  Glu  Pro  Glu  Asp  Leu  Lys  Gln  Ala  Asn
         1310                1315                1320

Gly  Glu  Pro  Leu  Phe  Asp  Arg  Ala  Met  Phe  Gly  Glu  Tyr  Ser  Leu
         1325                1330                1335

Val  Ser  Gly  Val  Ser  Leu  Trp  Ser  Met  Val  Asn  Asn  Ala  Ile  Tyr
         1340                1345                1350

Ile  Arg  Cys  Val  Glu  Leu  Asn  Arg  Thr  Arg  Leu  His  Gly  Lys  Asp
         1355                1360                1365

Pro  Asp  Asp  Gln  Ile  Pro  Met
         1370                1375

<210> SEQ ID NO 5
<211> LENGTH: 36
<212> TYPE: DNA
<213> ORGANISM: Artificial Sequence
```

```
<220> FEATURE:
<223> OTHER INFORMATION: CRRNA FOR ENGINEERED NUCLEASE

<400> SEQUENCE: 5
gccgcagccc ccgcgatggg aaagagattg tggcgg                                    36

<210> SEQ ID NO 6
<211> LENGTH: 97
<212> TYPE: DNA
<213> ORGANISM: Artificial Sequence
<220> FEATURE:
<223> OTHER INFORMATION: TRACR RNA FOR ENGINEERED NUCLEASE

<400> SEQUENCE: 6
gccccgattt ccctttgaat gatctcggcc tcgttgccac tgaccgaatt cttccgcctt         60
tggaattcca agctctttga catcgcgagc gctgagg                                   97

<210> SEQ ID NO 7
<211> LENGTH: 1397
<212> TYPE: PRT
<213> ORGANISM: Artificial Sequence
<220> FEATURE:
<223> OTHER INFORMATION: ENGINEERED NUCLEASE

<400> SEQUENCE: 7
```

Met Ala Ala Phe Gln Arg Ser Tyr Thr Met Asn Leu Lys Pro Ala Thr
1               5                   10                  15

Ser Glu Gln Asp Lys Phe Ile Leu Trp Asn Arg Leu Phe Leu Thr His
            20                  25                  30

Trp Ser Val Asn Glu Gly Ala Lys Ile Phe Gly Glu Leu Phe Leu Asn
        35                  40                  45

Leu Arg Gly Gly Leu Ser Pro Glu Leu Gly Ile Phe Asp Leu Asn Lys
    50                  55                  60

Asp Lys Asp Asp Arg Lys Lys Lys Ala Leu Val Met Gly Arg Arg Arg
65                  70                  75                  80

Leu Leu Ala Leu Gly Trp Leu Ser Val Glu Asp Asn Leu Ser Ala Gly
                85                  90                  95

Asp His Pro Phe Arg Ile Arg Glu Ile Pro Val Gly Arg Asn Met Glu
            100                 105                 110

Ile Lys Gln Ala Thr Thr Leu Leu Thr Glu Ile Leu Lys Asn Lys Gly
        115                 120                 125

Val Lys Asp Glu Ala Val Ile Lys Glu Trp Ile Asp Asp Cys Thr Pro
    130                 135                 140

Ser Leu Ile Ala Asn Ile Arg Glu Asp Ala Val Trp Ile Asn Arg Ala
145                 150                 155                 160

Lys Ser Phe Tyr Ser Met Asn Pro Cys Pro Thr Lys Asp Glu Val Trp
                165                 170                 175

Lys Ile Leu Ser Tyr Val Leu Asn Thr Ser Phe Leu Asp Leu Ser Leu
            180                 185                 190

Asn Asp Ser Ser Glu Arg Asp Asn Thr Lys Asn Lys Lys Gly Thr Lys
        195                 200                 205

Glu Asn Glu Lys Asp Val Ser Asn Lys Ser Lys Glu Leu Tyr Gly Trp
    210                 215                 220

Leu Phe Thr Lys Asn Pro Asn Lys Met Arg Glu Ala Gly Glu Asn Lys
225                 230                 235                 240

Asp Lys Phe Ile Asn Asn Phe Arg Glu Asn Phe Asn Thr Phe Thr Asp
                245                 250                 255

```
Tyr Ala Asn Leu Lys Val Glu Ile Glu Leu Trp Arg Lys Asn Asn Ile
            260                 265                 270

Ser Asn Thr Leu Leu Ile Thr Gln Lys Ala Lys Tyr Pro Pro Glu Val
        275                 280                 285

Lys Glu Ala Asn His Pro Ser Lys Phe Ser Val Gly Tyr Arg Lys Leu
    290                 295                 300

Leu Val His Leu Glu Leu Trp Pro Ser Ser Lys Asp Glu Asn Gly Asp
305                 310                 315                 320

Ile Pro Lys Gly Ile Glu Gly Lys Asp Lys Ser His Asn Gln Ile Leu
                325                 330                 335

Leu Asp Tyr Leu Leu Glu Val Cys Asn Glu Gly Asn Lys Thr Thr Lys
            340                 345                 350

Lys Val Ile Val Pro Ala Trp Ala Asp Gly Ile Lys Thr Glu Leu Glu
        355                 360                 365

Ser Lys Ala Ser Ile Lys Val Gly Asp Ser Thr Ser Ser Val Leu Gln
    370                 375                 380

Arg Leu Met Ile Lys Met Ala Ala Arg Arg Ile Ser Gln Thr Leu Ser
385                 390                 395                 400

Trp Ile Lys Ile Asn Glu Gln Val Arg His Asp Ala Tyr Gln Lys Lys
                405                 410                 415

Asn Lys Ala Phe Lys Leu Leu Cys Glu Ile Asp Lys Asn Gly Glu Ala
            420                 425                 430

Cys Lys Trp Leu Glu Asn Tyr Glu Leu Phe Arg Arg Asp Ser Gly
        435                 440                 445

Gly Glu Glu Tyr His Ile Ser Ala Arg Ala Ile Ser Cys Trp Lys Gln
    450                 455                 460

Ile Leu Glu Glu Trp Gln Lys Asn Asp Ser Ser Lys Ala Leu Arg Glu
465                 470                 475                 480

Lys Val Lys Val Val Gln Ala Ala Glu Asp Lys Phe Gly Asp Ala Arg
                485                 490                 495

Leu Phe Glu Asp Leu Ala Asp Asp Asn Ala Arg Ser Val Trp Leu Leu
            500                 505                 510

Pro Asp Gly Asn Lys Thr Pro Asp Ile Leu Asn Trp Trp Cys Glu Tyr
        515                 520                 525

Arg Thr Ala Asp Ile Asp Glu Ser Arg Phe Lys Ile Pro Cys Tyr Cys
    530                 535                 540

His Pro His Pro Phe Lys His Pro Val Tyr Val Glu Tyr Gly Lys Ser
545                 550                 555                 560

Asn Pro Gln Val Ile Phe Ser Leu Lys His Asp Lys Ala Arg Lys Asn
                565                 570                 575

Arg Ile Asp Asn Gly Trp Asn Pro Lys Asn Pro Arg Ile Leu Ala Leu
            580                 585                 590

Leu Leu Leu Asp Ile Val Arg Gln Lys Ser Thr Leu Ala Pro Phe Val
        595                 600                 605

Trp Glu Ser Lys Arg Leu Trp Lys Asp Leu Gly Gly Asp Ala Thr Val
    610                 615                 620

Thr Tyr Lys Ile Pro Arg Ser Asp Arg Met Gly Leu Ser Ser Ile Gly
625                 630                 635                 640

Asn Ile Asp Tyr Ala Arg Pro Glu Val Pro Phe Leu Lys Glu Lys Trp
                645                 650                 655

Asn Ala Arg Leu Gln Ser Asp Arg Arg Thr Leu Glu Lys Leu Glu Lys
            660                 665                 670

Tyr Trp Asn Pro Glu Ser Met Lys Trp Ile Asp Asp Gly Lys Phe Leu
```

```
                675                 680                 685
Ile Gln Ser Lys Trp Phe Ile Thr Phe Gly Pro Asp Met Glu Thr Ala
        690                 695                 700
Glu Gly Pro Trp Lys Leu Tyr Leu Lys Glu Asn Ile Asn Asp Asn Asn
705                 710                 715                 720
Tyr Leu Gly Asn Arg Ser Lys Glu Asn Gln Lys Arg Gly Tyr Arg Ala
                725                 730                 735
Lys Lys Leu Leu Ser Gly Tyr Pro Ala Gly Met Arg Ile Leu Ser Val
        740                 745                 750
Asp Leu Gly His Arg Tyr Ala Ala Ser Cys Ala Ile Trp Glu Thr Ile
        755                 760                 765
Thr Lys Lys Gln Ile Thr Glu Glu Leu Ala Tyr Gln Pro Asp Lys Asn
770                 775                 780
Ser Val Phe Glu His Ser Cys Lys Thr Ile Asp Lys Lys Ile Lys Asn
785                 790                 795                 800
Thr Val Tyr Arg Arg Ile Gly Asp Asp Ser Ile Asp Ala Pro Trp Ala
                805                 810                 815
Lys Leu Glu Lys Gln Phe Thr Ile Lys Leu Gln Gly Glu Asp Lys Ser
        820                 825                 830
Cys Tyr Leu Leu Arg Ser Asp Glu Lys Glu Leu Phe Arg Ser Ile Leu
        835                 840                 845
Ser Lys Leu Ser Cys Leu Asn Asn Asp Thr Gly His Asn Ile Leu Glu
850                 855                 860
Met Ile Glu Asn Leu Leu Arg Ile Val Lys Ala Lys Ile Tyr Arg Gln
865                 870                 875                 880
Gly Ile Leu Ala Arg Ile Ser Tyr Ser Met Thr Ala Gln Tyr Lys Pro
                885                 890                 895
Gly Lys Gly Gly Gln Lys Ser Pro Leu Ser Asp Glu Lys Ile His
        900                 905                 910
Tyr Leu Ser Glu Asn Leu Ala Ala Trp Ser Ala Leu Met Gly Asn Gln
        915                 920                 925
Glu Trp Asn Glu Asp Gly Ile Ser Asp Trp Tyr Lys Lys Tyr Ile Ser
        930                 935                 940
His Leu Val Ser Gly Pro Lys Pro Lys Glu Gly Asn Arg Lys Ser Asp
945                 950                 955                 960
Arg Asp Lys Ile Ile Glu Tyr Phe Leu Pro Ala Ala Arg Lys Leu Tyr
                965                 970                 975
Asp Asp Asn Glu Thr Arg Ile Asn Ile His Asp Leu Phe Lys Glu Leu
                980                 985                 990
Trp Asp Glu Asn Asn Lys Gln Leu Ser Ala Val Leu Lys Glu Ile Lys
        995                 1000                1005
Lys Ile Ile Leu Pro Lys Gly Ile Arg Tyr Phe Asp Lys Asn Asn
        1010                1015                1020
Asp Ser Ser Ser Arg Trp Lys Asn Asn Gln Ser Lys Leu Lys Gln
        1025                1030                1035
Ile Thr His Arg Gly Gly Leu Ser Leu Arg Arg Ile Val Ala Ile
        1040                1045                1050
Glu Gly Tyr Tyr Lys Leu Ala Lys Ala Tyr Lys Asn His Pro Glu
        1055                1060                1065
Pro Asp Asn Leu Thr Lys Ile Pro Leu Pro Gly Asp Asn Ser
        1070                1075                1080
Ser Ala Gly Phe Asn Gln Arg Ile Arg Asp Thr Leu Glu Arg Met
        1085                1090                1095
```

-continued

| | | | | | | | | | | |
|---|---|---|---|---|---|---|---|---|---|---|
| Lys | Glu | Gln | Arg | Val | Lys | Gln | Ile | Ala | Ser | Arg | Ile | Val | Glu | Ser |
| | 1100 | | | | 1105 | | | | 1110 | |

Lys Glu Gln Arg Val Lys Gln Ile Ala Ser Arg Ile Val Glu Ser
　　　　1100　　　　　　　1105　　　　　　　1110

Ala Leu Gly Leu Gly Ile Glu Gly Tyr Lys Lys Arg Pro Leu Thr
　　　　1115　　　　　　　1120　　　　　　　1125

Pro Glu Ser Lys Pro Cys Gln Ala Ile Val Ile Glu Asp Leu Ser
　　　　1130　　　　　　　1135　　　　　　　1140

His Tyr Arg Pro Asp Glu Leu Gln Thr Arg Arg Glu Asn Arg Arg
　　　　1145　　　　　　　1150　　　　　　　1155

Leu Met Gln Trp Ser Ser Ser Lys Val Lys Lys Tyr Leu Ser Glu
　　　　1160　　　　　　　1165　　　　　　　1170

Ala Cys Glu Met His Asp Val Leu Leu Val Glu Ile Ser Pro Glu
　　　　1175　　　　　　　1180　　　　　　　1185

Tyr Thr Ser Arg Gln Asp Ser Arg Thr Gly Val Ala Gly Leu Arg
　　　　1190　　　　　　　1195　　　　　　　1200

Cys Ile Asp Ile Asn Ile Arg Glu Phe Leu Lys Asp Ser Ser Ser
　　　　1205　　　　　　　1210　　　　　　　1215

Trp Gln Asn Lys Ile Lys Thr Ile Gln Met Lys Pro Thr Asn Lys
　　　　1220　　　　　　　1225　　　　　　　1230

Lys Ser Asn Leu Asp Gln Tyr Leu Ile Glu Leu Asn Glu Ser Leu
　　　　1235　　　　　　　1240　　　　　　　1245

Gly Glu Arg Tyr Lys Asp Lys Val Ile Pro Ser Asp Lys Phe Val
　　　　1250　　　　　　　1255　　　　　　　1260

Arg Ile Pro Arg Lys Gly Gly Asp Ile Phe Val Ser Ser Ser Lys
　　　　1265　　　　　　　1270　　　　　　　1275

Glu Ser Pro Val Ser Lys Gly Ile Gln Ala Asp Leu Asn Ala Ala
　　　　1280　　　　　　　1285　　　　　　　1290

Ala Asn Ile Gly Leu Lys Ala Leu Leu Asp Pro Asp Trp Ala Gly
　　　　1295　　　　　　　1300　　　　　　　1305

Ala Trp Trp Tyr Ile Leu Ile Glu Ala Lys Ser Asn His Val Ile
　　　　1310　　　　　　　1315　　　　　　　1320

Pro Tyr Gly Lys Lys Tyr Lys Gly Ala Glu Cys Leu Arg Asp Phe
　　　　1325　　　　　　　1330　　　　　　　1335

Lys Phe Ser Gly Leu Glu Asn Gln Val Met Lys Asn Asn Met Asn
　　　　1340　　　　　　　1345　　　　　　　1350

Leu Trp Arg Asp Leu Gln Ser Gln Phe Ser Ser Glu Asp Lys Trp
　　　　1355　　　　　　　1360　　　　　　　1365

Met Ser Tyr Lys Glu Tyr Asn Glu Leu Thr Glu Lys Arg Val Ile
　　　　1370　　　　　　　1375　　　　　　　1380

Asn Ile Leu Arg Glu Arg Ala Gly Leu Glu Leu Ile Glu Glu
　　　　1385　　　　　　　1390　　　　　　　1395

<210> SEQ ID NO 8
<211> LENGTH: 36
<212> TYPE: DNA
<213> ORGANISM: Artificial Sequence
<220> FEATURE:
<223> OTHER INFORMATION: CR RNA FOR ENGINEERED NUCLEASE

<400> SEQUENCE: 8
gtttaagtag atactactaa aaagaccgat ggacac                                    36

<210> SEQ ID NO 9
<211> LENGTH: 74
<212> TYPE: DNA
<213> ORGANISM: Artificial Sequence
<220> FEATURE:

<223> OTHER INFORMATION: TRACR RNA FOR ENGINEERED NUCLEASE

<400> SEQUENCE: 9

```
gggaagggcc tatttcccag catgtgtctt cgcatttaat tgctttagca ctgggcatcg    60
ttcttttag tagt                                                       74
```

<210> SEQ ID NO 10
<211> LENGTH: 1097
<212> TYPE: PRT
<213> ORGANISM: Artificial Sequence
<220> FEATURE:
<223> OTHER INFORMATION: ENGINEERED NUCLEASE

<400> SEQUENCE: 10

```
Met Val Thr Arg Ala Leu Asn Leu Lys Leu Val Val Pro Arg Arg Pro
1               5                   10                  15

Gly Glu Leu Thr Lys Ala Glu Ala Leu Trp Ser Thr His Asp Ile Val
            20                  25                  30

Asn Arg Ala Thr Ser Tyr Tyr Glu Ser Gln Leu Leu Cys Arg Gln
        35                  40                  45

Gln Asp Tyr Gln Thr Arg Glu Leu Thr Val Ser Ala Gly Asp Gln Ala
    50                  55                  60

Pro Asp Leu Asp Ala Leu Ile Ala Asn Ala Arg Asp Arg Asn Arg Tyr
65                  70                  75                  80

Arg Gly Leu Glu Lys Pro Gln Val Val Arg Glu Lys Leu Arg Asn Leu
                85                  90                  95

Tyr Glu Ala Ile Val Pro Pro Ala Ile Gly Lys Thr Gly Thr Ala Gln
            100                 105                 110

Ala Val Gly Ala Phe Val Ser Pro Leu Leu Asp Ala Asp Ser Arg Gly
        115                 120                 125

Phe Thr Glu Ile Phe Asp Lys Ile Glu Ala Leu Pro Asn Trp Val Asp
    130                 135                 140

Gly Val Arg Ala Glu Glu Pro Asp Ala Leu Glu Ala Ala Ala Asp Trp
145                 150                 155                 160

Leu Lys Ser Pro Gln Gly Lys Glu Arg Leu Arg Pro Thr Gly Ala Pro
                165                 170                 175

Pro Thr Trp Ile Lys Leu Ala Lys Lys Asp Ala Gly Trp Ala Ala
            180                 185                 190

Ala Phe Val Ala Asp Ile Asp Lys Leu Lys Glu Val Glu Gly Thr
        195                 200                 205

Pro Thr Leu Met Gln Glu Leu Arg Ala Leu Gly Val Met Pro Leu Phe
    210                 215                 220

Pro Ser Phe Phe Ala Ser Arg Ile Ala Gly His Lys Gly Ala Val Ser
225                 230                 235                 240

Thr Trp Asp Arg Leu Ala Leu Arg Leu Ala Val Ala His Leu Leu Ser
                245                 250                 255

Trp Glu Ser Trp Val Glu Leu Ala Ala Lys Glu His Ala Ala Arg Val
            260                 265                 270

Ala Lys Leu Glu Lys Phe Arg Asp Asp Asn Ile Leu Gly Glu Ile Ala
        275                 280                 285

Asp Ala Val Glu Ala Leu Leu Tyr Glu Lys Glu Arg Thr Glu Glu
    290                 295                 300

Leu Gln Gln Lys Ala Gln Leu Asp Ala Glu Glu Val Arg Thr Thr Ser
305                 310                 315                 320

Arg Thr Ile Arg Gly Trp Val Asp Leu Arg Glu Lys Trp Leu Lys Thr
```

```
                      325                 330                 335
Asp Ala Ser Pro Asp Ala Leu Ile Ser Leu Val Ala Ala Glu Gln Lys
                340                 345                 350

Arg Lys Ser Gly Lys Phe Gly Asp Pro Gln Leu Phe Arg Trp Leu Ala
            355                 360                 365

Lys Pro Glu Asn His Phe Val Trp Asn Lys Pro Asp Phe Asp Pro Pro
        370                 375                 380

Ser Leu Phe Ala Ser Leu Arg Met Ile Glu Gly Leu Val Glu Arg Ser
385                 390                 395                 400

Lys Glu Thr Ala Trp Met Thr Leu Pro Asp Ala Arg Leu His Pro Arg
                405                 410                 415

Ser Ser Gln Trp Glu Pro His Gly Gly Asn Leu Lys Thr Phe Arg
            420                 425                 430

Leu Glu Gln Gly Glu Gly Gly Ser Leu Ser Val Thr Leu Pro Leu Leu
                435                 440                 445

Arg Lys Ser Gly Asp Asp Ser Tyr Val Glu Glu His Ala Phe Ser
450                 455                 460

Leu Ala Gly Ser Lys Gln Ile Pro Asn Ala Ser Leu Asp Val Arg Arg
465                 470                 475                 480

Asn Lys Tyr Cys Leu Ser Tyr Arg Thr Pro Thr Gly Glu Glu Ala Glu
                485                 490                 495

Ala Val Val Gly Ser Ala Asp Leu Leu Leu Asp Trp Tyr Phe Leu Gln
            500                 505                 510

Gln Arg Ser Glu His Arg Pro Glu Glu Gly Asp Ile Gly Pro Ala Phe
        515                 520                 525

Leu Lys Leu Ala Leu Asp Ile Thr Pro Ile Asp Pro Val Trp Gly Glu
    530                 535                 540

Arg Glu Lys Thr Pro Ala Ile His His Phe Lys Thr Ala Ser Gly Lys
545                 550                 555                 560

Asn Thr Arg His Ala Asp Gly Val Ala Pro Gly Phe Arg Met Leu Ala
                565                 570                 575

Val Asp Leu Gly Ile Arg Thr Leu Ala Thr Cys Ser Val Phe Glu Leu
            580                 585                 590

Lys Ala Thr Ala Pro Ala Gly Arg Leu Ser Phe Pro Ile Ala His Leu
        595                 600                 605

Asp Leu His Ala Val His Glu Arg Ser Phe Thr Leu Thr Leu Asp Gly
    610                 615                 620

Glu Asp Pro Asp Arg Asp Ala Glu Arg Trp Arg Glu Asn Lys Ser Ala
625                 630                 635                 640

Glu Leu Arg Arg Leu Arg Met Gly Leu Thr Arg Tyr Arg Asn Ile Arg
                645                 650                 655

Asn Met Arg Glu Asp Ala Pro Asp Glu Arg Val Leu Leu Glu Asp
            660                 665                 670

Leu Gln Glu Lys Val Gln Glu His Gly Trp Ala Phe Glu Glu Pro Leu
        675                 680                 685

Leu Arg Glu Leu Ala Lys His Lys Asp Thr Pro Glu Pro Ile Trp Glu
    690                 695                 700

Ala Glu Leu Thr Lys Ala Leu Ala Gln Phe Arg Ser Asp Phe Gly Val
705                 710                 715                 720

Ile Val Gly Glu Trp Arg Arg Ser Asn Arg Ala Arg Ser Thr Asp Ser
                725                 730                 735

His Ala Gly Lys Ser Met Trp Ala Ile Asp His Leu Thr Asn Ser Arg
            740                 745                 750
```

-continued

Arg Phe Leu Met Ser Trp Ser Leu Leu Ser Lys Pro Gly Gln Ile Arg
             755                 760                 765

Arg Leu Asp Arg Asp Lys Gln Gly Val Phe Ala Lys His Leu Leu Asp
         770                 775                 780

His Leu Glu Gly Leu Lys Ala Asp Arg Leu Lys Thr Gly Ser Asp Leu
785                 790                 795                 800

Ile Val Gln Ala Ala Arg Gly Phe Arg Arg Asp Lys Arg Gly Asn Trp
                 805                 810                 815

His Lys Ala Tyr Lys Pro Cys His Gly Ile Leu Phe Glu Asp Leu Ser
             820                 825                 830

Arg Tyr Arg Met Arg Thr Asp Arg Pro Arg Arg Glu Asn Ser Gln Leu
         835                 840                 845

Met Lys Trp Ala His Arg Ala Val Pro Lys Glu Val Gly Met Gln Ala
850                 855                 860

Glu Val Tyr Gly Ile Arg Val Glu Asp Thr Gly Ala Ala Phe Ser Ser
865                 870                 875                 880

Arg Phe His Ala Ala Ser His Thr Pro Gly Ile Arg Met His Pro Ile
                 885                 890                 895

Cys Gln Lys Asp Leu Glu Asn Glu Trp Leu Leu Asp Glu Ile Glu Lys
                 900                 905                 910

Gln Asn Ser Gly Val Lys Arg Arg Glu Leu Lys Leu Gly Gln Leu Val
             915                 920                 925

Gln Leu Asn Gly Gly Glu Leu Phe Ala Cys Val Thr Ala Ser Gly Val
         930                 935                 940

Lys Thr Leu His Ala Asp Ile Asn Ala Ala Gln Asn Leu Gln Arg Arg
945                 950                 955                 960

Phe Phe Thr Arg His Gly Asp Ala Phe Arg Ile Val Ala Arg Lys Val
                 965                 970                 975

Leu Val Asp Glu Glu Glu Val Trp Val Pro Arg Ser Leu Gly Lys Arg
             980                 985                 990

Leu Leu Gly Ala Leu Gly Ser His  Gly Lys Leu Val Pro  Thr Gly His
         995                 1000                1005

Glu Ser  Gly Ser Cys Arg Phe  Glu Glu Ile Thr Thr  Arg Ala Trp
    1010                 1015                 1020

Ser Lys  Leu Ser Gly Glu Lys  Leu Ser Asp Asp Arg  Val Gly Asn
    1025                 1030                 1035

Glu Glu  Asp Gln Ile Ile Ala  Ser Ile Glu Gly Glu  Ala Leu Glu
    1040                 1045                 1050

Arg Thr  Gly Glu Val Val Val  Phe Phe Arg Asp Pro  Ser Gly Gln
    1055                 1060                 1065

Val Leu  Pro Arg Asp Leu Trp  Tyr Pro Ser Lys Thr  Phe Trp Ser
    1070                 1075                 1080

Ile Val  Lys Ser Thr Thr Leu  Ser Lys Leu Lys Ala  Ala Pro
    1085                 1090                 1095

<210> SEQ ID NO 11
<211> LENGTH: 36
<212> TYPE: DNA
<213> ORGANISM: Artificial Sequence
<220> FEATURE:
<223> OTHER INFORMATION: CR RNA FOR ENGINEERED NUCLEASE

<400> SEQUENCE: 11
ggtgaagtca cccccgttttt gtaggcctac tggcac                                    36

-continued

<210> SEQ ID NO 12
<211> LENGTH: 98
<212> TYPE: DNA
<213> ORGANISM: Artificial Sequence
<220> FEATURE:
<223> OTHER INFORMATION: TRACR RNA FOR ENGINEERED NUCLEASE

<400> SEQUENCE: 12

```
atgtaaccct ataggggttg cgtgagtcgg ccatagtgcc tcggcaacag cgtaaaaaac    60
tgctgccagt ggtcgaagta agtcaacaaa acggaggt                            98
```

<210> SEQ ID NO 13
<211> LENGTH: 1500
<212> TYPE: PRT
<213> ORGANISM: Artificial Sequence
<220> FEATURE:
<223> OTHER INFORMATION: ENGINEERED NUCLEASE

<400> SEQUENCE: 13

```
Met Ala Thr Ala Ile Asn Tyr Pro Thr Thr Gln Arg Ala Tyr Thr Leu
1               5                   10                  15

Arg Leu Arg Gly Ile Asp Pro Gln Asp Gln Ser Trp Arg Asp Ala Leu
            20                  25                  30

Trp Ala Thr His Glu Ala Val Asn Arg Gly Ala Lys Val Phe Gly Glu
        35                  40                  45

Trp Leu Leu Thr Leu Arg Gly Gly Leu Asp His Gln Leu Ala Asp Ala
    50                  55                  60

Pro Val Lys Val Arg Gly Gly Thr Thr Arg Leu Pro Ser Asp Glu Glu
65                  70                  75                  80

Arg Arg Asp Arg Arg Val Leu Leu Ala Leu Ser Trp Leu Ser Val Glu
                85                  90                  95

Asp Ala His Gly Ala Pro Pro Asp Ala Ser Leu Ile Val Ala Lys Gly
            100                 105                 110

Thr Asp Ser Ala Asp Cys Arg Ala Arg Lys Leu Ala Asp Ala Leu Ile
        115                 120                 125

Ala Ile Leu Gln Ala Arg Ser Val Ala Ala Ser Glu Ile Gly Asp Pro
    130                 135                 140

Ser Lys Pro Pro Glu Asp Gln Pro Gly Thr Trp Leu Gly Asp Cys Met
145                 150                 155                 160

Gly Ser Leu Ser Ala Ala Ile Arg Asp Asp Ala Val Trp Val Asn Arg
                165                 170                 175

Ser Lys Ala Phe Asp Ala Ala Thr Gln Ser Cys Pro Ser Leu Thr Arg
            180                 185                 190

Asp Glu Ile Trp Asp Phe Leu Glu Pro Phe Phe Ala Ser Pro Asp Ala
        195                 200                 205

Tyr Leu Lys Pro Glu Arg Ala Glu Ser Asp Glu Gly Asp Ser Thr Ser
    210                 215                 220

Ala Ala Thr Glu Asp Lys Ala Lys Asp Leu Val Gln Lys Ala Gly Gly
225                 230                 235                 240

Trp Leu Ser Lys Arg Met Gly Ala Gly Gly Ala Asn Phe Gln Asp
                245                 250                 255

Leu Ala Arg Ala Tyr Gln Ala Ile Ala Gln Trp Ala Ser Ala Gln
            260                 265                 270

Pro Gly Gln Ser Ala Gln Gln Ala Val Gly Ser Leu Ala Gly Tyr Leu
        275                 280                 285

Ser Gln His Gly Phe Ser Pro Thr Ala Asn Asp Ala Thr Gly Val Leu
```

```
                290                 295                 300
Ala Val Ile Ser Gly Pro Gly Tyr Lys Ser Ala Thr Arg Asn His Ile
305                 310                 315                 320

Thr Ala Ile Ala Thr Ser Pro Glu Ile Thr Pro Gln Asp Leu Ser Lys
                325                 330                 335

Leu Gln Glu Leu Ala Thr Lys Asp Lys Ala Gly Cys Ser Ser Lys Ile
                340                 345                 350

Gly Gly Lys Gly Pro Arg Pro Tyr Ala Thr Met Ile Leu Gln Gln Val
                355                 360                 365

Glu Ala Ala Cys Gly Phe Thr Tyr Leu Gln Ser Asp Gly Pro Ala Arg
370                 375                 380

His Arg Glu Phe Ser Val Met Leu Asp His Ala Ala Arg Arg Val Asn
385                 390                 395                 400

Val Ala His Ser Trp Ile Lys Asn Ala Glu Ala Glu Arg Arg Gln Phe
                405                 410                 415

Glu Ser Asp Ala Arg Arg Ile Lys Lys Val Pro Gln Asp Ala Leu Asn
                420                 425                 430

Trp Leu Arg Gly Tyr Cys Glu Glu Arg Gly Gly Ala Ser Gly Ser Leu
                435                 440                 445

Glu Gly Tyr Arg Ile Arg Arg Arg Ala Ile Asp Gly Trp Asp Gln Val
                450                 455                 460

Val Ile Arg Trp Ser Arg Ser Asp Cys Gln Ser Ala Asp Asp Arg Ile
465                 470                 475                 480

Ala Ala Ala Arg Gln Leu Gln Asp Asp Pro Glu Ile Asp Lys Phe Gly
                485                 490                 495

Asp Ile Gln Leu Phe Glu Ala Leu Ala Ala Glu Glu Ala Leu Cys Val
                500                 505                 510

Trp Lys Pro Asp Gly Asn Pro Thr Ala Gln Pro Leu Lys Asp Phe Val
                515                 520                 525

Ala Ala Thr Glu Ala Asp Ala Lys Lys Lys Arg Phe Lys Val Pro Ala
                530                 535                 540

Tyr Arg His Pro Asp Pro Leu Arg His Pro Val Phe Thr Asp Phe Gly
545                 550                 555                 560

Asn Ser Arg Trp Gly Ile Glu Tyr Ser Ala His Arg Ala Pro Ala Lys
                565                 570                 575

Cys Asp Glu Leu Gly Gln Gln Val Asp Arg Leu Thr Gln Ala Val Ala
                580                 585                 590

Glu Ala Gln Arg Asn Leu Asp Gly Ala Thr Ala Ala Gln Arg Ala Ser
                595                 600                 605

Arg Glu Ser Lys Leu Ala Glu Ala Gln Ser Lys Leu Val Ala Ala Gln
                610                 615                 620

Thr Glu Phe Ala Ala Ile Asn Asp Pro His Arg Val Glu Leu Lys Leu
625                 630                 635                 640

Trp Asn Gly Gln Ala Val Ala Ala Ile Pro Met Arg Trp Ser Ser Lys
                645                 650                 655

Arg Leu Ile Ala Asp Leu Ser Leu Arg Arg Ala Thr Gln Pro Ser Ser
                660                 665                 670

Asp Gln Arg Ile Gly Val Thr Arg Ala Asp Arg Leu Gly Arg Ala Ala
                675                 680                 685

Gly Asn Ala Asp Asp Gly Arg Pro Val Thr Ile Thr Gly Leu Phe Gln
                690                 695                 700

Gln Asp His Trp Asn Gly Arg Leu Gln Ala Pro Arg Ala Gln Leu Asp
705                 710                 715                 720
```

```
Ala Ile Ala Lys His Val Asp Lys His Gly Trp Asp Ala Lys Ala Arg
            725                 730                 735

Arg Gln Ile Ala Arg Ile Arg Trp Val Val Ser Phe Ser Ala Glu Leu
            740                 745                 750

Ser Gln Gln Gly Pro Trp Phe Glu Phe Cys His Arg Phe Gly Glu Asp
            755                 760                 765

Ala Pro Ala Arg Pro Phe Val Ser Arg His Gly Glu Tyr Ala Val Lys
            770                 775                 780

His Arg Asp Asn Asp Gln Arg Lys Gly His Ala Lys Leu Ile Leu Ser
785                 790                 795                 800

Arg Leu Pro Gly Leu Arg Val Leu Ala Val Asp Leu Gly His Arg Tyr
                    805                 810                 815

Ala Ala Ala Cys Ala Val Trp Glu Ala Ile Ser Ser Asp Gln Met Arg
                820                 825                 830

Gln Ala Cys Ala Ala Ala Asn Ala Pro Ala Pro His Pro Leu Ala Met
            835                 840                 845

Tyr Ile His Leu Lys Ser Thr Thr Ala Lys Gly Lys Pro Thr Thr Thr
            850                 855                 860

Ile Tyr Arg Arg Ile Gly Pro Asp Lys Leu Pro Asp Gly Thr Pro His
865                 870                 875                 880

Pro Ala Pro Trp Ala Arg Leu Asp Arg Gln Phe Leu Ile Lys Leu Pro
                    885                 890                 895

Gly Glu Asp Arg Pro Ala Arg Ala Ala Ser Pro Asp Glu Ile Lys Ala
                900                 905                 910

Val Glu Asp Phe Glu Asp Ser Val Gly Arg Val Arg Thr Ala Val Asp
            915                 920                 925

Pro Pro Arg Lys Arg Gly Val Asp Leu Leu Met His Asp Ala Val Arg
            930                 935                 940

Thr Ala Arg Leu Ala Leu Ala Arg His Gly Arg Ala Arg Ile Ala
945                 950                 955                 960

Phe Gln Leu Ile Ser Gln Val Arg Ile Leu Pro Gly Gly Arg Pro Gln
                    965                 970                 975

Thr Leu Asp Asp Ala Gly Arg Arg Asp Leu Leu Asn Thr Leu Ala
                980                 985                 990

Asp Trp Tyr Ala Leu Ala Thr Asp Ser Arg Trp Thr Asp Ala Ala Ala
            995                 1000                1005

Arg Gln Leu Trp Asn Glu Arg Leu Ala Ala Leu Asn Gly Gly Phe
    1010                1015                1020

Thr Ile Asp Pro Pro Ala Asp Ala Ser Gln Pro Glu Ala Glu Arg
    1025                1030                1035

Thr Arg Ala Gln Arg Arg Gln Ala Glu Gln Glu Leu Arg His Arg
    1040                1045                1050

Leu Ala Ser Leu Val Glu Ala Leu Phe Cys Asn Pro Thr Leu Cys
    1055                1060                1065

Gln Gln Leu His Gln Ala Trp Thr Asp Arg Trp Asn Ala Asp Asp
    1070                1075                1080

Gln Gln Trp Arg Ser Arg Leu Lys Trp Leu Ser Arg Trp Leu Leu
    1085                1090                1095

Pro Arg Gly Gly Ser Arg Arg Asp Gly Ser Arg Arg His Val Gly
    1100                1105                1110

Gly Leu Ser Leu Thr Arg Ile Ser Thr Leu Ile Asp Phe Arg Arg
    1115                1120                1125
```

```
Lys Val Gln Val Gly Tyr Phe Thr Arg Leu Arg Pro Asp Gly Ser
    1130              1135              1140

Arg Ala Glu Ile Gly Pro Gln Phe Gly Gln Ser Thr Leu Asp Ala
    1145              1150              1155

Ile Gln Arg Leu Lys Asp Gln Arg Ile Lys Gln Leu Thr Ser Arg
    1160              1165              1170

Ile Val Glu Ala Ala Leu Gly Ile Gly Val Glu Gln Asp Arg Ile
    1175              1180              1185

Trp Asp Ala Ala Lys Arg Lys Trp Arg Thr Val Lys Arg Pro Arg
    1190              1195              1200

Glu Pro Arg Tyr His Val Asp Asp Gln Gly Val Gln Gln Arg Asp
    1205              1210              1215

Pro Arg Phe Gln Ala Cys His Ala Val Val Ile Glu Asp Leu Ser
    1220              1225              1230

His Tyr Arg Pro Glu Glu Thr Arg Thr Arg Arg Glu Asn Arg Ala
    1235              1240              1245

Thr Met Asp Trp Lys Ser Ala Glu Thr Arg Lys Arg Leu Ala Asp
    1250              1255              1260

His Cys Gln Leu Tyr Gly Leu His Leu Arg Asp Val Asn Pro Gln
    1265              1270              1275

Tyr Thr Ser Arg Gln Asp Ser Arg Thr Gly Ala Pro Gly Cys Arg
    1280              1285              1290

Cys Val Asp Val Ser Val Ala Asp Phe Leu Thr Lys Pro Ala Trp
    1295              1300              1305

Arg Lys Gln Val Ala Gln Ala Arg Gly Lys Val Ala Ser Asn Arg
    1310              1315              1320

Gly Asp Ala Arg Asp Arg Leu Leu Val Glu Leu Asp His Gln Leu
    1325              1330              1335

Thr Thr Ala Asn Ser Leu Arg Gly Glu Met Asp Ser Leu Arg Ile
    1340              1345              1350

Pro Val Asn Gly Gly Glu Val Phe Val Ser Ala Asp Pro Arg Ser
    1355              1360              1365

Pro Leu Ala Ala Gly Ile Gln Ala Asp Leu Asn Ala Ala Ala Asn
    1370              1375              1380

Ile Gly Leu Arg Ala Leu Met Asp Pro Asp Phe Leu Gly Thr Trp
    1385              1390              1395

Trp Tyr Val Pro Cys Asp Pro Ser Thr Lys Lys Pro His Ile Glu
    1400              1405              1410

Lys Val Lys Gly Ser Ile Leu Ala Thr Val Gly Ala Leu Gln Ala
    1415              1420              1425

Thr Ser Glu Glu Ala Ala Ala Pro Pro Arg Arg Gly Arg Gly Gly
    1430              1435              1440

Thr Arg Ser Ala Ala Pro Arg Glu Val Ile Asn Leu Trp Arg Asp
    1445              1450              1455

Pro Ser Ala Val Arg Ile Gln Asp Ala Thr Ala Gly Glu Val Trp
    1460              1465              1470

Asp Val Thr Pro Val Tyr Trp Ser Ile Val Lys Asp Arg Val Val
    1475              1480              1485

Asp Val Leu Arg Gln Arg Asn Thr Lys Ser Gly Asp
    1490              1495              1500

<210> SEQ ID NO 14
<211> LENGTH: 36
<212> TYPE: DNA
```

```
<213> ORGANISM: Artificial Sequence
<220> FEATURE:
<223> OTHER INFORMATION: CR RNA FOR ENGINEERED NUCLEASE

<400> SEQUENCE: 14
ggcggcgaat cgccggcat ctcgatcgac cgacac                                    36

<210> SEQ ID NO 15
<211> LENGTH: 73
<212> TYPE: DNA
<213> ORGANISM: Artificial Sequence
<220> FEATURE:
<223> OTHER INFORMATION: TRACR RNA FOR ENGINEERED NUCLEASE

<400> SEQUENCE: 15
cggagggaac tccgtgaacg tgtcttcccc ttcgatgggc ttggcacacg gggtcaatcg         60
agttgccgtt gaa                                                            73

<210> SEQ ID NO 16
<211> LENGTH: 1479
<212> TYPE: PRT
<213> ORGANISM: Artificial Sequence
<220> FEATURE:
<223> OTHER INFORMATION: ENGINEERED NUCLEASE

<400> SEQUENCE: 16
```

Met Ser Gln Gln Val Lys Pro Pro Val Thr Gln Arg Ala Tyr Thr Leu
1               5                   10                  15

Arg Leu Arg Gly Ile Asp Pro Ser Asp Thr Ser Trp Arg Lys Ala Leu
            20                  25                  30

Trp Gln Thr His Glu Gly Val Asn Lys Gly Ala Lys Ala Phe Gly Asp
        35                  40                  45

Trp Leu Leu Thr Leu Arg Gly Gly Leu Asp His Thr Leu Ala Asp Thr
    50                  55                  60

Lys Val Lys Gly Gly Lys Gly Lys Pro Asp Arg Asp Pro Thr Asp Glu
65                  70                  75                  80

Glu Arg Lys Ala Arg Arg Ile Leu Leu Ala Leu Ser Trp Leu Ser Val
                85                  90                  95

Glu Ser Lys Leu Gly Ala Pro Val Gly Phe Ile Ile Ala Ser Gly Thr
            100                 105                 110

Glu Ala Ala Glu Asp Arg Asn Arg Lys Val Val Ala Ala Leu Glu Glu
        115                 120                 125

Ile Leu Lys Ser Arg Asn Val Ala Thr Asn Glu Ile Asp Gln Trp Lys
    130                 135                 140

Asn Asp Cys Ser Ala Ser Leu Ser Ala Ala Ile Arg Asp Asp Ala Val
145                 150                 155                 160

Trp Val Asn Arg Ser Lys Ala Phe Asp Glu Ala Val Lys Ser Ile Gly
                165                 170                 175

Ser Ser Leu Thr Arg Glu Glu Ala Trp Asp Met Leu Glu Arg Phe Phe
            180                 185                 190

Gly Ser Arg Asp Ala Tyr Leu Ala Pro Ala Lys Gly Ser Glu Asp Glu
        195                 200                 205

Ser Ser Glu Thr Glu Gln Glu Asp Lys Ala Lys Asp Leu Val Gln Lys
    210                 215                 220

Ala Gly Gln Trp Leu Ser Ser Arg Phe Gly Thr Gly Lys Gly Ala Asp
225                 230                 235                 240

Phe Cys Arg Met Ala Asn Val Tyr Gly Lys Ile Ala Ala Trp Ala Asp
                245                 250                 255

```
Asn Ala Gln Ala Asp Thr Thr Gly Asn Asp Ala Ile Asn Asn Leu Ala
            260                 265                 270

Ala Ala Leu Asn Glu Tyr Ser Pro Glu Pro Asn Asp Leu Lys Gly Val
        275                 280                 285

Leu Gly Leu Ile Ser Gly Pro Gly Tyr Lys Ser Ala Thr Arg Asn Leu
    290                 295                 300

Leu Asn Gln Leu Ala Ala Lys Ala Thr Val Thr Gln Gln Asp Phe Val
305                 310                 315                 320

Ser Leu Lys Asp Lys Ala Ser Asn Asp Ala Gln Lys Cys Lys Gln Asn
                325                 330                 335

Thr Gly Ser Lys Gly Pro Arg Pro Tyr Ser Asp Ala Ile Leu Lys Asn
            340                 345                 350

Val Glu Ser Val Cys Gly Phe Thr Tyr Leu Gln Asp Gly Gly Pro Ala
        355                 360                 365

Arg His Ser Glu Phe Ala Val Ile Leu Asp His Ala Ala Arg Arg Val
    370                 375                 380

Ser Leu Ala His Thr Trp Ile Lys Arg Ala Glu Ala Glu Arg Arg Lys
385                 390                 395                 400

Phe Glu Glu Asp Ala Lys Lys Ile Asp Gln Val Pro Lys Ala Ala Lys
                405                 410                 415

Asp Trp Leu Asp Ser Phe Cys Leu Glu Arg Ser Gly Ala Ser Gly Ala
            420                 425                 430

Leu Glu Pro Tyr Arg Ile Arg Arg Ala Val Asp Gly Trp Lys Glu
        435                 440                 445

Val Val Ala Ala Trp Ser Lys Ala Asp Cys Lys Thr Ala Glu Asp Arg
    450                 455                 460

Ile Ala Ala Arg Ala Leu Gln Asp Pro Glu Ile Asp Lys Phe
465                 470                 475                 480

Gly Asp Ile Gln Leu Phe Glu Ala Leu Ala Glu Asp Ala Val Cys
                485                 490                 495

Val Trp His Lys Asp Gly Asp Ala Ala Lys Pro Pro Asp Pro Gln Pro
            500                 505                 510

Leu Ile Asp Tyr Ala Leu Ala Ala Glu Ala Glu Phe Lys Lys Arg His
        515                 520                 525

Phe Lys Val Pro Ala Tyr Arg His Pro Asp Ala Leu Leu His Pro Val
    530                 535                 540

Phe Cys Asp Phe Gly Asn Ser Arg Trp Asp Ile Cys Phe Asp Val His
545                 550                 555                 560

Lys Asn Val Gln Thr Pro Phe Pro Arg Ala Leu Ser Leu Thr Leu Trp
                565                 570                 575

Thr Gly Ser Gly Met Val Ser Val Pro Leu Cys Trp Gln Ser Lys Arg
            580                 585                 590

Leu Ala Arg Asp Leu Ala Leu Gly Gln Asn Ala Gln Asn Asp Gly Ser
        595                 600                 605

Ser Glu Val Thr Arg Ala Asp Arg Leu Gly Arg Ala Ala Ser Asn Val
    610                 615                 620

Thr Lys Ser Asp Glu Val Lys Ile Ser Gly Leu Phe Glu Gln Glu Asp
625                 630                 635                 640

Trp Asn Gly Arg Leu Gln Ala Pro Arg Gln Gln Leu Glu Ala Ile Ala
                645                 650                 655

Ala Val Arg Asp Asn Leu Ser Leu Ser Asp Gln Glu Arg Glu Arg Arg
            660                 665                 670
```

-continued

```
Met Ser Gly Met Ile Asp Arg Ile Arg Trp Leu Val Thr Phe Ser Ala
            675                 680                 685

Lys Leu Gln Pro Gln Gly Pro Trp Cys Glu Phe Ala Glu Lys Ile Gln
    690                 695                 700

Ile Gly Ile Asn Pro Gln Tyr Trp Pro His Ala Asp Thr Asn Lys Asp
705                 710                 715                 720

Arg Lys Gly His Ala Arg Leu Ile Leu Ser Arg Leu Pro Gly Leu Arg
                725                 730                 735

Val Leu Ser Val Asp Leu Gly His Arg Tyr Ala Ala Cys Ala Val
            740                 745                 750

Trp Glu Ala Val Asn Ala Glu Gln Ile Asn Val Ala Cys Arg Ala Ala
            755                 760                 765

Gly His Arg Glu Pro Lys Ala Ser Asp Leu Tyr Leu His Leu Lys Arg
    770                 775                 780

Lys Thr Thr Lys Gln Lys Lys Gly Asp Gln Val Glu Phe Lys Glu Thr
785                 790                 795                 800

Thr Ile Tyr Arg Arg Ile Gly Ala Asp Thr Leu Pro Asp Gly Thr Pro
                805                 810                 815

His Pro Ala Pro Trp Ala Arg Leu Asp Arg Gln Phe Leu Ile Lys Leu
            820                 825                 830

Gln Gly Glu Glu Gly Val Arg Ala Ala Ser Asn Glu Glu Ile Trp
    835                 840                 845

Ala Val His Arg Leu Glu Val Glu Leu Gly Arg Thr Ala Pro Leu Ile
    850                 855                 860

Asp Arg Leu Val Lys Ala Gly Trp Gly Gln Ser Gly Lys Gln Lys Thr
865                 870                 875                 880

Arg Leu Asp Ala Leu Arg Asn Leu Gly Trp Ala Pro Ala Asn Glu Val
                885                 890                 895

Gln Gly Ser Asp Glu Met Asp Glu Gly Glu Val His Lys Pro Ser Leu
    900                 905                 910

Ser Val Asp Glu Leu Met Ser Ser Ala Val Arg Thr Met Arg Leu Ala
    915                 920                 925

Leu Lys Arg His Gly Asp Arg Ala Arg Ile Ala Phe Ala Met Thr Ala
    930                 935                 940

Ala Tyr Lys Pro Met Pro Gly Asp Arg Lys Tyr Tyr Phe Thr Glu Ala
945                 950                 955                 960

Lys Asp Ala Ser Ala Asn Glu Asp Ala Thr Ala Arg Asn Gly Lys His
                965                 970                 975

Ile Glu Phe Ile Gln Asp Ala Leu Leu Leu Trp Tyr Gly Leu Thr Ser
            980                 985                 990

Ser Arg Gly Trp Arg Asp Asp Ala Ala Arg Gln Leu Trp Asp Asp His
    995                 1000                1005

Ile Ala Lys Leu Ser Val Tyr Lys Ala Pro Glu Glu Ile Gly Glu
    1010                1015                1020

Asp Ala Ser Gly Val Glu Arg Lys Thr Lys Gln Lys Glu Asn Arg
    1025                1030                1035

Glu Lys Leu His Asp Val Ala Lys Ala Leu Ala Gln Asp Val Asn
    1040                1045                1050

Leu Arg Lys Val Leu His Asn Ala Trp Lys Lys Arg Trp Glu Lys
    1055                1060                1065

Asp Asp Glu Arg Trp Lys Lys Gln Leu Arg Trp Phe Lys Asp Trp
    1070                1075                1080

Val Phe Pro Arg Gly Lys His Ala Ser Asp Pro Ala Ile Arg Lys
```

```
              1085                1090                1095
Val  Gly  Gly  Leu  Ser  Leu  Pro  Arg  Leu  Ala  Thr  Leu  Ile  Glu  Phe
              1100                1105                1110
Arg  Arg  Lys  Val  Gln  Val  Gly  Phe  Phe  Thr  Arg  Leu  Gln  Pro  Asp
              1115                1120                1125
Gly  Thr  Arg  Ala  Glu  Thr  Lys  Glu  Gln  Phe  Gly  Gln  Ser  Ala  Leu
              1130                1135                1140
Asp  Thr  Leu  Glu  His  Leu  Arg  Glu  Gln  Arg  Val  Lys  Gln  Leu  Ala
              1145                1150                1155
Ser  Arg  Ile  Val  Glu  Ala  Ala  Leu  Gly  Ile  Gly  Arg  Val  Arg  Arg
              1160                1165                1170
Pro  Leu  Gly  Gly  Lys  Asp  Pro  Lys  Arg  Pro  Asp  Val  Arg  Val  Asp
              1175                1180                1185
Glu  Pro  Cys  His  Ala  Ile  Val  Ile  Glu  Asp  Leu  Thr  His  Tyr  Arg
              1190                1195                1200
Pro  Glu  Glu  Thr  Arg  Thr  Arg  Arg  Glu  Asn  Arg  Gln  Leu  Met  Thr
              1205                1210                1215
Trp  Ser  Ser  Ser  Lys  Val  Lys  Asp  Tyr  Leu  Ser  Glu  Ala  Cys  Gln
              1220                1225                1230
Leu  His  Gly  Leu  His  Leu  Arg  Glu  Val  Ser  Ala  Ser  Tyr  Thr  Ser
              1235                1240                1245
Arg  Gln  Asp  Ser  Arg  Thr  Gly  Ser  Pro  Gly  Ile  Arg  Cys  Gln  Asp
              1250                1255                1260
Val  Pro  Val  Lys  Glu  Phe  Met  Arg  Ser  Pro  Phe  Trp  Arg  Lys  Gln
              1265                1270                1275
Val  Ala  Gln  Ala  Glu  Lys  Lys  Gly  Asp  Ala  His  Glu  Arg  Phe  Leu
              1280                1285                1290
Cys  Glu  Leu  Asn  Ala  Met  Trp  Lys  Asp  Lys  Thr  Val  Ala  Asp  Trp
              1295                1300                1305
Glu  Lys  Ala  Gly  Ala  Val  Arg  Val  Pro  Leu  Lys  Gly  Gly  Glu  Val
              1310                1315                1320
Phe  Val  Ser  Ala  Asp  Arg  Ile  Ser  Pro  Ser  Ala  Lys  Gly  Leu  Gln
              1325                1330                1335
Ala  Asp  Leu  Asn  Ala  Ala  Ala  Asn  Ile  Gly  Leu  Arg  Ala  Leu  Thr
              1340                1345                1350
Asp  Pro  Asp  Trp  Pro  Gly  Lys  Trp  Trp  Tyr  Val  Pro  Cys  Glu  Pro
              1355                1360                1365
Ala  Ser  Phe  Arg  Pro  Ala  Lys  Asp  Lys  Val  Asp  Gly  Ser  Ala  Val
              1370                1375                1380
Val  Asn  Pro  Gly  Gln  Pro  Leu  Arg  Gln  Ser  Ala  Gln  Ala  Gln  Ser
              1385                1390                1395
Gly  Asp  Ala  Ala  Lys  Asp  Lys  Lys  Lys  Arg  Gly  Asn  Lys  Gly  Ala
              1400                1405                1410
Gly  Gln  Ser  Lys  Glu  Val  Val  Asn  Leu  Trp  Arg  Asp  Ile  Ser  Ser
              1415                1420                1425
Ser  Pro  Leu  Glu  Cys  Ile  Glu  Cys  Gly  Glu  Trp  Lys  Glu  Tyr  Ala
              1430                1435                1440
Ala  Tyr  Gln  Asn  Glu  Val  Gln  Tyr  Arg  Val  Ile  Arg  Ile  Leu  Glu
              1445                1450                1455
Glu  Gln  Ile  Lys  Gly  Arg  Asp  Arg  Gln  Pro  His  Glu  Gly  Ser  Arg
              1460                1465                1470
Glu  Asp  Asp  Ile  Pro  Phe
              1475
```

```
<210> SEQ ID NO 17
<211> LENGTH: 36
<212> TYPE: DNA
<213> ORGANISM: Artificial Sequence
<220> FEATURE:
<223> OTHER INFORMATION: CR RNA

<400> SEQUENCE: 17
gttgccgacg tcagcaccaa cctgatcgac ggacac                          36

<210> SEQ ID NO 18
<211> LENGTH: 93
<212> TYPE: DNA
<213> ORGANISM: Artificial Sequence
<220> FEATURE:
<223> OTHER INFORMATION: TRACR RNA FOR ENGINEERED NUCLEASE

<400> SEQUENCE: 18
ttgcctctac aggaggcgag aatgccacgg cacgtgtctt ccccttcaat gggcttggca   60
ccgtggagtc gatcagtttt gtgccggcga agg                              93

<210> SEQ ID NO 19
<211> LENGTH: 1481
<212> TYPE: PRT
<213> ORGANISM: Artificial Sequence
<220> FEATURE:
<223> OTHER INFORMATION: ENGINEERED NUCLEASE

<400> SEQUENCE: 19

Met Ala Arg Arg Ser Ala Ser Thr Ser Lys Pro Pro Gly Pro Val Ala
1               5                   10                  15

Pro Thr Thr Gln Arg Ala Tyr Thr Leu Arg Leu Arg Arg Ala Pro Gly
            20                  25                  30

Lys Cys Pro His Cys Glu Gln Asp Ala Cys Asp Cys Trp Arg Glu Ala
        35                  40                  45

Leu Trp Ala Thr His Ala Ala Phe Asn Arg Gly Ala Lys Ala Phe Gly
    50                  55                  60

Asp Trp Leu Leu Thr Leu Arg Gly Gly Leu Ser His Glu Leu Ala Glu
65                  70                  75                  80

Gln Pro Ser Pro Pro Lys Asn Lys Glu Pro Thr Cys Glu Glu Ser Asp
                85                  90                  95

Ala Ile Arg Lys Asn Arg Arg Ile Leu Leu Ala Leu Ser Trp Leu Ser
            100                 105                 110

Val Glu Asp Asp Cys Ser Ala Pro Thr Gly Thr Phe Arg Val Ala Ser
        115                 120                 125

Gly Lys Asp Ser Glu Ala Glu Arg Lys Asn Lys Val Leu Thr Ala Phe
    130                 135                 140

Arg Ser Ile Leu Thr Ala Arg Arg Met Arg Ser Gln Asp Val Glu Ser
145                 150                 155                 160

Trp Ile Ala Asp Cys Ala Ala Ser Leu Ser Ala Lys Ile Arg Glu Asp
                165                 170                 175

Ala Val Trp Ile Asn Arg Ser Ala Cys Phe Asp Gln Arg Ala Leu Asp
            180                 185                 190

Leu Lys Val Leu Ser Arg Glu Tyr Ala Lys Ala Ala Val Met Ser Phe
        195                 200                 205

Phe Gly Pro Leu Asp Glu Tyr Phe Lys Leu Pro Asp Glu Ala Asp Asp
    210                 215                 220
```

```
Thr Lys Pro Ala Val Gly Gly Asp Gly Pro Asp Phe Arg Thr Leu Ala
225                 230                 235                 240

Arg Gln Trp Val Ser Thr Asn Phe Gly Thr Gly Lys Lys Ser Asp Ser
            245                 250                 255

Glu Ala Ile Ala Gln Asn Leu Arg Lys Leu Ala Asp Ala Asn Leu Ala
        260                 265                 270

Pro Phe Ser Gly Lys Pro Lys Ala Ala Leu Ile Ala His Leu Ser Val
    275                 280                 285

Glu Leu Asp Gly Ser Thr Ala Asp Ile Asp Gly Leu Cys Arg Ala Ile
290                 295                 300

Gly Trp Asn Thr Gly Arg Pro Ser Lys Gly Arg Val Ala Ile Glu Arg
305                 310                 315                 320

Leu Pro Asp Pro Pro Thr Glu Thr Ser Ile Gln Thr Met Gln Gln Lys
                325                 330                 335

Phe Arg Glu Glu Ala Glu Ala Lys Ala Ser Ser Lys Gly Leu Arg Gln
            340                 345                 350

Val Pro Glu Trp Met Pro Ala Phe Gln Lys Ser Ile Glu Arg Asp Cys
        355                 360                 365

Gly Met Pro Phe Lys Leu Gly Glu Gly Arg Asp His Ile Gly Glu Phe
370                 375                 380

Ser Val Met Leu Asp His Ala Ala Arg Arg Val Ser Ile Gly His Ser
385                 390                 395                 400

Trp Ile Lys Arg Ala Glu Ala Glu Arg Arg Phe Glu Ala Asp Ala
                405                 410                 415

Gln Arg Leu Asn His Ile Pro Ala Ala Ala Lys Asp Trp Leu Asp Gln
            420                 425                 430

Phe Val Gln Phe Arg Ser Gly Ser Ser Gly Ala Ala Ala Gly Gly
        435                 440                 445

Glu Tyr Arg Ile Arg Arg Ala Ile Glu Gly Trp Asp Glu Ile Ile
    450                 455                 460

Lys Arg Trp Lys Arg Ala Ala Cys Lys Ser Pro Glu Asp Arg Val Ala
465                 470                 475                 480

Ala Ala Arg Glu Val Gln Ala Asp Pro Glu Ile Glu Lys Phe Gly Asp
                485                 490                 495

Ile Gln Leu Phe Glu Ala Leu Ala Ala Asp Ala Glu Cys Val Trp
            500                 505                 510

Arg Gly Asp Gly Asn Gly Thr Pro Asp Pro Leu Lys Asp Tyr Val Ala
        515                 520                 525

Ala Thr Asp Ala Leu Asp Lys Met Arg Arg Phe Lys Val Pro Ala Tyr
530                 535                 540

Arg His Pro Asp Pro Leu Ala His Pro Val Phe Gly Asp Phe Gly Asn
545                 550                 555                 560

Ser Arg Gly Asp Ile Arg Phe Ala Val His Glu Ala Ala Lys Ala Thr
                565                 570                 575

Arg Gly Thr Lys Arg Ile Ala Lys Asp Gln Lys Glu Trp Ile Arg Glu
            580                 585                 590

Arg His Gly Leu Arg Met Gly Leu Trp Asp Gly Gln Ser Val Arg Thr
        595                 600                 605

Ala Asp Leu Arg Trp Ser Ser Lys Arg Leu Val Asp Asp Leu Ala Leu
610                 615                 620

Arg Asn His Val Thr Thr Arg Arg Thr Gly Pro Val Ser Arg Ala Asp
625                 630                 635                 640

Arg Leu Gly Arg Ala Ala Ala Gly Leu Gly Ala Asp Glu Ala Ala Cys
```

-continued

```
                645                 650                 655
Val Ala Gly Leu Phe Glu Leu Pro Asp Trp Asn Gly Arg Leu Gln Ala
            660                 665                 670

Pro Arg Ala Gln Leu Asp Ala Ile Ala Ala Cys Val Ala Ala Asn Gly
            675                 680                 685

Gly Lys Trp Asp Asp Lys Ala Arg Lys Leu Arg Asp Arg Ile Glu Trp
            690                 695                 700

Leu Val Ser Phe Ser Ala Lys Leu Glu Cys Cys Gly Pro Phe Met Glu
705                 710                 715                 720

Tyr Ala Ser Gln Asn Gly Ile Gln Pro Asn Gly Lys Gly Glu Tyr Tyr
                725                 730                 735

Pro His Ala Glu Arg Asn Lys Gly Arg Thr Gly His Ala Lys Leu Ile
            740                 745                 750

Leu Ser Arg Leu Pro Gly Leu Arg Val Leu Ala Val Asp Leu Gly His
            755                 760                 765

Arg Phe Ala Ala Cys Ala Val Trp Glu Ala Leu Ser Lys Ile Ala
            770                 775                 780

Phe Asp Ala Glu Thr Lys Gly Arg Glu Val Val Ser Gly Gly Arg Ala
785                 790                 795                 800

Ala Asp Asp Leu Tyr Cys His Thr Arg His Leu Asp Cys Ala Gly Lys
                805                 810                 815

Ala Arg Thr Thr Ile Tyr Arg Ile Gly Pro Asp Lys Leu Pro Asp
            820                 825                 830

Gly Ser Asp His Pro Ala Pro Trp Ala Arg Leu Asp Arg Gln Phe Leu
            835                 840                 845

Ile Lys Leu Gln Gly Glu Glu Arg Pro Ala Arg Ala Ala Gly Pro Ala
850                 855                 860

Glu Thr Ala Ala Val Gln Gln Ile Glu Thr Asp Leu Gly Arg Ala Arg
865                 870                 875                 880

Gly Gln Glu Asp Leu Pro Pro Arg Pro Val Asp Ser Leu Met Arg Glu
                885                 890                 895

Ala Val Arg Thr Ile Arg Ile Ala Leu Arg Arg His Gly Asp Ala Ala
            900                 905                 910

Arg Ile Ala Tyr Ala Phe Lys Pro Gly Ala Lys Arg Leu Lys Pro Gly
            915                 920                 925

Gly Gly Ala Gln Asp His Thr Pro Glu Thr His Ala Asp Ala Ile Leu
            930                 935                 940

Glu Ala Leu Leu Arg Trp His Glu Leu Ala Thr Gly Ala Arg Trp Arg
945                 950                 955                 960

Asp Pro Trp Ala Glu Thr Gln Trp Lys Asp Trp Val Gln Pro His Ile
                965                 970                 975

Ser Ala Thr Leu Pro Glu Leu Ala Asn Asp Ala Asp Arg Trp Glu Arg
            980                 985                 990

Lys Arg His Arg Ala Ala Leu Glu Gln Val Leu Arg Pro Val Ala Gln
            995                 1000                1005

Met Leu Ile Gln Arg Pro Thr Asp Ala Leu His Gln Val Trp Ser
    1010                1015                1020

Lys His Trp Ala Asp Glu Asp Leu Lys Trp Pro Ser Arg Leu Arg
    1025                1030                1035

Trp Leu Arg Asn Trp Leu Leu Pro Arg Gly Pro Arg Ala Arg Ser
    1040                1045                1050

Gly Ala Ala Arg Asn Val Gly Gly Leu Ser Leu Leu Arg Ile Ala
    1055                1060                1065
```

```
Thr Leu Arg Glu Leu Tyr Gln Thr Gln Lys Ala Tyr Ala Met Arg
    1070            1075            1080

Pro Glu Pro Asp Asp Pro Arg Lys Arg Ile Ala Gly Arg Asn Asp
    1085            1090            1095

Asp Arg Tyr Asp Glu Leu Gly Arg Ser Val Leu Gln Val Ile Glu
    1100            1105            1110

Arg Leu Arg Glu Gln Arg Val Lys Gln Leu Ala Ser Arg Ile Val
    1115            1120            1125

Glu Ala Ala Leu Gly Val Gly Arg Ala Lys Pro Thr Arg Gly Arg
    1130            1135            1140

Gln Arg Pro Gln Ser Arg Val Asp Val Pro Cys His Ala Val Ile
    1145            1150            1155

Ile Glu Ser Leu Arg Asn Tyr Arg Pro Asp Glu Leu Gln Thr Arg
    1160            1165            1170

Arg Glu Asn Arg Ala Ile Met Asn Trp Ser Ala Gly Lys Val Arg
    1175            1180            1185

Lys Tyr Leu Glu Glu Ala Cys Gln Leu His Gly Leu His Leu Arg
    1190            1195            1200

Glu Val Met Pro Asn Tyr Thr Ser Arg Glu Asp Ser Arg Thr Gly
    1205            1210            1215

Leu Pro Gly Val Arg Cys Val Asp Val Pro Val Asp Pro Lys Leu
    1220            1225            1230

Gly Lys Pro Lys Ala Tyr Trp Trp Asn Ser Val Leu Ser Thr Ala
    1235            1240            1245

Arg Lys Lys Ser Ile Gly Asp Ala Ala Ser His Asp Lys Gln Gly
    1250            1255            1260

Asp Ala Thr Ser Arg Phe Ile Val Glu Leu Ala Gly Cys Leu Asp
    1265            1270            1275

Arg Leu Lys Ala Asp Gly Lys Pro Leu Pro Lys Thr Val Arg Val
    1280            1285            1290

Pro Arg Ile Gly Gly Asp Leu Phe Val Ala Ala Pro Pro Thr Ser
    1295            1300            1305

Cys Thr Ala Pro Ala His Gln Pro His Pro Ala Cys Asp Gly Ala
    1310            1315            1320

Arg Ala Leu Gln Ala Asp Leu Asn Ala Ala Ala Asn Ile Gly Leu
    1325            1330            1335

Arg Ala Leu Leu Asp Pro Asp Phe Pro Ala Lys Trp Trp Tyr Val
    1340            1345            1350

Pro Cys Ile Asp Asp Gln Arg Gly Leu Ala Leu Pro Arg Ala Asp
    1355            1360            1365

Lys Val Leu Gly Ser Ala Cys Phe Pro Gly Asp Pro Ala Thr Phe
    1370            1375            1380

Gly Ser Leu Leu Lys Thr Arg Thr Ala Ala Gly Pro Ala Val Asp
    1385            1390            1395

Gly Gln Ala Ala Pro Asp Arg Lys Pro Arg Thr Gly Thr His Arg
    1400            1405            1410

Pro Gly Ser Ala Lys Ser Arg Ser Leu Gly Asp Gly Lys Ala Thr
    1415            1420            1425

Thr Asn Tyr Trp Ser Asp Arg Ser Ala Arg Asp Leu Arg Pro Ala
    1430            1435            1440

Asp Glu Gly Gly His Trp Gln Pro Thr Asn Val Tyr Trp Asn Trp
    1445            1450            1455
```

```
Val Arg Lys Arg Ala Leu Leu Gly Leu Tyr Ser Phe Asn Gly Leu
1460                1465                    1470

Ser Pro Pro Ser Asp Asp Arg Pro
1475                1480
```

<210> SEQ ID NO 20
<211> LENGTH: 36
<212> TYPE: DNA
<213> ORGANISM: Artificial Sequence
<220> FEATURE:
<223> OTHER INFORMATION: CR RNA FOR ENGINEERED NUCLEASE

<400> SEQUENCE: 20
gccgcgtcgg ccgacgcggc cttgatcgat ggacac                         36

<210> SEQ ID NO 21
<211> LENGTH: 94
<212> TYPE: DNA
<213> ORGANISM: Artificial Sequence
<220> FEATURE:
<223> OTHER INFORMATION: ENGINEERED NUCLEASE

<400> SEQUENCE: 21
gtcgcctata gggcgataca actccgagca tgtgtcttcc ccttcaatgg gcttggcact    60
cggcatcgat caagctcgcg tcggctgtcg ggcc                               94

<210> SEQ ID NO 22
<211> LENGTH: 111
<212> TYPE: DNA
<213> ORGANISM: Artificial Sequence
<220> FEATURE:
<223> OTHER INFORMATION: TEST SGRNA

<400> SEQUENCE: 22
gggaagggcc tatttcccag catgtgtctt cgcatttaat tgctttagca ctgggcatcg    60 ttcttttag tagtgtttaa gtagatacta ctgaaaagac cgatggacac a             111

<210> SEQ ID NO 23
<211> LENGTH: 98
<212> TYPE: DNA
<213> ORGANISM: Artificial Sequence
<220> FEATURE:
<223> OTHER INFORMATION: TEST GRNA

<400> SEQUENCE: 23
gggaagggcc tatttcccag catgtgtctt cgcatttaat tgctttagca ctgggcatcg    60 ttcttttag aaaactactg aaaagaccga tggacaca                            98

<210> SEQ ID NO 24
<211> LENGTH: 83
<212> TYPE: DNA
<213> ORGANISM: Artificial Sequence
<220> FEATURE:
<223> OTHER INFORMATION: TEST SGRNA

<400> SEQUENCE: 24
gggaagggcc tatttcccag catgtgtctt cgcatttaat tgctttagca ctgggcatcg    60
ttctaaaaag accgatggac aca                                          83

<210> SEQ ID NO 25
<211> LENGTH: 97
<212> TYPE: DNA
<213> ORGANISM: Artificial Sequence -continued

<220> FEATURE:
<223> OTHER INFORMATION: TEST SGRNA

<400> SEQUENCE: 25
ggaagggcct atttcccagc atgtgtcttc gcatttaatt gctttagcac tgggcatcgt    60 tcttttttaga aaactactga aaagaccgat ggacaca    97

<210> SEQ ID NO 26
<211> LENGTH: 105
<212> TYPE: DNA
<213> ORGANISM: Artificial Sequence
<220> FEATURE:
<223> OTHER INFORMATION: TEST SGRNA

<400> SEQUENCE: 26
ggtccaaggg aagggcctat tcccagcat gtgtcttcgc atttaattgc tttagcactg    60
ggcatcgttc ttttagaaa actactgaaa agaccgatgg acaca    105

<210> SEQ ID NO 27
<211> LENGTH: 116
<212> TYPE: DNA
<213> ORGANISM: Artificial Sequence
<220> FEATURE:
<223> OTHER INFORMATION: TEST SGRNA

<400> SEQUENCE: 27
gccccgattt ccctttgaat gatctcggcc tcgttgccac tgaccgaatt cttccgcctt    60
tggaattcca agctctttga catcgcgagc ccgcgatggg aaagagattg tggcgg    116

<210> SEQ ID NO 28
<211> LENGTH: 114
<212> TYPE: DNA
<213> ORGANISM: Artificial Sequence
<220> FEATURE:
<223> OTHER INFORMATION: TEST SGRNA

<400> SEQUENCE: 28
gccccgattt ccctttgaat gatctcggcc tcgttgccac tgaccgaatt cttccgcctt    60
tggaattcca agctctttga catcgcgagc ccgcgatggg aaagagattg tggc    114

<210> SEQ ID NO 29
<211> LENGTH: 111
<212> TYPE: DNA
<213> ORGANISM: Artificial Sequence
<220> FEATURE:
<223> OTHER INFORMATION: TEST SGRNA

<400> SEQUENCE: 29
gatttccctt tgaatgatct cggcctcgtt gccactgacc gaattcttcc gcctttggaa    60
ttccaagctc tttgacatcg cgagcccgcg atgggaaaga gattgtggcg g    111

<210> SEQ ID NO 30
<211> LENGTH: 112
<212> TYPE: DNA
<213> ORGANISM: Artificial Sequence
<220> FEATURE:
<223> OTHER INFORMATION: TEST SGRNAV4

<400> SEQUENCE: 30
ggatttccct tgaatgatc tcggcctcgt tgccactgac cgaattcttc cgcctttgga    60
attccaagct ctttgacatc gcgagcccgc gatgggaaag agattgtggc gg    112

<210> SEQ ID NO 31
<211> LENGTH: 110
<212> TYPE: DNA
<213> ORGANISM: Artificial Sequence
<220> FEATURE:
<223> OTHER INFORMATION: TEST SGRNA

<400> SEQUENCE: 31
gggaagggcc tatttcccag catgtgtctt cgcatttaat tgctttagca ctgggcatcg     60 ttcttttag tagtgtttaa gtagatacta ctaaaaagac cgatggacac              110

<210> SEQ ID NO 32
<211> LENGTH: 96
<212> TYPE: DNA
<213> ORGANISM: Artificial Sequence
<220> FEATURE:
<223> OTHER INFORMATION: TEST SGRNA

<400> SEQUENCE: 32
gggaagggcc tatttcccag catgtgtctt cgcatttaat tgctttagca ctgggcatcg     60 ttcttttag taaaaactaa aaagaccgat ggacac                              96

<210> SEQ ID NO 33
<211> LENGTH: 84
<212> TYPE: DNA
<213> ORGANISM: Artificial Sequence
<220> FEATURE:
<223> OTHER INFORMATION: TEST SGRNA

<400> SEQUENCE: 33
gggaagggcc tatttcccag catgtgtctt cgcatttaat tgctttagca ctgggcatcg     60
ttcttaaaaa agaccgatgg acac                                          84

<210> SEQ ID NO 34
<211> LENGTH: 103
<212> TYPE: DNA
<213> ORGANISM: Artificial Sequence
<220> FEATURE:
<223> OTHER INFORMATION: TEST SGRNA

<400> SEQUENCE: 34
gggccaaggg aagggcctat ttcccagcat gtgtcttcgc atttaattgc tttagcactg     60 gcatcgttc tttttagtaa aaactaaaaa gaccgatgga cac                     103

<210> SEQ ID NO 35
<211> LENGTH: 91
<212> TYPE: DNA
<213> ORGANISM: Artificial Sequence
<220> FEATURE:
<223> OTHER INFORMATION: TEST SGRNA

<400> SEQUENCE: 35
gggccaaggg aagggcctat ttcccagcat gtgtcttcgc atttaattgc tttagcactg     60 gcatcgttc ttaaaaaaga ccgatggaca c                                   91

<210> SEQ ID NO 36
<211> LENGTH: 134
<212> TYPE: DNA
<213> ORGANISM: Artificial Sequence
<220> FEATURE:
<223> OTHER INFORMATION: TEST SGRNA

<400> SEQUENCE: 36

```
atgtaaccct atagggggttg cgtgagtcgg ccatagtgcc tcggcaacag cgtaaaaaac    60
tgctgccagt ggtcgaagta agtcaacaaa acggaggtgg tgaagtcacc cccgttttgt   120
aggcctactg gcac                                                      134

<210> SEQ ID NO 37
<211> LENGTH: 111
<212> TYPE: DNA
<213> ORGANISM: Artificial Sequence
<220> FEATURE:
<223> OTHER INFORMATION: TEST SGRNA

<400> SEQUENCE: 37
ggatgtaacc ctatagggt tgcgtgagtc ggccatagtg cctcggcaac agcgtaaaaa     60
actgctgcca gtggtcgaag taagtcaaca aaaatgtagg cctactggca c            111

<210> SEQ ID NO 38
<211> LENGTH: 108
<212> TYPE: DNA
<213> ORGANISM: Artificial Sequence
<220> FEATURE:
<223> OTHER INFORMATION: TEST SGRNA

<400> SEQUENCE: 38 ggtaaccta tagggttgc gtgagtcggc catagtgcct cggcaacagc gtaaaaact       60 gctgccagtg gtcgaagtaa gtcaacaaaa atgtaggcct actggcac               108

<210> SEQ ID NO 39
<211> LENGTH: 112
<212> TYPE: DNA
<213> ORGANISM: Artificial Sequence
<220> FEATURE:
<223> OTHER INFORMATION: TEST SGRNA

<400> SEQUENCE: 39
gggatgtaac cctatagggg ttgcgtgagt cggccatagt gcctcggcaa cagcgtaaaa    60
aactgctgcc agtggtcgaa gtaagtcaac aaaaatgtag gcctactggc ac          112

<210> SEQ ID NO 40
<211> LENGTH: 109
<212> TYPE: DNA
<213> ORGANISM: Artificial Sequence
<220> FEATURE:
<223> OTHER INFORMATION: TEST SGRNA

<400> SEQUENCE: 40
gggtaaccct atagggggttg cgtgagtcgg ccatagtgcc tcggcaacag cgtaaaaaac   60
tgctgccagt ggtcgaagta agtcaacaaa aatgtaggcc tactggcac              109

<210> SEQ ID NO 41
<211> LENGTH: 109
<212> TYPE: DNA
<213> ORGANISM: Artificial Sequence
<220> FEATURE:
<223> OTHER INFORMATION: TEST SGRNA

<400> SEQUENCE: 41
cggagggaac tccgtgaacg tgtcttcccc ttcgatgggc ttggcacacg ggtcaatcg     60 agttgccgtt gaaggcggcg aattcgccgg catctcgatc gaccgacac              109

<210> SEQ ID NO 42
```

-continued

```
<211> LENGTH: 91
<212> TYPE: DNA
<213> ORGANISM: Artificial Sequence
<220> FEATURE:
<223> OTHER INFORMATION: TEST SGRNA

<400> SEQUENCE: 42
ggagggaact ccgtgaacgt gtcttcccct tcgatgggct tggcacacgg ggtcaatcga      60
gttgccaaaa ggcatctcga tcgaccgaca c                                    91

<210> SEQ ID NO 43
<211> LENGTH: 81
<212> TYPE: DNA
<213> ORGANISM: Artificial Sequence
<220> FEATURE:
<223> OTHER INFORMATION: TEST SGRNA

<400> SEQUENCE: 43
ggagggaact ccgtgaacgt gtcttcccct tcgatgggct tggcacacgg ggtcaatcga      60
gttatctcga tcgaccgaca c                                               81

<210> SEQ ID NO 44
<211> LENGTH: 98
<212> TYPE: DNA
<213> ORGANISM: Artificial Sequence
<220> FEATURE:
<223> OTHER INFORMATION: TEST SGRNA

<400> SEQUENCE: 44
ggcaggcgga gggaactccg tgaacgtgtc ttccccttcg atgggcttgg cacacggggt      60
caatcgagtt gccaaaaggc atctcgatcg accgacac                             98

<210> SEQ ID NO 45
<211> LENGTH: 88
<212> TYPE: DNA
<213> ORGANISM: Artificial Sequence
<220> FEATURE:
<223> OTHER INFORMATION: TEST SGRNA

<400> SEQUENCE: 45
ggcaggcgga gggaactccg tgaacgtgtc ttccccttcg atgggcttgg cacacggggt      60
caatcgagtt atctcgatcg accgacac                                        88

<210> SEQ ID NO 46
<211> LENGTH: 129
<212> TYPE: DNA
<213> ORGANISM: Artificial Sequence
<220> FEATURE:
<223> OTHER INFORMATION: TEST SGRNA

<400> SEQUENCE: 46
ttgcctctac aggaggcgag aatgccacgg cacgtgtctt cccttcaat gggcttggca       60 ccgtggagtc gatcagtttt gtgccggcga agggttgccg acgtcagcac caacctgatc    120
gacggacac                                                            129

<210> SEQ ID NO 47
<211> LENGTH: 93
<212> TYPE: DNA
<213> ORGANISM: Artificial Sequence
<220> FEATURE:
<223> OTHER INFORMATION: TEST SGRNA

<400> SEQUENCE: 47
```
gcctctacag gaggcgagaa tgccacggca cgtgtcttcc ccttcaatgg gcttggcacc    60
gtggagtcga tcagaaaact gatcgacgga cac                                93

<210> SEQ ID NO 48
<211> LENGTH: 95
<212> TYPE: DNA
<213> ORGANISM: Artificial Sequence
<220> FEATURE:
<223> OTHER INFORMATION: TEST SGRNA

<400> SEQUENCE: 48
gggcctctac aggaggcgag aatgccacgg cacgtgtctt cccccttcaat gggcttggca    60 ccgtggagtc gatcagaaaa ctgatcgacg gacac                                95

<210> SEQ ID NO 49
<211> LENGTH: 102
<212> TYPE: DNA
<213> ORGANISM: Artificial Sequence
<220> FEATURE:
<223> OTHER INFORMATION: TEST SGRNA

<400> SEQUENCE: 49
gggacattgg cctctacagg aggcgagaat gccacggcac gtgtcttccc cttcaatggg    60
cttggcaccg tggagtcgat cagaaaactg atcgacggac ac                       102

<210> SEQ ID NO 50
<211> LENGTH: 133
<212> TYPE: DNA
<213> ORGANISM: Artificial Sequence
<220> FEATURE:
<223> OTHER INFORMATION: TEST SGRNA

<400> SEQUENCE: 50
gtcgcctata gggcgataca actccgagca tgtgtcttcc ccttcaatgg gcttggcact    60
cggcatcgat caagctcgcg tcggctgtcg ggccaaagcc gcgtcggccg acgcggcctt   120
gatcgatgga cac                                                       133

<210> SEQ ID NO 51
<211> LENGTH: 120
<212> TYPE: DNA
<213> ORGANISM: Artificial Sequence
<220> FEATURE:
<223> OTHER INFORMATION: TEST SGRNA

<400> SEQUENCE: 51
gtcgcctata gggcgataca actccgagca tgtgtcttcc ccttcaatgg gcttggcact    60
cggcatcgat caagctcgcg tcggctgtcg tcggccgacg cggccttgat cgatggacac   120

<210> SEQ ID NO 52
<211> LENGTH: 108
<212> TYPE: DNA
<213> ORGANISM: Artificial Sequence
<220> FEATURE:
<223> OTHER INFORMATION: TEST SGRNA

<400> SEQUENCE: 52
gtcgcctata gggcgataca actccgagca tgtgtcttcc ccttcaatgg gcttggcact    60
cggcatcgat caagctcgcg taaaaacgcg gccttgatcg atggacac                 108

<210> SEQ ID NO 53

-continued

```
<211> LENGTH: 121
<212> TYPE: DNA
<213> ORGANISM: Artificial Sequence
<220> FEATURE:
<223> OTHER INFORMATION: TEST SGRNA

<400> SEQUENCE: 53
ggtcgcctat agggcgatac aactccgagc atgtgtcttc cccttcaatg ggcttggcac     60
tcggcatcga tcaagctcgc gtcggctgtc gtcggccgac gcggccttga tcgatggaca    120
c                                                                    121

<210> SEQ ID NO 54
<211> LENGTH: 110
<212> TYPE: DNA
<213> ORGANISM: Artificial Sequence
<220> FEATURE:
<223> OTHER INFORMATION: TEST SGRNA

<400> SEQUENCE: 54
gggtcgccta tagggcgata caactccgag catgtgtctt ccccttcaat gggcttggca     60
ctcggcatcg atcaagctcg cgtaaaaacg cggccttgat cgatggacac               110

<210> SEQ ID NO 55
<211> LENGTH: 20
<212> TYPE: DNA
<213> ORGANISM: Artificial Sequence
<220> FEATURE:
<223> OTHER INFORMATION: PRIMER SEQUENCE

<400> SEQUENCE: 55
ttgggtaacg ccagggtttt                                                 20

<210> SEQ ID NO 56
<211> LENGTH: 20
<212> TYPE: DNA
<213> ORGANISM: Artificial Sequence
<220> FEATURE:
<223> OTHER INFORMATION: PRIMER SEQUENCE

<400> SEQUENCE: 56
tgtgtggaat tgtgagcgga                                                 20

<210> SEQ ID NO 57
<211> LENGTH: 20
<212> TYPE: DNA
<213> ORGANISM: Artificial Sequence
<220> FEATURE:
<223> OTHER INFORMATION: PRIMER SEQUENCE

<400> SEQUENCE: 57
aaacccctcc gtttagagag                                                 20

<210> SEQ ID NO 58
<211> LENGTH: 29
<212> TYPE: DNA
<213> ORGANISM: Artificial Sequence
<220> FEATURE:
<223> OTHER INFORMATION: PRIMER SEQUENCE

<400> SEQUENCE: 58
aagctaatac gactcactat aggccagtc                                       29

<210> SEQ ID NO 59
<211> LENGTH: 20
```

```
<212> TYPE: DNA
<213> ORGANISM: Artificial Sequence
<220> FEATURE:
<223> OTHER INFORMATION: PRIMER SEQUENCE

<400> SEQUENCE: 59
ccagtcagta atgttactgg                                              20

<210> SEQ ID NO 60
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 60
ccggtggtgc agatgaactt cag                                          23

<210> SEQ ID NO 61
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 61
aagaagtcgt gctgcttcat gtg                                          23

<210> SEQ ID NO 62
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 62
ccgtaggtgg catcgccctc gcc                                          23

<210> SEQ ID NO 63
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 63
gggcatggcg gacttgaaga agt                                          23

<210> SEQ ID NO 64
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 64
tggccgttta cgtcgccgtc cag                                          23

<210> SEQ ID NO 65
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 65
```
aagaagatgg tgcgctcctg gac                                          23

<210> SEQ ID NO 66
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 66
gccggtggtg cagatgaact tca                                          23

<210> SEQ ID NO 67
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 67
atctgcacca ccggcaaact gcc                                          23

<210> SEQ ID NO 68
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 68
agcgtgtccg gcgagggcga ggg                                          23

<210> SEQ ID NO 69
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 69
gtgaccaccc tgacctacgg cgt                                          23

<210> SEQ ID NO 70
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 70
agccgctacc ccgaccacat gaa                                          23

<210> SEQ ID NO 71
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 71
ttcaagtccg ccatgcccga agg                                          23

<210> SEQ ID NO 72
<211> LENGTH: 23
<212> TYPE: DNA
<213> ORGANISM: Artificial Sequence

```
<220> FEATURE:
<223> OTHER INFORMATION: PRIMER SEQUENCE

<400> SEQUENCE: 72
ttcaaggacg acggcaacta caa                                              23

<210> SEQ ID NO 73
<211> LENGTH: 23
<212> TYPE: DNA
<213> ORGANISM: Artificial Sequence
<220> FEATURE:
<223> OTHER INFORMATION: PRIMER SEQUENCE

<400> SEQUENCE: 73
aaggacgacg gcaactacaa gac                                              23
```